US012751922B2

(12) United States Patent
Pinkhassik et al.

(10) Patent No.: US 12,751,922 B2
(45) Date of Patent: Oct. 6, 2026

(54) ASSISTED LOADING OF HYDROPHOBIC MOLECULES INTO LIPOSOMES

(71) Applicant: UNIVERSITY OF CONNECTICUT, Farmington, CT (US)

(72) Inventors: Evgueni Pinkhassik, Newton, MA (US); Sergey Dergunov, Vernon, CT (US); Weiyu Zhang, Willington, CT (US)

(73) Assignee: University of Connecticut, Farmington, CT (US)

( * ) Notice: Subject to any disclaimer, the term of this patent is extended or adjusted under 35 U.S.C. 154(b) by 313 days.

(21) Appl. No.: 18/280,165

(22) PCT Filed: Mar. 8, 2022

(86) PCT No.: PCT/US2022/019367
§ 371 (c)(1),
(2) Date: Sep. 1, 2023

(87) PCT Pub. No.: WO2022/192275
PCT Pub. Date: Sep. 15, 2022

(65) Prior Publication Data
US 2024/0165029 A1 May 23, 2024

Related U.S. Application Data

(60) Provisional application No. 63/157,960, filed on Mar. 8, 2021.

(51) Int. Cl.
*A61K 9/127* (2025.01)
*A61K 9/1278* (2025.01)
(Continued)

(52) U.S. Cl.
CPC .......... *A61K 9/1278* (2013.01); *A61K 31/015* (2013.01); *A61K 31/047* (2013.01);
(Continued)

(58) Field of Classification Search
None
See application file for complete search history.

(56) References Cited

U.S. PATENT DOCUMENTS

2006/0165822 A1 7/2006 Van Der Giessen et al.
2013/0237408 A1 9/2013 Pinkhassik et al.
(Continued)

FOREIGN PATENT DOCUMENTS

WO PCT/US2022/19367 3/2022

OTHER PUBLICATIONS

Saffari, M., et al., "Terpene-loaded Liposomes and Isopropyl Myristate as Chemical Permeation Enhancers Toward Liposomal Gene Delivery in Lung Cancer cells; A Comparative Study," Iranian Journal of Pharmaceutical Research (2016), 15(3), 261-267.
(Continued)

*Primary Examiner* — Brian Gulledge
(74) *Attorney, Agent, or Firm* — McCarter & English, LLP

(57) ABSTRACT

The present disclosure is concerned with unilamellar liposomes and methods of making same. The disclosed unilamellar liposomes can be useful in, for example, delivering a cargo molecule (e.g., a nucleic acid) and also in inducing an immune response. This abstract is intended as a scanning tool for purposes of searching in the particular art and is not intended to be limiting of the present invention.

18 Claims, 48 Drawing Sheets

Specification includes a Sequence Listing.

(51) Int. Cl.

| | |
|---|---|
| ***A61K 9/50*** | (2006.01) |
| ***A61K 31/015*** | (2006.01) |
| ***A61K 31/047*** | (2006.01) |
| ***A61K 31/122*** | (2006.01) |
| ***A61K 31/4704*** | (2006.01) |
| ***A61K 31/4709*** | (2006.01) |
| ***A61K 31/7105*** | (2006.01) |
| ***A61K 31/711*** | (2006.01) |
| ***A61K 47/06*** | (2006.01) |

(52) U.S. Cl.

CPC ........ *A61K 31/122* (2013.01); *A61K 31/4704* (2013.01); *A61K 31/4709* (2013.01); *A61K 31/7105* (2013.01); *A61K 31/711* (2013.01); *A61K 47/06* (2013.01)

(56) References Cited

U.S. PATENT DOCUMENTS

2017/0231920 A1* 8/2017 de Sousa Martins ........................ A61K 9/0009 604/501
2019/0015521 A1* 1/2019 Roizman ................. A61P 29/00
2019/0024088 A1* 1/2019 Hinkle ................. A61K 31/585

OTHER PUBLICATIONS

U.S. Appl. No. 63/157,960, filed Mar. 8, 2021, Pinkhassik, et al. (University of Conneticut).

Uppal et al., Palmitoylation of Metazoan Carotenoid Oxygenases. Molecules. Apr. 22, 2020;25(8):1942, 17 pages.

Uppal et al., The dual roles of RPE65 S-palmitoylation in membrane association and visual cycle function. Sci Rep. Mar. 26, 2019;9(1):5218, 14 pages.

Vage et al., A nonsense mutation in the beta-carotene oxygenase 2 (BCO2) gene is tightly associated with accumulation of carotenoids in adipose tissue in sheep (*Ovis aries*). BMC Genet. Feb. 2, 2010;11:10, 6 pages.

Wang et al., Actions of beta-apo-carotenoids in differentiating cells: differential effects in P19 cells and 3T3-L1 adipocytes. Arch Biochem Biophys. Apr. 15, 2015;572:2-10.

Waterhouse et al., Swiss-Model: homology modelling of protein structures and complexes. Nucleic Acids Res. Jul. 2, 2018;46(W1):W296-W303.

Widomska et al., Can Xanthophyll-Membrane Interactions Explain Their Selective Presence in the Retina and Brain? Foods. Mar. 2016;5(1):7, 19 pages.

Widomska et al., Mechanisms enhancing the protective functions of macular xanthophylls in the retina during oxidative stress. Exp Eye Res. Jan. 2019;178:238-246.

Wu et al., Molecular aspects of beta, beta-carotene-9', 10'-oxygenase 2 in carotenoid metabolism and diseases. Exp Biol Med (Maywood). Nov. 2016;241(17):1879-1887.

Zhang et al., I-TASSER server for protein 3D structure prediction. BMC Bioinformatics. Jan. 23, 2008;9:40, 8 pages.

Ziouzenkova et al., Asymmetric cleavage of beta-carotene yields a transcriptional repressor of retinoid X receptor and peroxisome proliferator-activated receptor responses. Mol Endocrinol. Jan. 2007;21(1):77-88.

Amengual et al., A mitochondrial enzyme degrades carotenoids and protects against oxidative stress. FASEB J. Mar. 2011;25(3):948-59.

Babino et al., Characterization of the Role of beta-Carotene 9,10-Dioxygenase in Macular Pigment Metabolism. J Biol Chem. Oct. 9, 2015;290(41):24844-57.

Babino et al., The Biochemical Basis of Vitamin A3 Production in Arthropod Vision. ACS Chem Biol. Apr. 15, 2016;11(4):1049-57.

Bernstein et al., Lutein, zeaxanthin, and meso-zeaxanthin: The basic and clinical science underlying carotenoid-based nutritional interventions against ocular disease. Prog Retin Eye Res. Jan. 2016;50:34-66.

Berry et al., Mutation in bovine beta-carotene oxygenase 2 affects milk color. Genetics. Jul. 2009;182(3):923-6.

Boesch-Saadatmandi et al., Comparison of tetrahydrofuran, fetal calf serum, and Tween 40 for the delivery of astaxanthin and canthaxanthin to HepG2 cells. Cytotechnology. Jan. 2011;63(1):89-97.

Bone et al., Analysis of the macular pigment by HPLC: retinal distribution and age study. Invest Ophthalmol Vis Sci. Jun. 1988;29(6):843-9.

Chakraborty et al., How cholesterol stiffens unsaturated lipid membranes. Proc Natl Acad Sci U S A. Sep. 8, 2020;117(36):21896-21905.

Connor et al., The prime role of HDL to transport lutein into the retina: evidence from HDL-deficient WHAM chicks having a mutant ABCA1 transporter. Invest Ophthalmol Vis Sci. Sep. 2007;48(9):4226-31.

Dela Sena et al., Substrate Specificity of Purified Recombinant Chicken beta-Carotene 9', 10'-Oxygenase (BCO2). J Biol Chem. Jul. 8, 2016;291(28):14609-19.

Delmelle, An Investigation of Retinal as a Source of Singlet Oxygen. Photochemistry and Photobiology. Jun. 1978;27(6):731-734.

Demmig-Adams et al., Zeaxanthin and Lutein: Photoprotectors, Anti-Inflammatories, and Brain Food. Molecules. Aug. 8, 2020;25(16):3607, 14 pages.

Dergunov et al., Liposomal delivery of a phosphodiesterase 3 inhibitor rescues low oxygen-induced ATP release from erythrocytes of humans with type 2 diabetes. Biochem Biophys Rep. May 30, 2015;2:137-142.

During et al., Xanthophylls are preferentially taken up compared with beta-carotene by retinal cells via a SRBI-dependent mechanism. J Lipid Res. Aug. 2008;49(8):1715-24.

Eriksson et al., Identification of the yellow skin gene reveals a hybrid origin of the domestic chicken. PLoS Genet. Feb. 29, 2008;4(2):e1000010, 8 pages.

Eroglu et al., Naturally occurring eccentric cleavage products of provitamin A beta-carotene function as antagonists of retinoic acid receptors. J Biol Chem. May 4, 2012;287(19):15886-95.

Eroglu et al., The eccentric cleavage product of beta-carotene, beta-apo-13-carotenone, functions as an antagonist of RXRalpha. Arch Biochem Biophys. Dec. 1, 2010;504(1):11-6.

Frede et al., Lutein Activates the Transcription Factor Nrf2 in Human Retinal Pigment Epithelial Cells. J Agric Food Chem. Jul. 26, 2017;65(29):5944-5952.

Grudzinski et al., Localization and Orientation of Xanthophylls in a Lipid Bilayer. Sci Rep. Aug. 29, 2017;7(1):9619, 10 pages.

Gruszecki et al., Carotenoids as modulators of lipid membrane physical properties. Biochim Biophys Acta. May 30, 2005;1740(2):108-15.

Guo et al., Ablation of beta, beta-carotene-9', 10'-oxygenase 2 remodels the hypothalamic metabolome leading to metabolic disorders in mice. J Nutr Biochem. Aug. 2017;46:74-82.

Johnson et al., Relationship between Serum and Brain Carotenoids, alpha-Tocopherol, and Retinol Concentrations and Cognitive Performance in the Oldest Old from the Georgia Centenarian Study. J Aging Res. 2013;2013:951786, 13 pages.

Kiefer et al., Identification and characterization of a mammalian enzyme catalyzing the asymmetric oxidative cleavage of provitamin A. J Biol Chem. Apr. 27, 2001;276(17):14110-6.

Kim et al., Photooxidation of A2-PE, a photoreceptor outer segment fluorophore, and protection by lutein and zeaxanthin. Exp Eye Res. May 2006;82(5):828-39.

Lazrak et al., Comparison of the effects of inserted C40- and C50-terminally dihydroxylated carotenoids on the mechanical properties of various phospholipid vesicles. Biochim Biophys Acta. Sep. 18, 1987;903(1):132-41.

Li et al., Identification of StARD3 as a lutein-binding protein in the macula of the primate retina. Biochemistry. Apr. 5, 2011;50(13):2541-9.

Li et al., Inactivity of human beta, beta-carotene-9', 10'-dioxygenase (BCO2) underlies retinal accumulation of the human macular carotenoid pigment. Proc Natl Acad Sci U S A. Jul. 15, 2014;111(28):10173-8.

(56) References Cited

OTHER PUBLICATIONS

Li et al., Xanthophylls lutein and zeaxanthin modify gene expression and induce synthesis of hyaluronan in keratinocyte model of human skin. Biochem Biophys Rep. Aug. 21, 2015;4:52-58.
Lindqvist et al., Cell type-specific expression of beta-carotene 9', 10'-monooxygenase in human tissues. J Histochem Cytochem. Nov. 2005;53(11):1403-12.
Loane et al., Transport and retinal capture of lutein and zeaxanthin with reference to age-related macular degeneration. Surv Ophthalmol. Jan.-Feb. 2008;53(1):68-81.
Lobo et al., BCDO2 acts as a carotenoid scavenger and gatekeeper for the mitochondrial apoptotic pathway. Development. Aug. 2012;139(16):2966-77.
Mares-Perlman et al., The body of evidence to support a protective role for lutein and zeaxanthin in delaying chronic disease. Overview. J Nutr. Mar. 2002;132(3):518S-524S.
Meyers et al., Genetic evidence for role of carotenoids in age-related macular degeneration in the Carotenoids in Age-Related Eye Disease Study (CAREDS). Invest Ophthalmol Vis Sci. Jan. 29, 2014;55(1):587-99.
Milon et al., Organization of Carotenoid-Phospholipid Bilayer Systems. Incorporation of Zeaxanthin, Astaxanthin, and their C50 Homologues into Dimyristoylphosphatidylcholine vesicles. Helvetica. Feb. 5, 1986;69(1):12-24.
Mortensen et al., Free radical transients in photobleaching of xanthophylls and carotenes. Free Radic Res. Jun. 1997;26(6):549-63.
Nacke et al., Liposome based solubilisation of carotenoid substrates for enzymatic conversion in aqueous media. Journal of Molecular Catalysis B: Enzymatic. Sep. 2011;71(3-4):133-138.
Nolan et al., Nutritional Intervention to Prevent Alzheimer's Disease: Potential Benefits of Xanthophyll Carotenoids and Omega-3 Fatty Acids Combined. J Alzheimers Dis. 2018;64(2):367-378.
Palczewski et al., Evidence for compartmentalization of mammalian carotenoid metabolism. FASEB J. Oct. 2014;28(10):4457-69.
Poliakov et al., Phylogenetic analysis of the metazoan carotenoid oxygenase superfamily: a new ancestral gene assemblage of BCO-like (BCOL) proteins. Sci Rep. Oct. 16, 2017;7(1):13192, 12 pages.
Rapp et al., Lutein and zeaxanthin concentrations in rod outer segment membranes from perifoveal and peripheral human retina. Invest Ophthalmol Vis Sci. Apr. 2000;41(5):1200-9.
Redmond et al., Mutation of key residues of RPE65 abolishes its enzymatic role as isomerohydrolase in the visual cycle. Proc Natl Acad Sci U S A. Sep. 20, 2005;102(38):13658-63.
Roy et al., Cofacter: an accurate comparative algorithm for structure-based protein function annotation. Nucleic Acids Res. Jul. 2012;40(Web Server issue):W471-7.
Roy et al., I-TASSER: a unified platform for automated protein structure and function prediction. Nat Protoc. Apr. 2010;5(4):725-38.
Scott et al., On the Mechanism of Bilayer Separation by Extrusion, or Why Your LUVs Are Not Really Unilamellar. Biophys J. Oct. 15, 2019;117(8):1381-1386.
Shivarudrappa et al., Lutein reverses hyperglycemia-mediated blockage of Nrf2 translocation by modulating the activation of intracellular protein kinases in retinal pigment epithelial (ARPE-19) cells. J Cell Commun Signal. Jun. 2020;14(2):207-221.
Socaciu et al., Carotenoid incorporation into microsomes: yields, stability and membrane dynamics. Spectrochim Acta A Mol Biomol Spectrosc. Dec. 2000;56(14):2799-809.
Thomas et al., The human mitochondrial enzyme BCO2 exhibits catalytic activity toward carotenoids and apocarotenoids. J Biol Chem. Nov. 13, 2020;295(46):15553-15565.
Trott et al., AutoDock Vina: improving the speed and accuracy of docking with a new scoring function, efficient optimization, and multithreading. J Comput Chem. Jan. 30, 2010;31(2):455-61.

* cited by examiner

BCO2-V5 tagged 0.15μM *Lutein treated*

BCO2-V5 tagged 0.45μM *Zeaxanthin treated*

BCO2-V5 tagged *Untreated*

BCO2-V5 tagged 0.45μM *violaxanthin treated*

BCO2-V5 tagged 0.15 µM *Lutein treated*

BCO2-V5 tagged 0.06 μM *Lutein treated*

```
SEQUENCE LISTING

<160> NUMBER OF SEQ ID NOS: 3

<210> SEQ ID NO 1
<211> LENGTH: 15
<212> TYPE: PRT
<213> ORGANISM: Artificial sequence
<220> FEATURE:
<223> OTHER INFORMATION: Synthetic construct

<400> SEQUENCE: 1

Ser Lys Phe Leu Gln Ser Asp Thr Tyr Lys Ala Asn Ser Ala Gly
1               5                   10                  15


<210> SEQ ID NO 2
<211> LENGTH: 17
<212> TYPE: PRT
<213> ORGANISM: Artificial sequence
<220> FEATURE:
<223> OTHER INFORMATION: Synthetic construct

<400> SEQUENCE: 2

Ser His Glu Asn Leu His Gln Glu Asp Leu Glu Lys Glu Gly Gly Ile
1               5                   10                  15

Glu


<210> SEQ ID NO 3
<211> LENGTH: 19
<212> TYPE: PRT
<213> ORGANISM: Artificial sequence
<220> FEATURE:
<223> OTHER INFORMATION: Synthetic construct

<400> SEQUENCE: 3

Gln Asp Asn Gly Arg Thr Leu Glu Val Tyr Gln Leu Gln Asn Leu Arg
1               5                   10                  15

Lys Ala Gly
```

ASSISTED LOADING OF HYDROPHOBIC MOLECULES INTO LIPOSOMES

CROSS-REFERENCE TO RELATED APPLICATIONS

This Application is a U.S. National Phase of International Application No. PCT/US2022/019367, filed on Mar. 8, 2022, which claims the benefit of U.S. Provisional Application No. 63/157,960, filed on Mar. 8, 2021, the contents of which are incorporated herein by reference in their entireties.

STATEMENT OF GOVERNMENT SUPPORT

This invention was made with Government support under Grant No. CHE-1709921 awarded by the National Science Foundation. The Government has certain rights in the invention.

REFERENCE TO SEQUENCE LISTING

The Sequence Listing submitted Sep. 1, 2023 as a text file named "38100 0039U2 ST25.txt" created on Aug. 31, 2023, and having a size of 1,084 bytes is hereby incorporated by reference pursuant to 37 C.F.R. § 1.52 (e)(5).

BACKGROUND

It is well established that liposomes are used as a vehicle/carrier for transporting hydrophobic and/or hydrophilic molecules. In non-limiting examples, liposomes are currently used by pharmaceutical companies as drug delivery vehicles, by cosmetic companies in skin care products, by textile companies for dye delivery vehicles, by food companies for enzyme and nutritional supplement delivery, and by plant/chemical companies for pesticide delivery.

Traditional methods are based on mixing lipids with the appropriate hydrophobic cargo materials followed by hydration of the mixture to produce large multilamellar vesicles as shown in FIG. 1. Thereafter, the large multilamellar vesicles go through an extrusion process to produce unilamellar vesicles with the desired size. However, the existing technology has several shortcomings, for example, cost, difficulties in solubilization of large cargo materials (e.g., hydrophobic cargo materials) and challenges with extrusion due to the incorporation of cargo materials within a bilayer.

Accordingly, a need exists for a more simplified process for preparing liposomes. The simplified process described herein will save time and money compared to existing technology.

SUMMARY

In accordance with the purpose(s) of the invention, as embodied and broadly described herein, the invention, in one aspect, relates to systems and methods of preparing a liposome from a lipid with an assisting molecule. Additionally, disclosed are systems and methods of preparing a liposome from a lipid loaded with an assisting molecule and a cargo material (e.g., hydrophobic cargo materials). Additionally, disclosed is a simplified loading of an assisting molecule with a lipid to form a liposome. Therefore, the present disclosure describes systems and methods for reducing costs and broadening the utility of liposomes in a plurality of applications such as, for example, pharmaceutical and cosmetic applications.

Disclosed are methods of making a unilamellar liposome, the method comprising mixing a lipid, an assisting molecule, and a cargo molecule, thereby forming a mixture, and loading the mixture into a lipid bilayer.

Also disclosed are methods of making a unilamellar liposome, the method comprising mixing a lipid and an assisting molecule, thereby forming a mixture, and loading the mixture into a lipid bilayer, wherein the lipid bilayer does not contain limonene or cineole.

Also disclosed are methods of making a unilamellar liposome, the method comprising mixing a lipid and an assisting molecule, thereby forming a mixture, and loading the mixture into a lipid bilayer, wherein the molar ratio of the assisting molecule to the lipid is of from about 0.25:1 to about 2:1.

Also disclosed are methods of making a unilamellar liposome, the method comprising mixing a lipid, a monoterpene, and a nucleic acid, thereby forming a mixture, and loading the mixture into a lipid bilayer, wherein the molar ratio of the assisting molecule to the lipid is of from about 0.25:1 to about 2:1.

Also disclosed are unilamellar liposomes prepared by a disclosed method.

Also disclosed are unilamellar liposomes comprising a mixture of a lipid, an assisting molecule, and a cargo molecule, wherein the mixture is loaded into a lipid bilayer.

Also disclosed are pharmaceutical compositions comprising an effective amount of a disclosed unilamellar liposome and a pharmaceutically acceptable carrier.

Also disclosed are methods of delivery a cargo molecule to a subject in need thereof, the method comprising administering to the subject an effective amount of a disclosed unilamellar liposome.

Also disclosed are methods of inducing an immune response in a subject in need thereof, the method comprising administering to the subject an effective amount of a disclosed unilamellar liposome.

Also disclosed are systems comprising: (a) a lipid; (b) an assisting molecule; and (c) a cargo molecule.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 7A are structures showing the intramolecular dimensions of carotenoids and DMPC/DPPC bilayer as calculated by molecular mechanics. The length of the carotenoid (lutein or zeaxanthin) corresponds to the length of the lipophilic segment of the DMPC phospholipid (double the average distance between the carbonyl group and the methyl group of the DMPC), and does not match the length of the lipophilic segment of the DPPC. FIG. 7B shows a representative plot of SAXS data of DMPC-zeaxanthin and DPPC-zeaxanthin LUVs. FIG. 7C is a representative Kratky plot from SAXS data, supporting the formation of unilamellar LUVs. FIG. 7D is a representative DLS plot showing the size distribution and the average diameter of DMPC-zeaxanthin and DPPC-zeaxanthin LUVs.

FIG. 9A is a representative HPLC profile of zeaxanthin extracted from 10 mL of cells after 5 hours of treatment. FIG. 9C is a representative HPLC profile of zeaxanthin extracted from 1 mL of media directly after adding it to cells. Zeaxanthin preparation contained residual lutein (zeaxanthin is major peak at 15.1 min, and lutein is peak at 12.7 min). Zeaxanthin was separated with a gradient of 10-60% B, where A=acetonicitrile:water:trimethylamine (90:10:0.1) and B=100% ethyl acetate.

FIG. 10A is a representative image showing treatment with 0.15 μM lutein. FIG. 10B is a representative image showing treatment with 0.06 μM lutein. FIG. 10C is a representative image showing treatment with 0.45 μM zeaxanthin. FIG. 10D is a representative image showing treatment with 0.6 μM violaxanthin. Equal amounts (~50 μg) of the total (indicated as "input") and eluted protein from control (indicated as "−") and hydroxylamine (HAM)-treated (indicated as "+") were subjected to SDS-PAGE and immunoblotting. Western blot results are representative of three independent experiments as shown in the supplementary figures. mBCO2 loses its palmitoylation in the presence of substrate.

FIG. 11A is a representative image showing treatment with 0.15 μM lutein. FIG. 11B is a representative image showing treatment with 0.45 μM zeaxanthin. FIG. 11C is a representative image showing treatment with 0.6 μM violaxanthin. FIG. 11D is a representative image showing treatment with 0.06 μM lutein.

FIG. 13A shows a representative fluorescence image of the untreated control. FIG. 13B shows a representative fluorescence image of COS7 cells expressing mBCO2 protein treated with 0.15 μM lutein. FIG. 13C is a plot showing representative data for Pearson's correlation coefficient for colocalization of V5-tagged mBCO2 protein with different organellar marker proteins. FIG. 13D is a plot showing representative data for Pearson's correlation coefficient for colocalization of V5-tagged mBCO2 protein with nucleus. COS7 cells expressing mBCO2 protein treated with 0.15 μM lutein for 5 h were immunoassayed using antibodies against V5 tag and different organelle marker proteins as indicated in the Materials and Methods section. * $p \leq 0.05$; *** $p \leq 0.0005$.

FIG. 14A shows a representative fluorescence image of the untreated control. FIG. 14B shows a representative fluorescence image of COS7 cells expressing mBCO2 protein treated with 0.45 μM zeaxanthin. FIG. 14C is a plot showing representative data for Pearson's correlation coefficient for colocalization of VS-tagged mBCO2 protein with different organellar marker proteins. FIG. 14D is a plot showing representative data for Pearson's correlation coefficient for colocalization of V5-tagged mBCO2 protein with nucleus. COS7 cells expressing V5-tagged mouse BCO2 protein treated with 0.45 μM zeaxanthin for 5 h were immunoassayed using antibodies against V5 tag and different organelle marker proteins as indicated in the Materials and Methods section. * $p \leq 0.05$; *** $p \leq 0.0005$.

FIG. 15A shows a representative fluorescence image of the untreated control. FIG. 15B shows a representative fluorescence image of COS7 cells expressing mBCO2 protein treated with 0.6 μM violaxanthin. FIG. 15C is a plot showing representative data for Pearson's correlation coefficient for colocalization of VS-tagged mBCO2 protein with different organellar marker proteins. FIG. 15D is a plot showing representative data for Pearson's correlation coefficient for colocalization of V5-tagged mBCO2 protein with nucleus.) COS7 cells expressing mBCO2 protein treated with 0.6 μM violaxanthin for 5 h were immunoassayed using antibodies against V5 tag and different organelle marker proteins as indicated in the Materials and Methods section. * $p \leq 0.05$; *** $p \leq 0.0005$.

FIG. 16A shows a representative fluorescence image of mBCO2 with and without 0.15 μM lutein. FIG. 16B shows a representative fluorescence image of mBCO2 with and without 0.06 μM lutein. FIG. 16C is a plot showing representative data for the Pearson's correlation coefficients calculated for colocalization of VS-tagged mBCO2 protein with nucleus.

FIG. 17A is a visualization showing the docking on the mBCO2 protein I-TASSER model. FIG. 17B is a visualization showing the docking on the mBCO2 protein Swiss-Model model.

Figure 1:
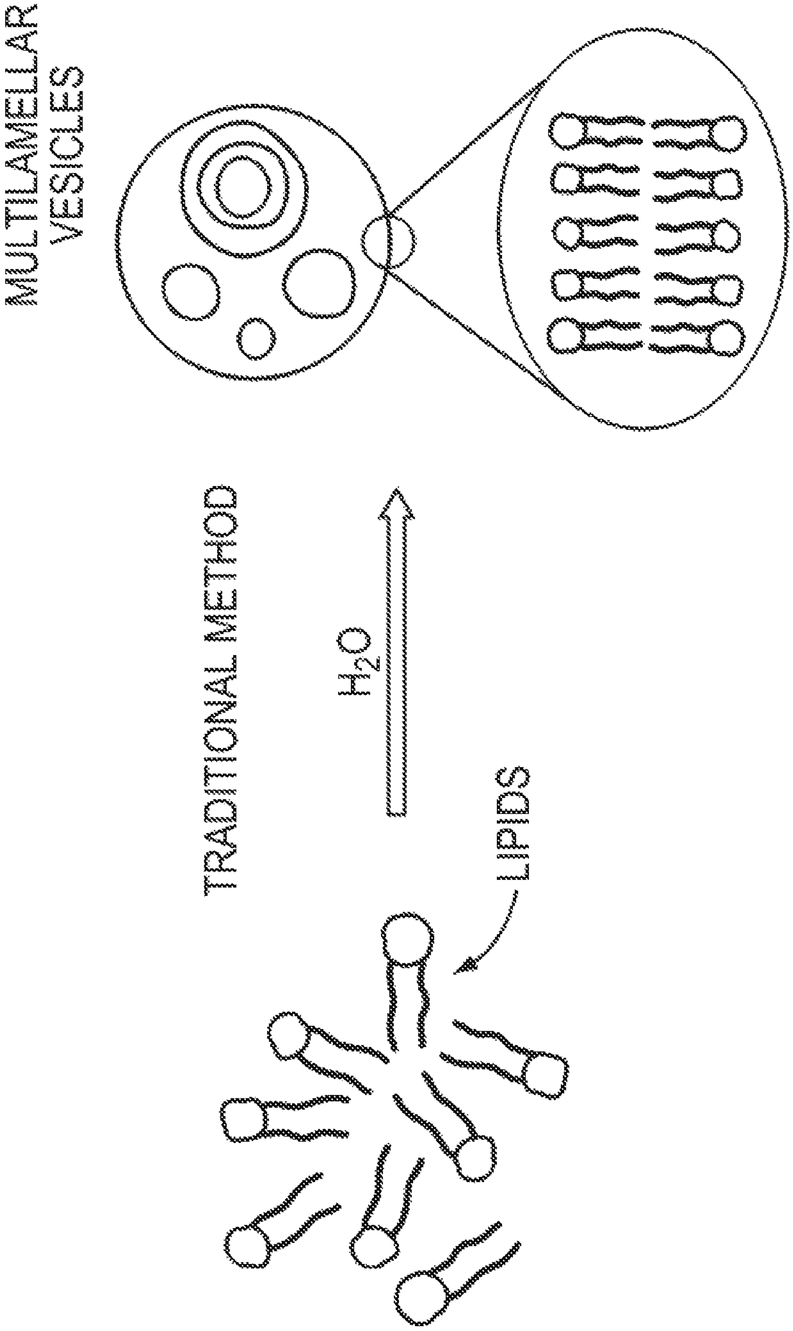
FIG. 1 shows a representative schematic illustrating the formation of multilamellar vesicles.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed. All ranges disclosed herein are inclusive of the endpoints, and the endpoints are independently combinable with each other. Each range disclosed herein constitutes a disclosure of any point or sub-range lying within the disclosed range.

As used herein, the term "about" refers to a measurable value such as a parameter, an amount, a temporal duration, and the like and is meant to include variations of +/−15% or less, preferably variations of +/−10% or less, more preferably variations of +/−5% or less, even more preferably variations of +/−1% or less, and still more preferably variations of +/−0.1% or less of and from the particularly recited value, in so far as such variations are appropriate to perform in the invention described herein. Furthermore, it is also to be understood that the value to which the modifier "about" refers is itself specifically disclosed herein. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

As used herein, spatially relative terms, such as "beneath," "below," "lower," "above," "upper," "front," "back," "side," "left," "right," "rear," and the like, are used for ease of description to describe one element or feature's relationship to another element(s) or feature(s). It is further understood that the terms "front," "back," "left," and "right" are not intended to be limiting and are intended to be interchangeable, where appropriate. Further, it should be noted that the terms "first," "second," and the like herein do not denote any order, quantity, or relative importance, but rather are used to distinguish one element from another.

As used herein, the terms "comprise(s)," "comprising," and the like, specify the presence of stated features, integers, steps, operations, elements, and/or components, but do not preclude the presence or addition of one or more other features, integers, steps, operations, elements, components, and/or groups thereof.

As used herein, the terms "configure(s)," "configuring," and the like, refer to the capability of a component and/or assembly, but do not preclude the presence or addition of other capabilities, features, components, elements, operations, and any combinations thereof.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the terms "liposome" and "vesicle," and the like, are used interchangeably, unless otherwise stated or understood from the context. In some instances, liposome describes an artificially prepared vesicle formed from lipids. In some instances, large unilamellar vesicle (LUV) refers to a similar structure as unilamellar liposome or unilamellar liposome/vesicle.

As used herein, the term "assisting molecule" refers to a molecule that facilitates incorporation of a hydrophobic cargo molecule (e.g., a nucleic acid) into the lipid bilayer. In various aspects, the assisting molecule is a monomer. Exemplary monomers include, but are not limited to, monoterpenes, divinylbenzene, tert-butylstyrene, tert-butylmethacrylate, butylmethacrylate, and 1,4-butanediol dimethacrylate. In various further aspects, the assisting molecule is a terpene such as, for example, a monoterpene. Examples of monoterpenes include, but are not limited to, limonene, geraniol, α-terpineol, thymol, menthol, carvone, eucalyptol, perillaldehyde, myrcene, mentho, carvone, hinokitiol, linalool, careen, sabinene, camphor, menthol, camphene, thujene, camphor, borneol, eucalyptol, and ascaridole.

As used herein, the term "cargo molecule" refers to a hydrophobic molecule, the loading of which is facilitated or enabled by the presence of an assisting molecule. Exemplary cargo molecules include, but are not limited to, peptides, proteins, polysaccharides, lipids, combinations thereof including lipoproteins and glycolipids, nucleic acids (e.g., cDNA, miRNA, mRNA, antisense oligonucleotides, decoy DNA, plasmid), small molecule drugs (e.g., cyclosporine A, paclitaxel, doxorubicin, methotrexate, 5-aminolevulinic acid), imaging agents (e.g., fluorophore, quantum dots (QDs), radioactive tracers). In a further aspect, the cargo molecule is Lutein, Zeaxantin, Violaxantin, Astaxantin, Carotene, Cilostazol, Cilostamide, or a combination thereof.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene 9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, and amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions that can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

Chemical compounds are described using standard nomenclature. For example, any position not substituted by any indicated group is understood to have its valency filled by a bond as indicated, or a by hydrogen atom.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radioactively labeled forms, isomers, solvates and combinations thereof. The "combinations" mentioned in this context are refer to derivatives falling within at least two of the groups: pharmaceutically acceptable salts, prodrugs, deuterated forms, radioactively labeled forms, isomers, and solvates. Examples of radioactively labeled forms include compounds labeled with tritium, phosphorous-32, iodine-129, carbon-11, fluorine-18, and the like.

Compounds described herein comprise atoms in both their natural isotopic abundance and in non-natural abundance. The disclosed compounds can be isotopically labeled or isotopically substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules that owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

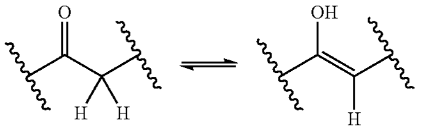

keto form enol form

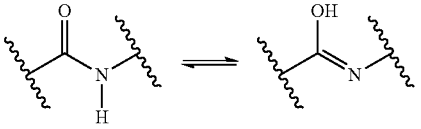

amide form imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

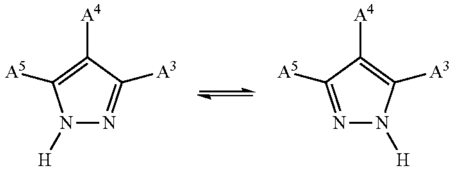

Unless stated to the contrary, the invention includes all such possible tautomers.

It is known that chemical substances form solids that are present in different states of order that are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Strem Chemicals (Newburyport, MA), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Any combination or permutation of features, functions and/or embodiments as disclosed herein is envisioned. Additional advantageous features, functions and applications of the disclosed systems, methods and assemblies of the present disclosure will be apparent from the description which follows, particularly when read in conjunction with the appended figures. All references listed in this disclosure are hereby incorporated by reference in their entireties.

B. Methods of Making a Unilamellar Liposome

In one aspect, disclosed are methods of making a unilamellar liposome, the method comprising mixing a lipid, an assisting molecule, and a cargo molecule, thereby forming a mixture, and loading the mixture into a lipid bilayer.

In one aspect, disclosed are methods of making a unilamellar liposome, the method comprising mixing a lipid and an assisting molecule, thereby forming a mixture, and loading the mixture into a lipid bilayer, wherein the lipid bilayer does not contain limonene or cineole.

In one aspect, disclosed are methods of making a unilamellar liposome, the method comprising mixing a lipid and an assisting molecule, thereby forming a mixture, and loading the mixture into a lipid bilayer, wherein the molar ratio of the assisting molecule to the lipid is of from about 0.25:1 to about 2:1.

In one aspect, disclosed are methods of making a unilamellar liposome, the method comprising mixing a lipid, a monoterpene, and a nucleic acid, thereby forming a mixture, and loading the mixture into a lipid bilayer, wherein the molar ratio of the assisting molecule to the lipid is of from about 0.25:1 to about 2:1.

As detailed herein, unilamellar liposomes of narrow size distribution are prepared using "sherpa" or assisting molecules that facilitate the formation of the liposomes without extrusion or sonication. Without wishing to be bound by theory, the disclosed methods simplifies the process to access unilamellar liposomes by facilitating the loading of hydrophobic molecules directly into the bilayer without the need for extrusion or other post-processing steps. Furthermore, the disclosed methods facilitate the solubilization of hydrophobic cargo molecules in the bilayer, which increases the loading.

Thus, in various aspects, disclosed are methods of making unilamellar liposomes from a lipid loaded with at least an assisting molecule, without the need for extrusion, sonication, or other methods for converting a multilamellar liposome into a unilamellar liposome. Thus, the present disclosure provides for simplified loading of assisting molecules that expands the range of molecules that can be loaded into liposomes. It should be understood, however, that the disclosed embodiments are merely illustrative of the present disclosure, which may be embodied in various forms. Therefore, details disclosed herein with reference to exemplary system/methods and associated process/techniques of assembly and use are not to be interpreted as limiting, but merely as the basis for teaching one skilled in the art how to make and use the advantageous system/method of the present disclosure.

Figure 2:
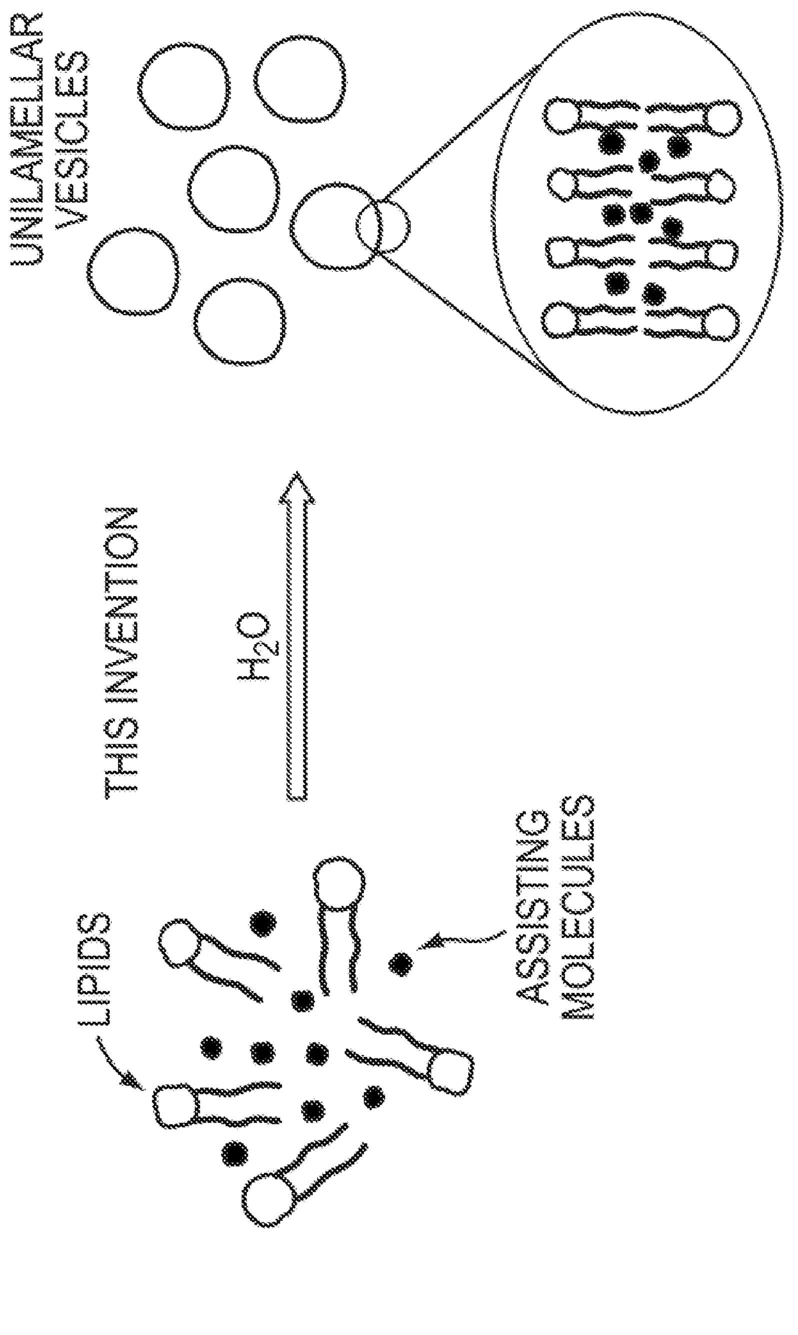
FIG. 2 shows a representative schematic illustrating the formation of unilamellar vesicles as disclosed herein.
Figure 3A:
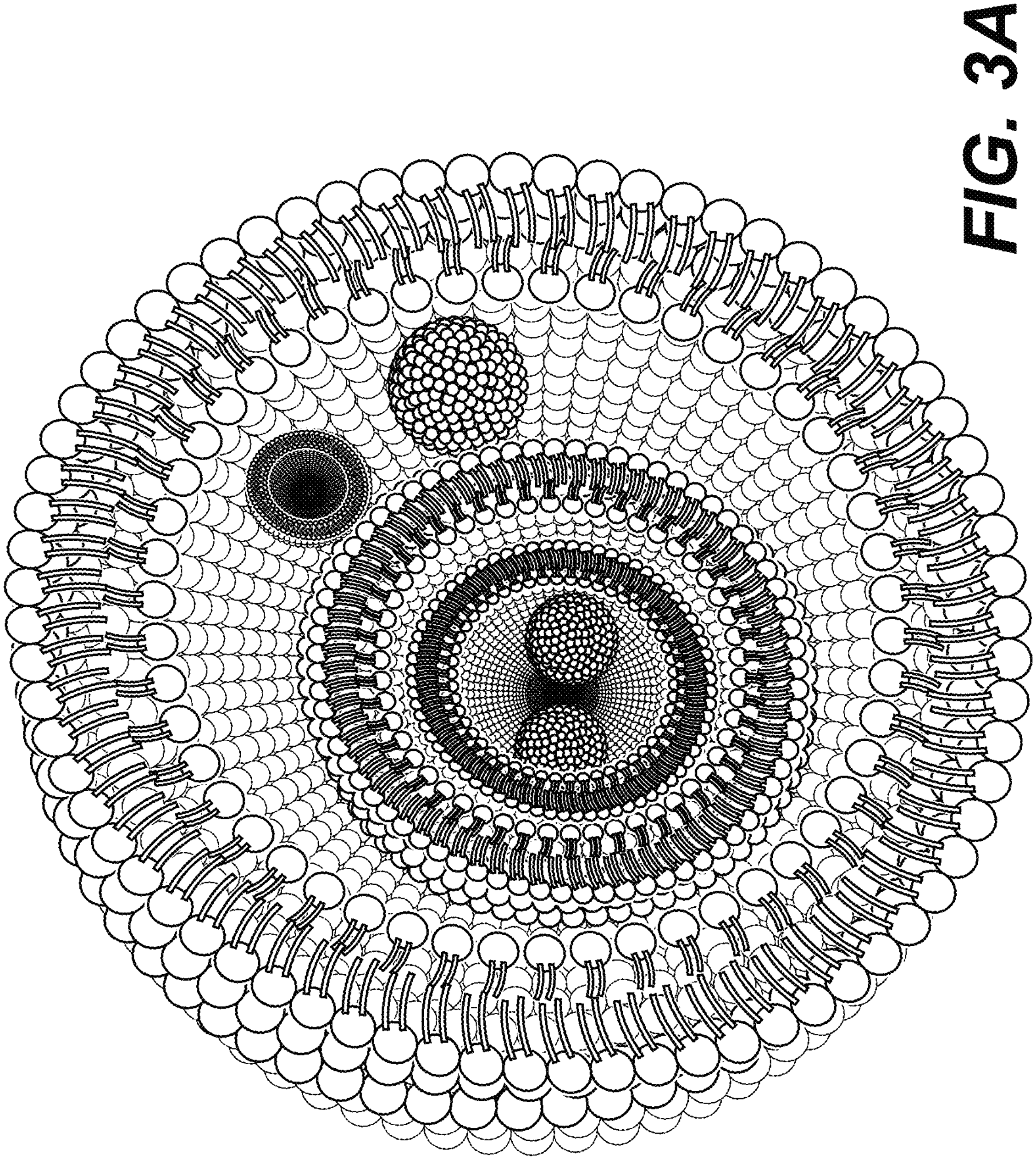
FIG. 3A-C show schematics illustrating a representative multilamellar vesicle (FIG. 3A), the size of that vesicle as measured by dynamic light scattering (FIG. 3B), and that vesicle imaged by electron microscopy (FIG. 3C).
Figure 3B:
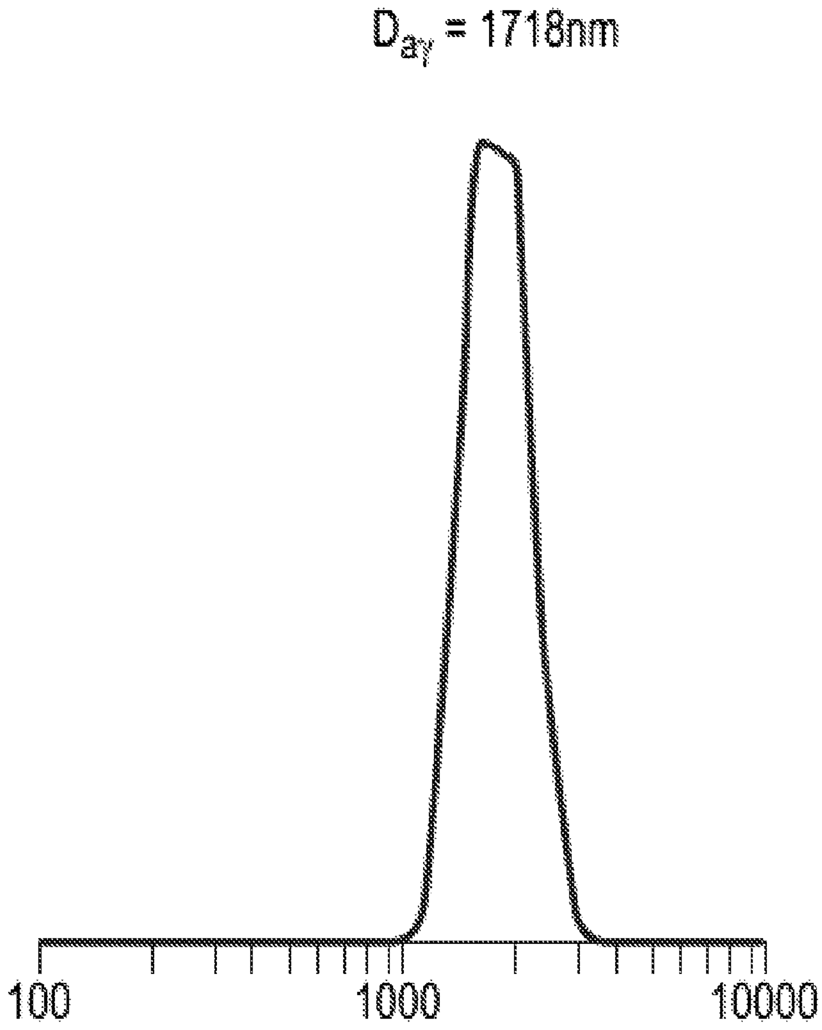
Figure 3C:
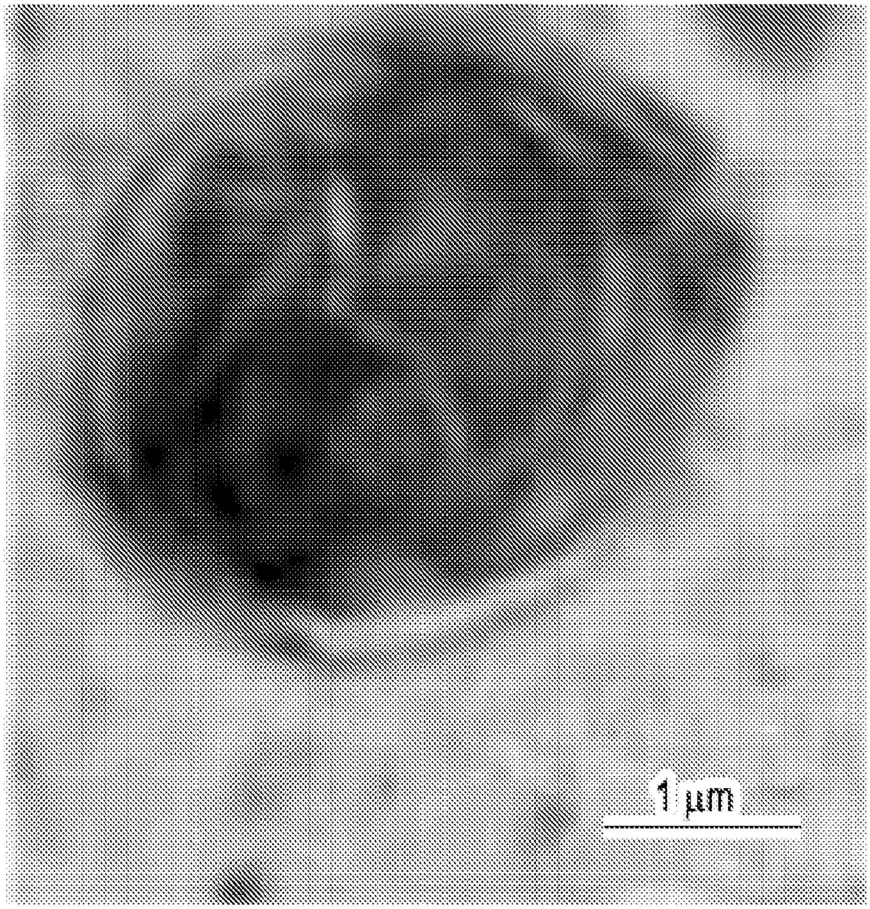

In various aspects, the disclosed methods simplify the process of creating unilamellar liposomes with assisting molecules (e.g., hydrophobic molecules) loaded directly into a bilayer, without the need for extrusion or other post-processing steps (e.g., sonication). The lipids are mixed with assisting molecules, as shown in FIG. 2. In this procedure, lipids are mixed with assisting molecules at molar ratio range between about 0.25:1 to about 10:1 and then hydrated with water or an aqueous buffer. For example, the molar ratio may be about 1:1. However, the molar ratio may, at least in part, depend the particular assisting molecule (e.g., characteristics/parameters of the particular assisting molecule). Unlike traditional methods where the hydration of lipids is accomplished in the absence of assisting molecules, this procedure produces predominantly unilamellar vesicles with narrow size distribution. Based thereon, the invention described herein prepares unilamellar liposomes with a narrow size distribution.

Figure 4A:
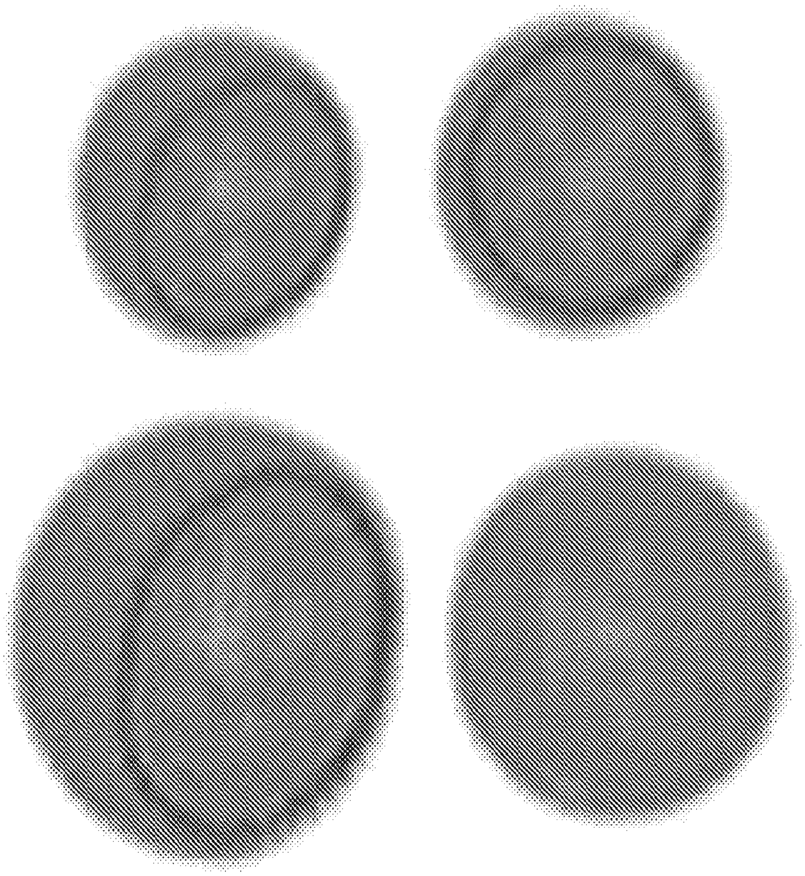
FIG. 4A-C show schematics illustrating a representative sketch of a unilamellar vesicle as described herein (FIG. 4A), the size of that vesicle as measured by dynamic light scattering (FIG. 4B), and that vesicle imaged by electron microscopy (FIG. 4C).
Figure 4B:
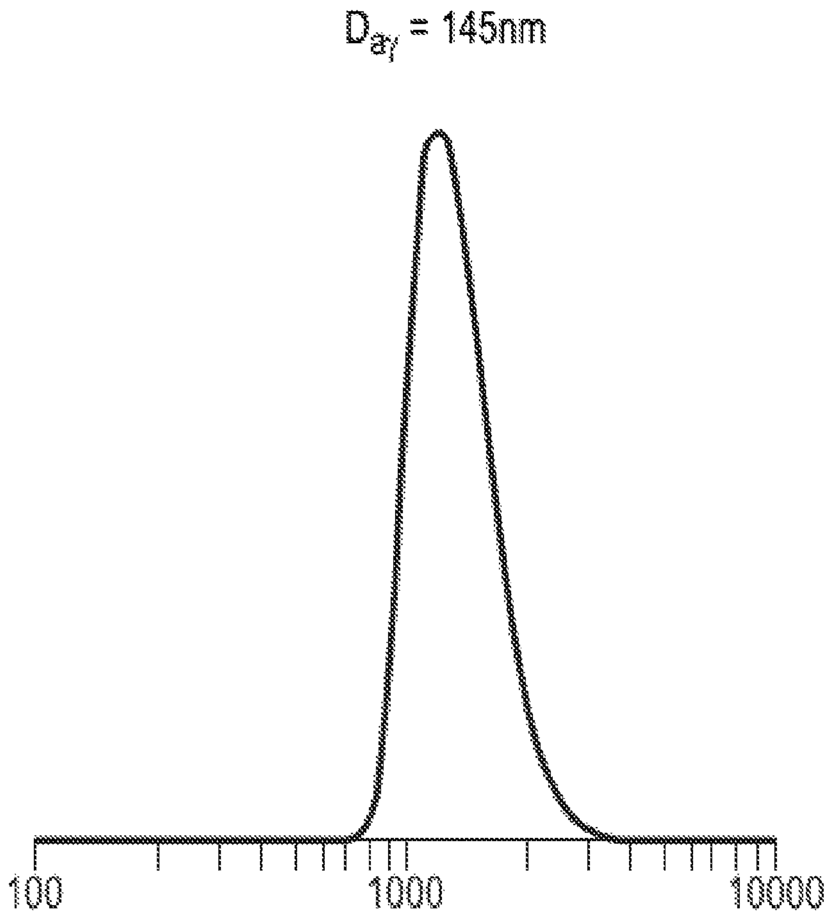
Figure 4C:
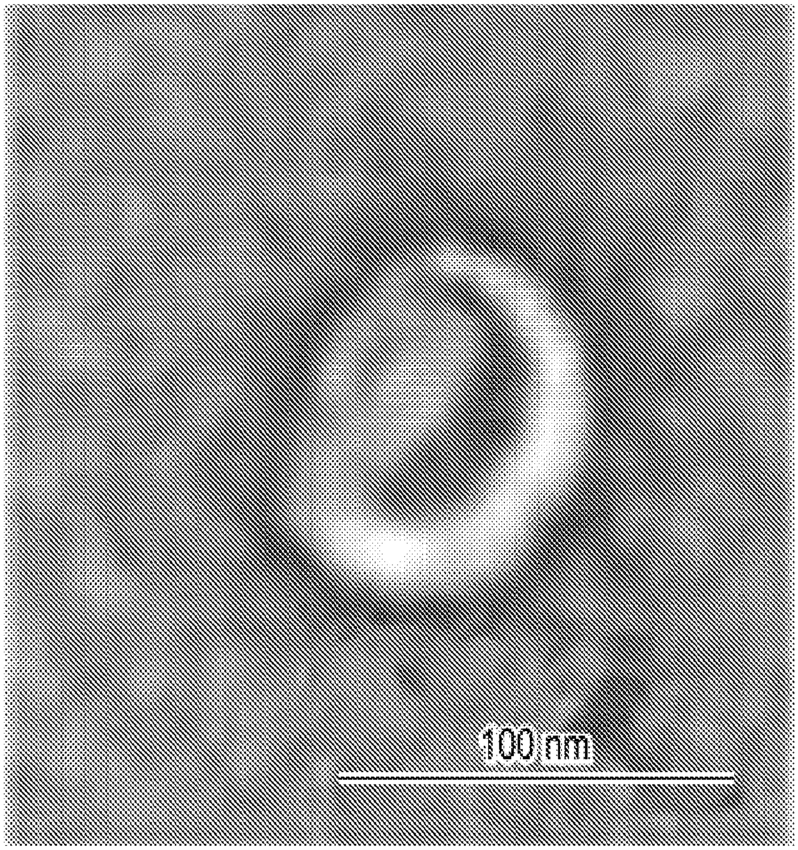

Referring to FIG. 4A-C, the formation of unilamellar vesicles using assisting molecules and characterization of vesicles is shown. FIG. 4A illustrates the sketch of the vesicle, FIG. 4B characterizes the size measured by dynamic light scattering and FIG. 4C illustrates the image of the vesicle produced by electron microscopy.

Figure 5:
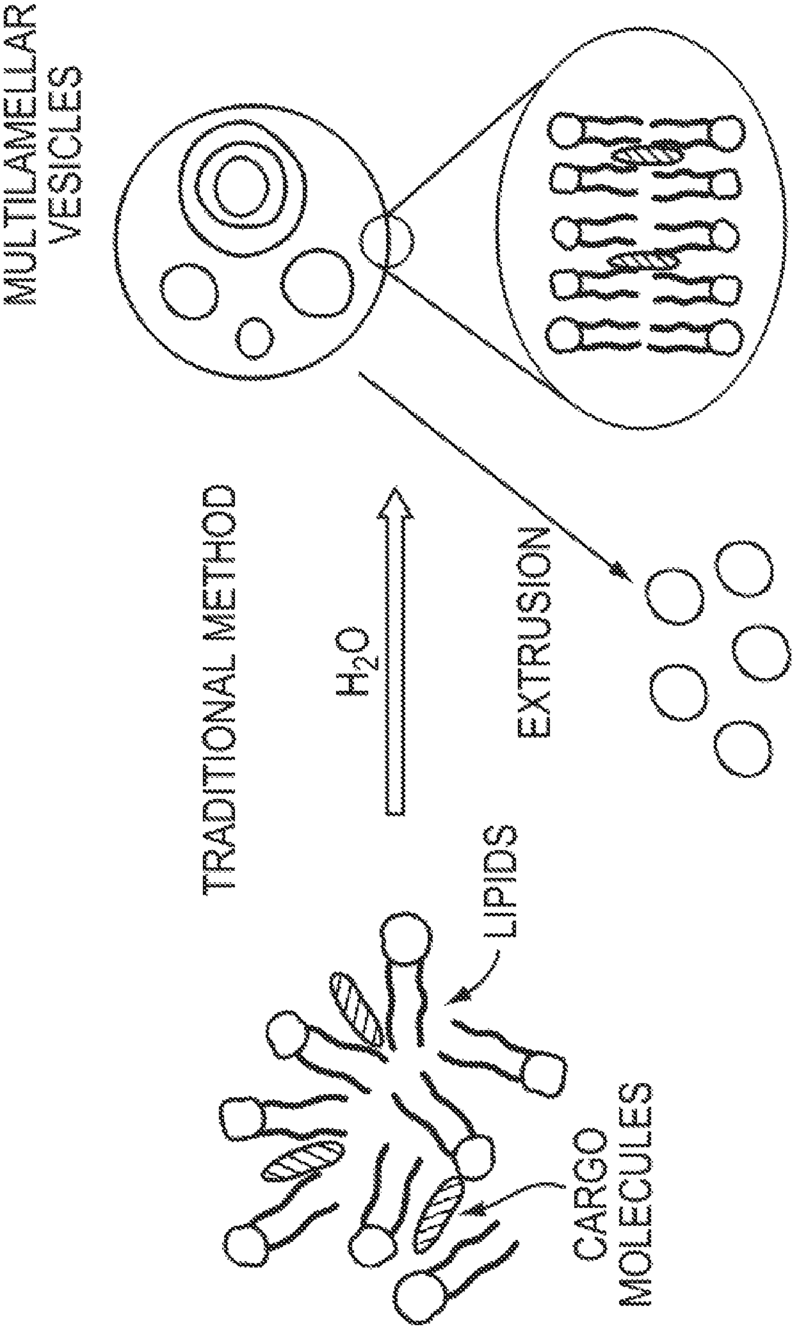
FIG. 5 shows a representative schematic illustrating the loading of cargo materials in multilamellar vesicles.
Figure 6:
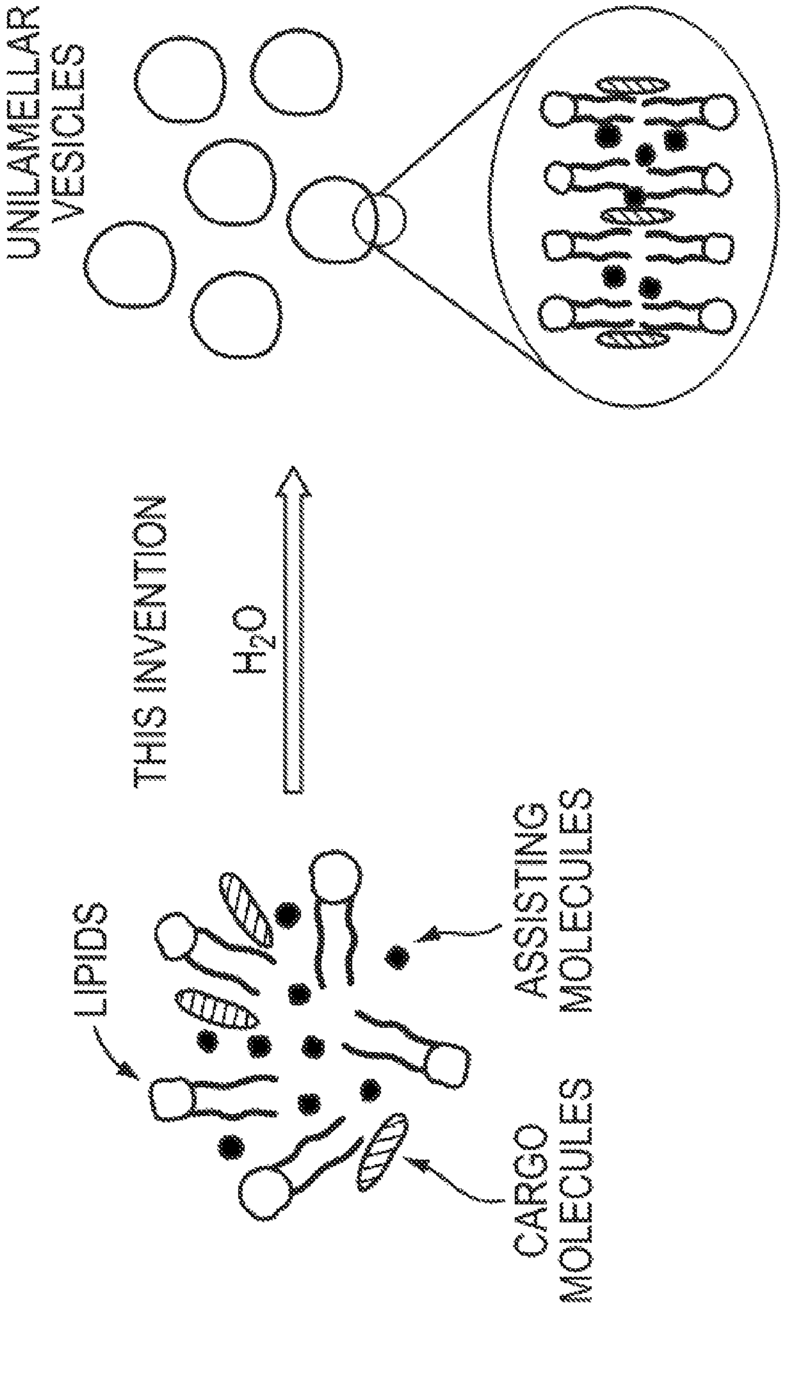
FIG. 6 shows a representative schematic illustrating the loading of cargo materials in unilamellar vesicles as described herein.
Figure 7A:
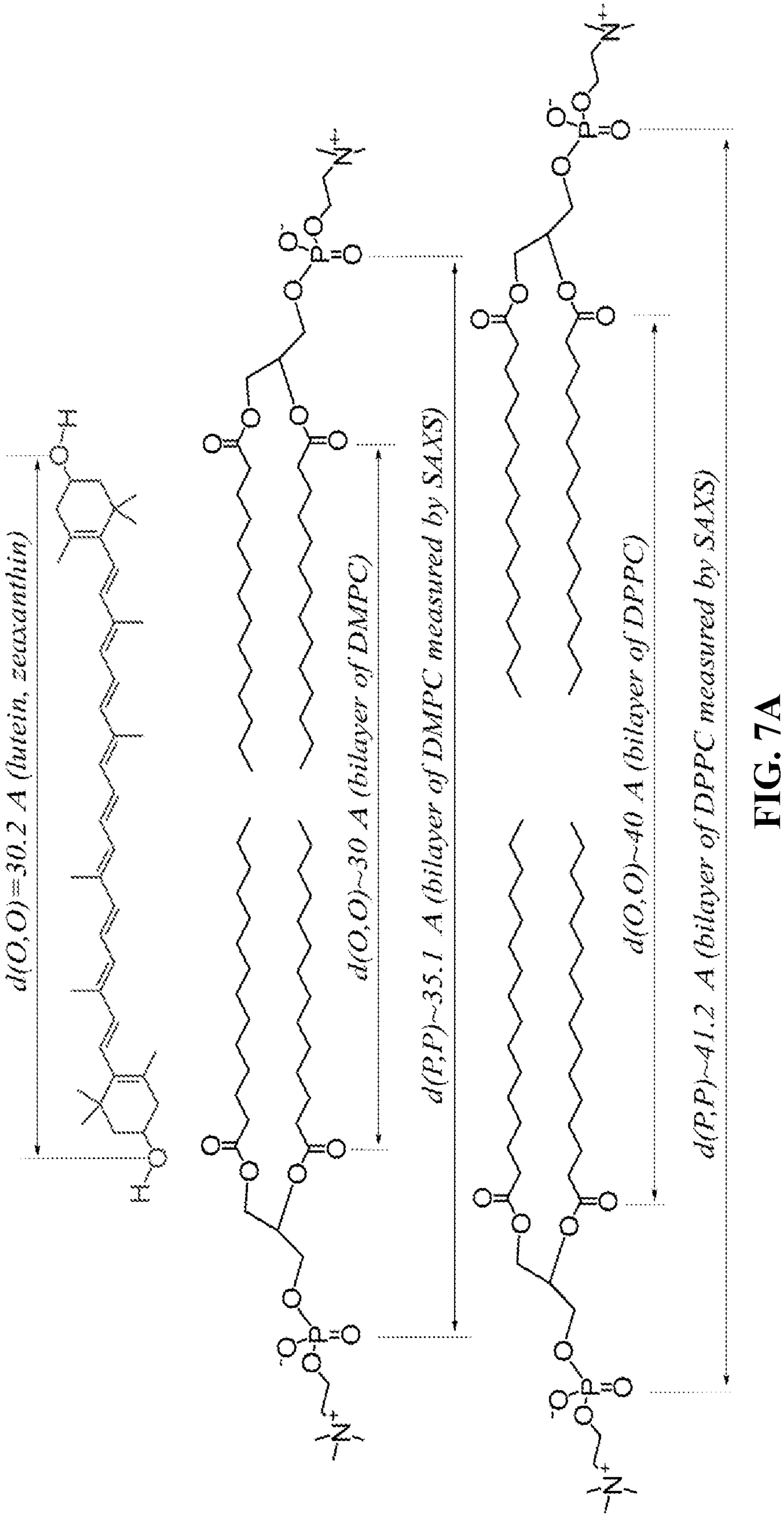
FIG. 7A-D show representative results for the characterization of LUVs.
Figure 7B:
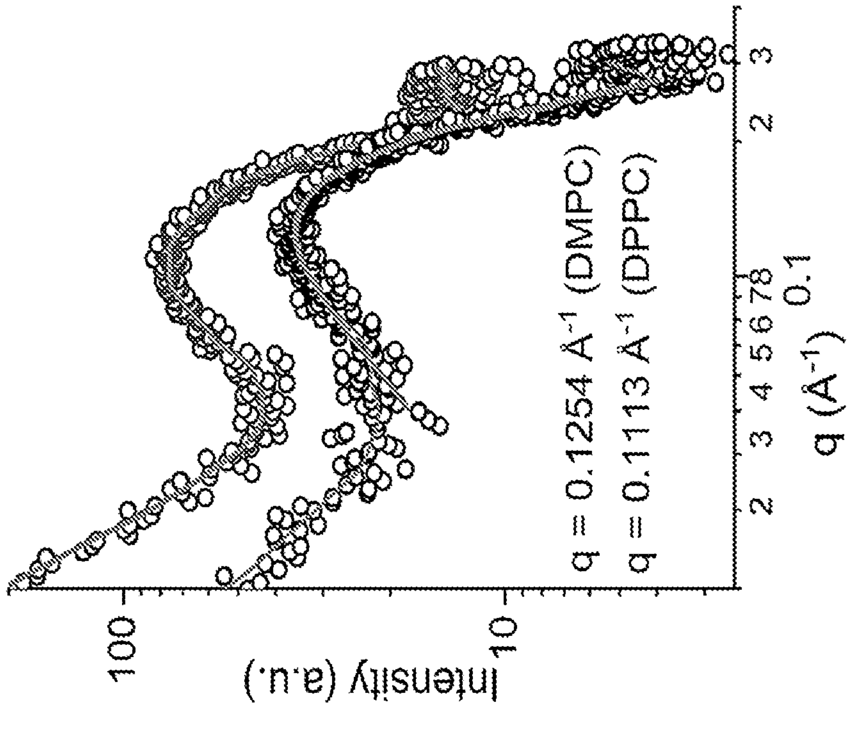
Figure 7C:
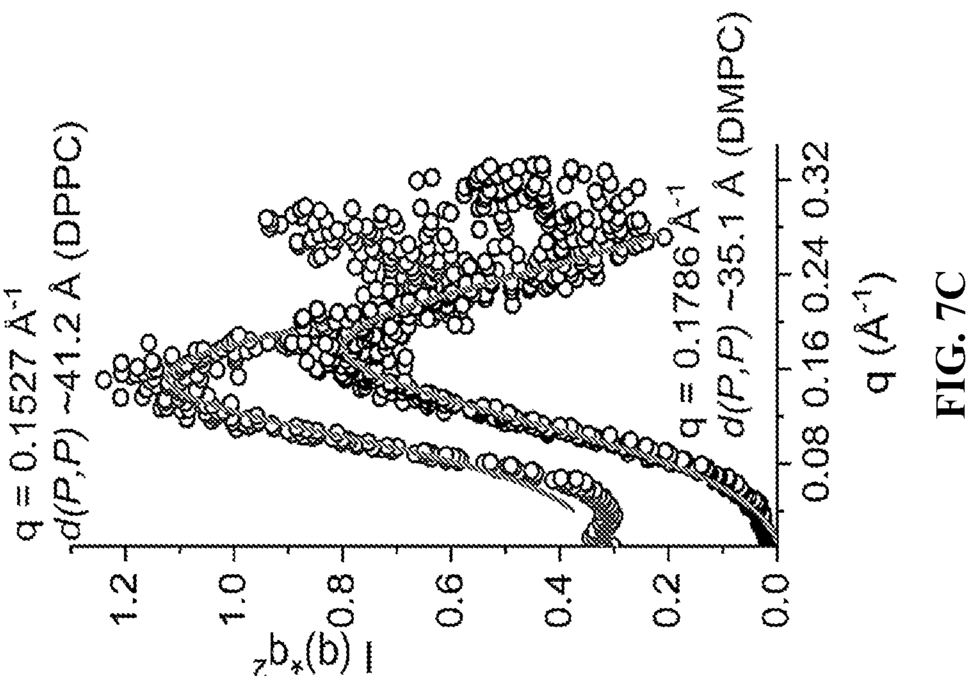
Figure 7D:
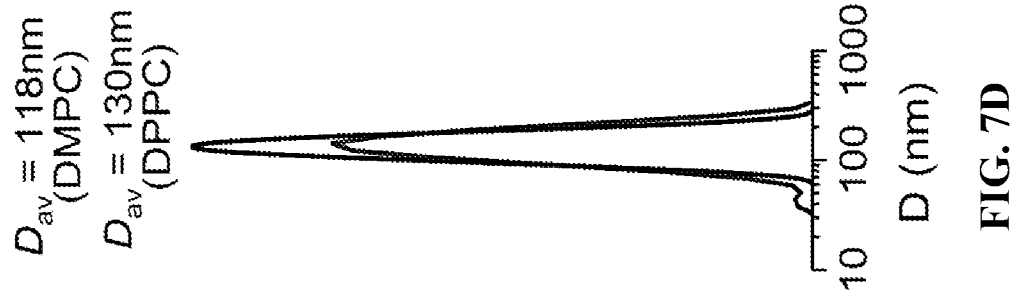
Figure 8:
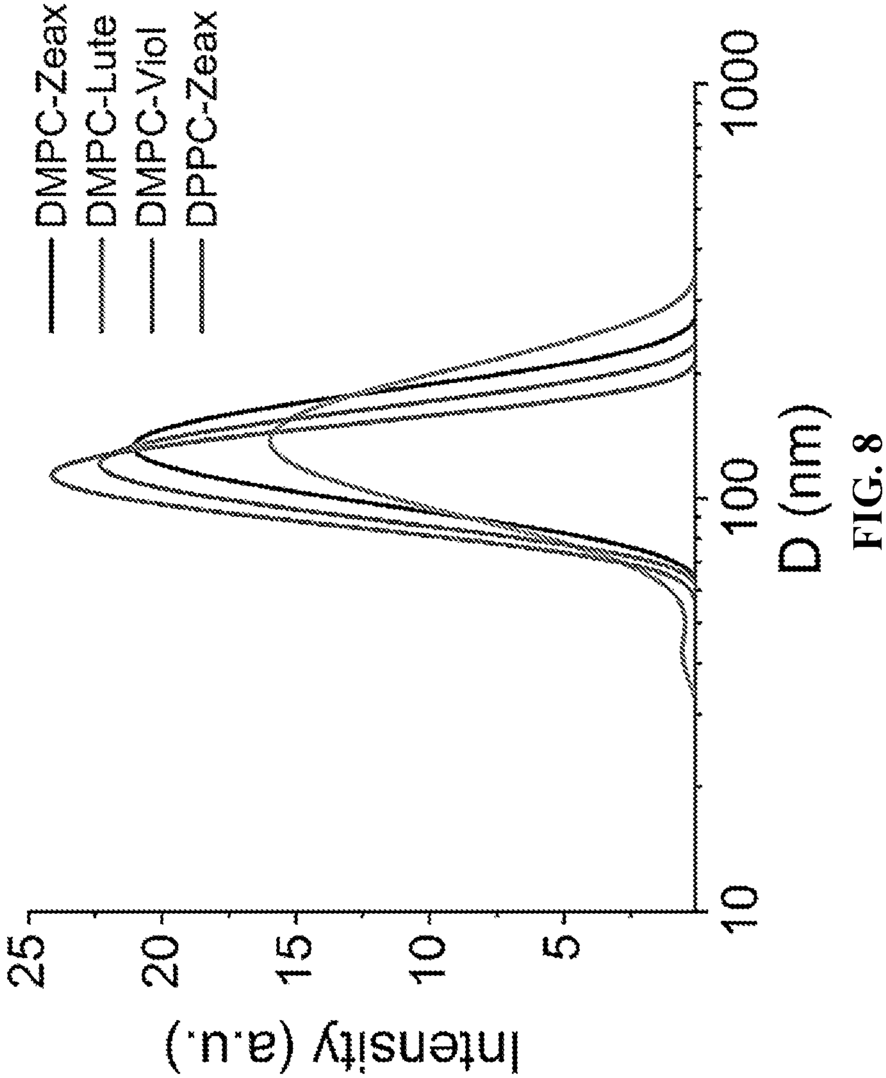
FIG. 8 is a representative dynamic light scattering plot for liposomes with xanthophylls.

In this procedure, a mixture of lipids, assisting hydrophobic molecules and hydrophobic cargo materials is hydrated with water or an aqueous buffer. The mixture of the lipid with the assisting molecule may have a molar ratio range of between about 0.25:1 to about 10:1, and in particular, a molar ratio of about 1:1. However, the molar ratio may, at least in part, depend on the particular assisting molecule (e.g., characteristics/parameters of the particular assisting molecule). The hydration produces unilamellar vesicles containing assisting molecules and cargo materials associated with the bilayer. Assisting molecules can be extracted with hexane or other organic solvent immiscible with water. The loading of cargo materials is schematically depicted in FIG. 5 and FIG. 6.

In contrast with existing methods, cargo-loaded unilamellar liposomes are produced directly from the mixture of lipids with cargo and assisting molecules upon hydration with water or an aqueous buffer. Elimination of the extrusion step greatly simplifies the scale-up of the fabrication of cargo-loaded liposomes, which is essential for large-scale production. In addition, the use of assisting molecules facilitates incorporation of molecules into the bilayer that would be difficult to load using traditional methods.

In various aspects, the method comprises mixing a lipid in combination with one or more of an assisting molecule and a cargo molecule. Examples of lipids include, but are not limited to, phosphatidylcholines and phosphatidylserines. In a further aspect, the lipid is 1,2-dimyristoyl-sn-glycero-3-phosphocholine (DMPC), 1,2-dimyristoyl-sn-glycero-3-phospho-L-serine (DMPS), 1,2-dipalmitoyl-sn-glycero-3-phosphocholine (DPPC), 1,2-dipalmitoyl-sn-glycero-3-phospho-L-serine (DPPS), or a combination thereof. In a still further aspect, the lipid is 1,2-dimyristoyl-sn-glycero-3-phosphocholine (DMPC) DMPC with 1-10%; 1,2-dimyristoyl-sn-glycero-3-phospho-L-serine (sodium salt) (DMPS); 1,2-dipalmitoyl-sn-glycero-3-phosphocholine (DPPC) DPPC with 1-10%; 1,2-dipalmitoyl-sn-glycero-3-phospho-L-serine (sodium salt) (DPPS); and combinations thereof. It should be understood that these are non-exhaustive lists of lipids.

In various aspects, the method comprises mixing an assisting molecule with the lipid and, optionally, a cargo molecule. In a further aspect, the assisting molecule is a terpene such as, for example, a monoterpene. Examples of monoterpenes include, but are not limited to, limonene, geraniol, α-terpineol, thymol, menthol, carvone, eucalyptol, perillaldehyde, myrcene, mentho, carvone, hinokitiol, linalool, careen, sabinene, camphor, menthol, camphene, thujene, camphor, borneol, eucalyptol, and ascaridole. In a still further aspect, the monoterpene is selected from limonene and geraniol. In yet a further aspect, the monoterpene is limonene. In an even further aspect, the assisting molecule is limonene, geraniol, divinylbenzene, tert-butylstyrene, tert-butylmethacrylate, butylmethacrylate, 1,4-butanediol dimethacrylate, or a combination thereof. In exemplary embodiments, the assisting molecule may be selected from the group including, but not limited to, hydrocarbons, alcohols, esters, aldehydes, ketones, amines, halogenated compounds. It should be understood that these are non-exhaustive lists of molecules. In a further aspect, the monoterpene is not limonene or cineole. In a still further aspect, the monoterpene is limonene.

In various aspects, the molar ratio of the assisting molecule to the lipid is of from about 0.25:1 to about 10:1, about 0.25:1 to about 8:1, from about 0.25:1 to about 6:1, from about 0.25:1 to about 4:1, from about 0.25:1 to about 2:1, or from about 0.25:1 to about 1:1. In a further aspect, the molar ratio of the assisting molecule to the lipid is about 1:1.

In various aspects, the molar ratio of the lipid to the assisting molecule is of from about 0.25:1 to about 10:1, about 0.25:1 to about 8:1, from about 0.25:1 to about 6:1, from about 0.25:1 to about 4:1, from about 0.25:1 to about 2:1, or from about 0.25:1 to about 1:1. In a further aspect, the molar ratio of the assisting molecule to the lipid is about 1:1.

In various aspects, the method comprises mixing a cargo molecule together with the lipid and the assisting molecule. Examples of cargo material includes, but is not limited to, Lutein, Zeaxantin, Violaxantin, Astaxantin, Carotene, Cilostazol, Cilostamide, or a combination thereof. In a further aspect, the cargo molecule is a nucleic acid such as, for example, deoxyribonucleic acid (DNA) or ribonucleic acid (RNA). In a still further aspect, the nucleic acid is DNA (e.g., complementary DNA or cDNA). In yet a further aspect, the nucleic acid is RNA (e.g., micro RNA or miRNA, messenger RNA or mRNA). It should be understood that these are non-exhaustive lists of molecules.

In various aspects, the method further comprises hydrating the mixture prior to the loading step. In a further aspect, hydrating is via the addition of water. In a still further aspect, hydrating is via the addition of an aqueous buffer.

In various aspects, the method further comprises removing the assisting molecule. In a further aspect, removing is via extraction. In a still further aspect, removing is via extraction with a solvent that is immiscible with water (e.g., hexane).

In various aspects, the method further comprises loading a cargo molecule as further described herein.

In various aspects, the method does not comprise a post-processing step as further described herein. Examples of post-processing steps include, but are not limited to, extrusion, sonication, or a combination thereof. In a further aspect, the method does not comprise a post-processing step prior to loading of the cargo molecule.

C. Unilamellar Liposomes

In one aspect, disclosed are unilamellar liposomes prepared by a disclosed method. Thus, in various aspects, disclosed are unilamellar liposomes comprising a mixture of a lipid, an assisting molecule, and a cargo molecule, wherein the mixture is loaded into a lipid bilayer. In a further aspect, disclosed are unilamellar liposomes comprising a mixture of a lipid and a cargo molecule, wherein the mixture is loaded into a lipid bilayer.

In various aspects, the disclosed unilamellar liposome comprise a lipid. Examples of lipids include, but are not limited to, phosphatidylcholines and phosphatidylserines. In a further aspect, the lipid is 1,2-dimyristoyl-sn-glycero-3-phosphocholine (DMPC), 1,2-dimyristoyl-sn-glycero-3-phospho-L-serine (DMPS), 1,2-dipalmitoyl-sn-glycero-3-phosphocholine (DPPC), 1,2-dipalmitoyl-sn-glycero-3-phospho-L-serine (DPPS), or a combination thereof. In a still further aspect, the lipid is 1,2-dimyristoyl-sn-glycero-3-phosphocholine (DMPC) DMPC with 1-10%; 1,2-dimyristoyl-sn-glycero-3-phospho-L-serine (sodium salt) (DMPS); 1,2-dipalmitoyl-sn-glycero-3-phosphocholine (DPPC) DPPC with 1-10%; 1,2-dipalmitoyl-sn-glycero-3-phospho-L-serine (sodium salt) (DPPS); and combinations thereof. It should be understood that these are non-exhaustive lists of lipids.

In various aspects, the disclosed unilamellar liposome comprises an assisting molecule. Without wishing to be bound by theory, an assisting molecule can serve a dual role: (1) synergistic formation of unilamellar liposomes with narrow size distribution; and (2) facilitation of loading of hydrophobic cargo molecules into the bilayers. In contrast with existing methods, cargo-loaded unilamellar liposomes are produced directly from the mixture of lipids with cargo and assisting molecules upon hydration with water or an aqueous buffer. Elimination of the extrusion step greatly simplifies the scale-up of the fabrication of cargo-loaded liposomes, which is essential for large-scale production. In addition, the use of assisting molecules facilitates incorporation of molecules into the bilayer that would be difficult to load using traditional methods. After the formation of unilamellar liposomes, assisting molecules can be removed by extraction using hexane or other organic solvent immiscible with water.

In a further aspect, the assisting molecule is a terpene such as, for example, a monoterpene. Examples of monoterpenes include, but are not limited to, limonene, geraniol, α-terpineol, thymol, menthol, carvone, eucalyptol, perillaldehyde, myrcene, mentho, carvone, hinokitiol, linalool, careen, sabinene, camphor, menthol, camphene, thujene, camphor, borneol, eucalyptol, and ascaridole. In a still further aspect, the monoterpene is selected from limonene and geraniol. In yet a further aspect, the monoterpene is limonene. In an even further aspect, the assisting molecule is limonene, geraniol, divinylbenzene, tert-butylstyrene, tert-butylmethacrylate, butylmethacrylate, 1,4-butanediol dimethacrylate, or a combination thereof. In exemplary embodiments, the assisting molecule may be selected from the group including, but not limited to, hydrocarbons, alcohols, esters, aldehydes, ketones, amines, halogenated compounds. It should be understood that these are non-exhaustive lists of molecules.

In various aspects, the molar ratio of the assisting molecule to the lipid is of from about 0.25:1 to about 10:1, about 0.25:1 to about 8:1, from about 0.25:1 to about 6:1, from about 0.25:1 to about 4:1, from about 0.25:1 to about 2:1, or from about 0.25:1 to about 1:1. In a further aspect, the molar ratio of the assisting molecule to the lipid is about 1:1.

In various aspects, the disclosed unilamellar liposome comprises a cargo molecule. Examples of cargo material includes, but is not limited to, Lutein, Zeaxantin, Violaxantin, Astaxantin, Carotene, Cilostazol, Cilostamide, or a combination thereof. In a further aspect, the cargo molecule is a nucleic acid such as, for example, deoxyribonucleic acid (DNA) or ribonucleic acid (RNA). In a still further aspect, the nucleic acid is DNA (e.g., complementary DNA or cDNA). In yet a further aspect, the nucleic acid is RNA (e.g., micro RNA or miRNA, messenger RNA or mRNA). It should be understood that these are non-exhaustive lists of molecules.

D. Pharmaceutical Compositions Comprising the Liposomes

In one aspect, disclosed are pharmaceutical compositions comprising an effective amount of a disclosed unilamellar liposome and a pharmaceutically acceptable carrier. In a further aspect, the unilamellar liposome was prepared by a disclosed method. In a still further aspect, the unilamellar liposome comprises a mixture of a lipid and a cargo molecule, wherein the mixture is loaded into a lipid bilayer.

In various aspects, the unilamellar liposome is prepared by (i) mixing a lipid, an assisting molecule, and a cargo molecule, thereby forming a mixture, (ii) loading the mixture into a lipid bilayer, and (iii) removing the assisting molecule. In a further aspect, the method further comprises hydrating the mixture prior to the loading step by, for example, adding water or an aqueous buffer. In a still further aspect, the method does not comprise a post-processing step (e.g., extrusion, sonication).

In a further aspect, the lipid bilayer does not contain limonene or cineole.

In various aspects, the molar ratio of the assisting molecule to the lipid is of from about 0.25:1 to about 10:1, about 0.25:1 to about 8:1, from about 0.25:1 to about 6:1, from about 0.25:1 to about 4:1, from about 0.25:1 to about 2:1, or from about 0.25:1 to about 1:1. In a further aspect, the molar ratio of the assisting molecule to the lipid is about 1:1.

Thus, in various aspects, the unilamellar liposomes and liposomal formulations of the invention can be administered in pharmaceutical compositions, which are formulated according to the intended method of administration. The unilamellar liposomes and liposomal formulations described herein can be formulated in a conventional manner using one or more physiologically acceptable carriers or excipients. For example, a pharmaceutical composition can be formulated for local or systemic administration, intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, PA 1990.

In various aspects, the disclosed pharmaceutical compositions comprise the disclosed unilamellar liposomes, which contain, inter alia, a cargo molecule (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a unilamellar liposome of the invention. The unilamellar liposomes, including the cargo molecule or a pharmaceutically acceptable salt thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to deliver a cargo molecule as further described herein.

In a further aspect, the pharmaceutical composition is used to induce an immune response as further described herein.

In various aspects, the composition is a solid dosage form. In a further aspect, the composition is an oral solid dosage form. In a still further aspect, the solid dosage form is a tablet. In yet a further aspect, the solid dosage form is a capsule.

It is understood that the disclosed compositions can be prepared from the disclosed unilamellar liposomes. It is also understood that the disclosed compositions can be employed in the disclosed methods of using.

E. Systems

In one aspect, disclosed are systems comprising: (a) a lipid; (b) an assisting molecule; and (c) a cargo molecule. Without wishing to be bound by theory, the disclosed system can be used for preparing a unilamellar liposome from a lipid loaded with an assisting molecule and a cargo material (e.g., hydrophobic cargo material), without the need for extrusion, sonication, or other methods for converting a multilamellar liposome into a unilamellar liposome. This process facilitates the solubilization of hydrophobic cargo materials in the bilayer and expands the effective loading capacity of the bilayer.

In various aspects, the lipid is a phosphatidylcholine or a phosphatidylserine. In a further aspect, the lipid is 1,2-dimyristoyl-sn-glycero-3-phosphocholine (DMPC), 1,2-dimyristoyl-sn-glycero-3-phospho-L-serine (DMPS), 1,2-dipalmitoyl-sn-glycero-3-phosphocholine (DPPC), 1,2-dipalmitoyl-sn-glycero-3-phospho-L-serine (DPPS), or a combination thereof. In a still further aspect, the lipid is 1,2-dimyristoyl-sn-glycero-3-phosphocholine (DMPC) DMPC with 1-10%; 1,2-dimyristoyl-sn-glycero-3-phospho-L-serine (sodium salt) (DMPS); 1,2-dipalmitoyl-sn-glycero-3-phosphocholine (DPPC) DPPC with 1-10%; 1,2-dipalmitoyl-sn-glycero-3-phospho-L-serine (sodium salt) (DPPS); and combinations thereof. It should be understood that these are non-exhaustive lists of lipids.

In various aspects, the assisting molecule is a terpene such as, for example, a monoterpene. In a further aspect, limonene, geraniol, α-terpineol, thymol, menthol, carvone, eucalyptol, perillaldehyde, myrcene, mentho, carvone, hinokitiol, linalool, careen, sabinene, camphor, menthol, camphene, thujene, camphor, borneol, eucalyptol, and ascaridole. In a still further aspect, the monoterpene is selected from limonene and geraniol. In yet a further aspect, the monoterpene is limonene. In an even further aspect, the assisting molecule is limonene, geraniol, divinylbenzene, tert-butylstyrene, tert-butylmethacrylate, butylmethacrylate, 1,4-butanediol dimethacrylate, or a combination thereof. In exemplary embodiments, the assisting molecule may be selected from the group including, but not limited to, hydrocarbons, alcohols, esters, aldehydes, ketones, amines, halogenated compounds. It should be understood that these are non-exhaustive lists of molecules.

In various aspects, the cargo material is Lutein, Zeaxantin, Violaxantin, Astaxantin, Carotene, Cilostazol, Cilostamide, or a combination thereof. In a further aspect, the cargo molecule is a nucleic acid such as, for example, deoxyribonucleic acid (DNA) or ribonucleic acid (RNA). In a still further aspect, the nucleic acid is DNA (e.g., complementary DNA or cDNA). In yet a further aspect, the nucleic acid is RNA (e.g., micro RNA or miRNA, messenger RNA or mRNA). It should be understood that these are non-exhaustive lists of molecules.

In various aspects, the disclosed system can be useful in a disclosed method of making.

F. Methods of Using the Unilamellar Liposomes

The unilamellar liposomes of the invention are useful in delivering cargo molecules and also in inducing an immune response as further described herein. To deliver the cargo molecule and/or to induce the immune response, the formulations are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the liposomes or compositions, the subject can be diagnosed with a disease or disorder for which gene therapy is believed to be beneficial.

The formulations can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a disease or disorder for which gene therapy if believed to be beneficial (e.g., cancer, cystic fibrosis, heart disease, diabetes, hemophilia, acquired immunodeficiency syndrome (AIDS), inherited retinal dystrophy, or spinal muscular atrophy) or administration to provoke an immune response in a subject (e.g., a subject at risk of developing a disease or disorder such as, for example, a viral infection).

The therapeutically effective amount or dosage of the formulation (or of the liposome within the formulation) can vary within wide limits. Such a dosage is adjusted to the individual requirements in each particular case including the specific liposomal formulation(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the liposome or the composition to make up the daily dose. The dosage can be adjusted by the individual physician in the event of any contraindications. Dosage can vary, and can be administered in one or more dose administrations daily, for one or several days.

1. Delivering a Cargo Molecule

In one aspect, disclosed are methods of delivering a cargo molecule to a subject in need thereof, the method comprising administering to the subject an effective amount of a disclosed unilamellar liposome. In a further aspect, the unilamellar liposome can be prepared by a disclosed method. Thus, in various aspects, the unilamellar liposome is prepared by (i) mixing a lipid, an assisting molecule, and a cargo molecule, thereby forming a mixture, (ii) loading the mixture into a lipid bilayer, and (iii) removing the assisting molecule. In a further aspect, the method further comprises hydrating the mixture prior to the loading step by, for example, adding water or an aqueous buffer. In a still further aspect, the method does not comprise a post-processing step (e.g., extrusion, sonication).

In a further aspect, the subject has been diagnosed with a need for gene therapy prior to the administering step. In a still further aspect, the subject has been diagnosed as having a disease for which gene therapy can be beneficial such as, for example, cancer, cystic fibrosis, heart disease, diabetes, hemophilia, acquired immunodeficiency syndrome (AIDS), inherited retinal dystrophy, or spinal muscular atrophy. In yet a further aspect, the disease is cancer, cystic fibrosis, heart disease, diabetes, hemophilia, or acquired immunodeficiency syndrome (AIDS). In an even further aspect, the disease is inherited retinal dystrophy. In a still further aspect, the disease is spinal muscular atrophy.

In a further aspect, the subject is a mammal. In a still further aspect, the mammal is a human.

In a further aspect, the method further comprises the step of identifying a subject in need of gene therapy.

In a further aspect, administering is topical, oral, intranasal, intramuscular, or subcutaneous administration. In a still further aspect, administering is systemic administration. In yet a further aspect, administering is oral administration.

In a further aspect, the effective amount is a therapeutically effective amount. In a still further aspect, the effective amount is a prophylactically effective amount.

In a further aspect, the disease or disorder is a genetic disorder.

2. Inducing an Immune Response

In one aspect, disclosed are methods of inducing an immune response in a subject in need thereof, the method comprising administering to the subject an effective amount of a disclosed unilamellar liposome. In a further aspect, the unilamellar liposome can be prepared by a disclosed method. Thus, in various aspects, the unilamellar liposome is prepared by (i) mixing a lipid, an assisting molecule, and a cargo molecule, thereby forming a mixture, (ii) loading the mixture into a lipid bilayer, and (iii) removing the assisting molecule. In a further aspect, the method further comprises hydrating the mixture prior to the loading step by, for example, adding water or an aqueous buffer. In a still further aspect, the method does not comprise a post-processing step (e.g., extrusion, sonication).

In a further aspect, the immune response is against a viral infection. Examples of viral infections include, but are not limited to, human immunodeficiency virus (HIV), human papillomavirus (HPV), herpes simplex virus (HSV), human cytomegalovirus (HCMV), chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, Chikungunya virus (CHIKV), Venezuelan equine encephalitis (VEEV), dengue (DENY), influenza, West Nile virus (WNV), human coronavirus, and zika (ZIKV). In a still further aspect, the viral infection is human immunodeficiency virus (HIV). In yet a further aspect, the viral infection is a coronavirus such as, for example, Middle East respiratory syndrome (MERS), severe acute respiratory syndrome (SARS), and severe acute respiratory syndrome coronavirus 2 (SARS-CoV-2). In an even further aspect, the viral infection is SARS-CoV-2.

In a further aspect, the subject is a mammal. In a still further aspect, the mammal is a human.

In a further aspect, the method further comprises the step of identifying a subject in need of immunity or partial immunity against an infection (e.g., from a virus).

In a further aspect, administering is topical, oral, intranasal, intramuscular, or subcutaneous administration. In a still further aspect, administering is systemic administration. In yet a further aspect, administering is oral administration.

In a further aspect, the effective amount is a therapeutically effective amount. In a still further aspect, the effective amount is a prophylactically effective amount.

3. Use of Compounds

In one aspect, the invention relates to the use of a disclosed unilamellar liposome. In a further aspect, a use relates to the manufacture of a medicament for gene therapy and/or for inducing an immune response in a subject.

In a further aspect, the use relates to a process for preparing a disclosed unilamellar liposome for use as a medicament.

In a further aspect, the use related to a method of preparing liposomal formulations as further described here. For example, in various aspects, the method includes preparing a lipid solution including a lipid, an assisting molecule, and a cargo molecule and forming a lipid cake. The lipid cake may then be hydrated with a first aqueous media. The hydrated cake may be mixed in a mixer and subjected to one or more freeze/thaw cycles before removal of the assisting molecule. Importantly, cargo-loaded unilamellar liposomes are produced directly from the mixture of lipids with cargo and assisting molecules upon hydration with water or an aqueous buffer. Elimination of the extrusion step greatly simplifies the scale-up of the fabrication of cargo-loaded liposomes, which is essential for large-scale production. In addition, the use of assisting molecules facilitates incorporation of molecules into the bilayer that would be difficult to load using traditional methods.

In one aspect, the use is characterized in that the subject is a human.

In various aspects, the use relates to gene therapy (i.e., the use relates to treatment of a disease or disorder for which gene therapy can be beneficial).

In various aspects, the use relates to inducing an immune response such as, for example, an immune response against a viral infection. In one aspect, the use is characterized in that the viral infection is human immunodeficiency virus (HIV), human papillomavirus (HPV), herpes simplex virus (HSV), human cytomegalovirus (HCMV), chicken pox, infectious mononucleosis, mumps, measles, rubella, shingles, ebola, viral gastroenteritis, viral hepatitis, viral meningitis, human metapneumovirus, human parainfluenza virus type 1, parainfluenza virus type 2, parainfluenza virus type 3, respiratory syncytial virus, viral pneumonia, Chikungunya virus (CHIKV), Venezuelan equine encephalitis (VEEV), dengue (DENV), influenza, West Nile virus (WNV), human coronavirus, or zika (ZIKV). In one aspect, the use is characterized in that the viral infection is SARS-CoV-2.

In a further aspect, the use relates to the manufacture of a medicament for gene therapy and/or inducing an immune response in a subject.

It is understood that the disclosed uses can be employed in connection with the disclosed compounds, formulations, products of disclosed methods of making, methods, and kits. In a further aspect, the invention relates to the use of a disclosed formulation or a disclosed product in the manufacture of a medicament for use in gene therapy and/or for inducing an immune response in a mammal.

4. Manufacture of a Medicament

In one aspect, the invention relates to a method for the manufacture of a medicament for use in gene therapy and/or for inducing an immune response in a subject in need thereof, the method comprising combining a formulation comprising a therapeutically effective amount of a disclosed liposome, or product of a disclosed method, with a pharmaceutically acceptable carrier or diluent.

As regards these applications, the present method includes the administration to an animal, particularly a mammal, and more particularly a human, of a formulation comprising a therapeutically effective amount of the liposome for use in gene therapy and/or for inducing an immune response. The dose administered to an animal, particularly a human, in the context of the present invention should be sufficient to affect a therapeutic response in the animal over a reasonable time-frame. One skilled in the art will recognize that dosage will depend upon a variety of factors including the condition of the animal and the body weight of the animal.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing, and frequency of administration as well as the existence, nature, and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed liposome, formulation, or a product of a disclosed method of making, or a pharmaceutically acceptable salt, solvate, or polymorph thereof, with a pharmaceutically acceptable carrier or diluent.

G. REFERENCES

All documents cited herein and any below-listed documents, which are attached hereto for submission with this provisional patent application, all referenced publications cited therein, and the descriptions and information contained in these documents are expressly incorporated herein in their entirety to the same extent as if each document or cited publication/patent document was individually and expressly incorporated herein:

1. Bernstein, P.S.; Li, B.; Vachali, P.P.; Gorusupudi, A.; Shyam, R.; Henriksen, B.S.; Nolan, J.M. Lutein, zeaxanthin, and meso-zeaxanthin: The basic and clinical science underlying carotenoid-based nutritional interventions against ocular disease. *Prog. Retin. Eye Res.* 2016, 50, 34-66, doi:10.1016/j.preteyeres.2015.10.003.
2. Nolan, J.M.; Mulcahy, R.; Power, R.; Moran, R.; Howard, A.N. Nutritional Intervention to Prevent Alzheimer's Disease: Potential Benefits of Xanthophyll Carotenoids and Omega-3 Fatty Acids Combined. *J. Alzheimer's Dis.* 2018, 64, 367-378, doi:10.3233/jad-180160.
3. Bone, A.R.; Landrum, J.T.; Fernandez, L.; Tarsis, S.L. Analysis of the macular pigment by HPLC: Retinal distribution and age study. *Investig. Ophthalmol. Vis. Sci.* 1988, 29, 843-849.
4. Johnson, E.J.; Vishwanathan, R.; Johnson, M.A.; Hausman, D.B.; Davey, A.; Scott, T.M.; Green, R.C.; Miller, L.S.; Gearing, M.; Woodard, J.; et al. Relationship between Serum and Brain Carotenoids, alpha-Tocopherol, and Retinol Concentrations and Cognitive Performance in the Oldest Old from the Georgia Centenarian Study. *J. Aging Res.* 2013, 2013, 951786.
5. Rapp, L.M.; Maple, S.S.; Choi, J.H. Lutein and zeaxanthin concentrations in rod outer segment membranes from perifoveal and peripheral human retina. *Investig. Ophthalmol. Vis. Sci.* 2000, 41, 1200-1209.
6. Widomska, J.; Subczynski, W.K. Mechanisms enhancing the protective functions of macular xanthophylls in the retina during oxidative stress. *Exp. Eye Res.* 2019, 178, 238-246, doi:10.1016/j.exer.2018.06.012.
7. Grudzinski, W.; Nierzwicki, L.; Welc, R.; Reszczynska, E.; Luchowski, R.; Czub, J.; Gruszecki, W.I. Localization and Orientation of Xanthophylls in a Lipid Bilayer. *Sci. Rep.* 2017, 7, 1-10, doi:10.1038/s41598-017-10183-7.
8. Gruszecki, W.I.; Strzalka, K. Carotenoids as modulators of lipid membrane physical properties. *Biochim. Biophys. Acta (BBA)-Mol. Basis Dis.* 2005, 1740, 108-115, doi:10.1016/j.bbadis.2004.11.015.
9. Widomska, J.; Zareba, M.; Subczynski, W.K. Can Xanthophyll-Membrane Interactions Explain Their Selective Presence in the Retina and Brain? *Foods* 2016, 5, 7, doi:10.3390/foods5010007.
10. Delmelle, M. An Investigation of Retinal as a Source of Singlet Oxygen. *Photochem. Photobiol.* 1978, 27, 731-734, doi:10.1111/j.1751-1097.1978.tb07671.x.
11. Kim, S.R.; Nakanishi, K.; Itagaki, Y.; Sparrow, J.R. Photooxidation of A2-PE, a photoreceptor outer segment fluorophore, and pro-tection by lutein and zeaxanthin. *Exp. Eye Res.* 2006, 82, 828-839.

12. Mortensen, A.; Skibsted, L.H. Free radical transients in photobleaching of xanthophylls and carotenes. *Free Radic. Res.* 1997, 26, 549-563, doi:10.3109/10715769709097826.
13. Adams, D.B.; Pozo, L.M.; Stewart, J.J.; Adams, W.W., 3rd. Zeaxanthin and Lutein: Photoprotectors, Anti-Inflammatories, and Brain Food. *Molecules* 2020, 25, 3607.
14. Connor, W.E.; Duell, P.B.; Kean, R.; Wang, Y. The Prime Role of HDL to Transport Lutein into the Retina: Evidence from HDL-Deficient WHAM Chicks Having a Mutant ABCA1 Transporter. *Investig. Opthalmology Vis. Sci.* 2007, 48, 4226-4231, doi:10.1167/iovs.06-1275.
15. Loane, E.; Nolan, J.M.; Donovan, 0.0.; Bhosale, P.; Bernstein, P.S.; Beatty, S. Transport and Retinal Capture of Lutein and Zeaxanthin with Reference to Age-related Macular Degeneration. *Surv. Ophthalmol.* 2008, 53, 68-81, doi:10.1016/j.survophthal.2007.10.008.
16. Li, B.; Vachali, P.; Frederick, J.M.; Bernstein, P.S. Identification of StARD3 as a Lutein-Binding Protein in the Macula of the Primate Retina. *Biochemistry* 2011, 50, 2541-2549, doi:10.1021/bi101906y.
17. Thomas, L.D.; Bandara, S.; Parmar, V.M.; Srinivasagan, R.; Khadka, N.; Golczak, M.; Kiser, P.D.; von Lintig, J. The human mitochondrial enzyme BCO2 exhibits catalytic activity toward carotenoids and apocarotenoids. *J. Biol. Chem.* 2020, 295, 15553-15565, doi:10.1074/jbc.ra120.015515.
18. Kiefer, C.; Hessel, S.; Lampert, J.M.; Vogt, K.; Lederer, M.O.; Breithaupt, D.E.; Von Lintig, J. Identification and Characterization of a Mammalian Enzyme Catalyzing the Asymmetric Oxidative Cleavage of Provitamin A. *J. Biol. Chem.* 2001, 276, 14110-14116, doi:10.1074/jbc.m011510200.
19. Amengual, J.; Lobo, G.P.; Golczak, M.; Li, H.N.M.; Klimova, T.; Hoppel, C.L.; Wyss, A.; Palczewski, K.; Von Lintig, J. A mitochondrial enzyme degrades carotenoids and protects against oxidative stress. *FASEB J.* 2010, 25, 948-959, doi:10.1096/fj.10-173906.
20. Lobo, G.P.; Isken, A.; Hoff, S.; Babino, D.; Von Lintig, J. BCDO2 acts as a carotenoid scavenger and gatekeeper for the mitochondrial apoptotic pathway. *Development* 2012, 139, 2966-2977, doi:10.1242/dev.079632.
21. Palczewski, G.; Amengual, J.; Hoppel, C.L.; Von Lintig, J. Evidence for compartmentalization of mammalian carotenoid metabolism. *FASEB J.* 2014, 28, 4457-4469, doi:10.1096/fj.14-252411.
22. Lindqvist, A.; He, Y.G.; Andersson, S. Cell type-specific expression of beta-carotene 9',10'-monooxygenase in human tissues. *J. Histochem. Cytochem.* 2005, 53, 1403-1412.
23. Wu, L.; Guo, X.; Wang, W.; Medeiros, D.M.; Clarke, S.L.; Lucas, E.A.; Smith, B.J.; Lin, D. Molecular aspects of beta, beta-carotene-9',10'-oxygenase 2 in carotenoid metabolism and diseases. *Exp. Biol. Med.* 2016, 241, 1879-1887.
24. Vage, I.D.; A Boman, I. A nonsense mutation in the beta-carotene oxygenase 2 (BCO2) gene is tightly associated with accumulation of carotenoids in adipose tissue in sheep (Ovis aries). *BMC Genet.* 2010, 11, 10, doi:10.1186/1471-2156-11-10.
25. Berry, S.D.; Davis, S.R.; Beattie, E.M.; Thomas, N.L.; Burrett, A.K.; Ward, H.E.; Stanfield, A.M.; Biswas, M.; Udy, A.A.E.; Oxley, P.E.; et al. Mutation in bovine beta-carotene oxygenase 2 affects milk color. *Genetics* 2009, 182, 923-926.
26. Eriksson, J.; Larson, G.; Gunnarsson, U.; Bed'hom, B.; Boichard, T.M.; Stromstedt, L.; Wright, D.; Jungerius, A.; Vereijken, A.; Randi, E.; et al. Identification of the yellow skin gene reveals a hybrid origin of the domestic chicken. *PLoS Genet.* 2008, 4, doi:10.1371/journal.pgen.1000010.
27. Meyers, K.J.; Mares, J.A.; Igo, R.P.; Truitt, B.; Liu, Z.; Millen, A.E.; Klein, M.L.; Johnson, E.J.; Engelman, C.D.; Karki, C.K.; et al. Genetic Evidence for Role of Carotenoids in Age-Related Macular Degeneration in the Carotenoids in Age-Related Eye Disease Study (CAREDS). *Investig. Opthalmology Vis. Sci.* 2014, 55, 587-599, doi:10.1167/iovs.13-13216.
28. Guo, X.; Wu, L.; Lyu, Y.; Chowanadisai, W.; Clarke, S.L.; Lucas, E.A.; Smith, B.J.; He, H.; Wang, W.; Medeiros, D.M.; et al. Ablation of be-ta,beta-carotene-9',10'-oxygenase 2 remodels the hypothalamic metabolome leading to metabolic disorders in mice. *J. Nutr. Biochem.* 2017, 46, 74-82.
29. Babino, D.; Palczewski, G.; Adhi, W.M.A.; Kiser, P.D.; Golczak, M.; von Lintig, J. Characterization of the Role of beta-Carotene 9,10-Dioxygenase in Macular Pigment Metabolism. *J. Biol. Chem.* 2015, 290, 24844-24857.
30. Li, B.; Vachali, P.P.; Gorusupudi, A.; Shen, Z.; Sharifzadeh, H.; Besch, B.M.; Nelson, K.; Horvath, M.M.; Frederick, J.M.; Baehr, W. Inactivity of human beta,beta-carotene-9',10'-dioxygenase (BCO2) underlies retinal accumulation of the human macular carotenoid pigment. *Proc. Natl. Acad. Sci. USA* 2014, 111, 10173-10178.
31. Poliakov, E.; Soucy, J.; Gentleman, S.; Rogozin, LB.; Redmond, T.M. Phylogenetic analysis of the metazoan carotenoid oxygenase superfamily: A new ancestral gene assemblage of BCO-like (BCOL) proteins. *Sci. Rep.* 2017, 7, 3192, doi:10.1038/s41598-017-13521-x.
32. Dergunov, S.A.; Bowles, E.A.; Gordon, W.R.; Green, M.; Bierman, A.; Ellsworth, M.L.; Pinkhassik, E.; Sprague, R.S. Liposomal delivery of a phosphodiesterase 3 inhibitor rescues low oxygen-induced ATP release from erythrocytes of humans with type 2 diabetes. *Biochem. Biophys. Rep.* 2015, 2, 137-142, doi:10.1016/j.bbrep.2015.05.011.
33. Scott, H.L.; Skinkle, A.; Kelley, E.G.; Waxham, M.N.; Levental, I.; Heberle, F.A. On the Mechanism of Bilayer Separation by Extrusion, or Why Your LUVs Are Not Really Unilamellar. *Biophys. J.* 2019, 117, 1381-1386, doi:10.1016/j.bpj.2019.09.006.
34. Uppal, S.; Rogozin, LB.; Redmond, T.; Poliakov, E. Palmitoylation of Metazoan Carotenoid Oxygenases. *Mol.* 2020, 25, 1942, doi:10.3390/molecules25081942.
35. Redmond, T.M.; Poliakov, E.; Yu, S.; Tsai, J.-Y.; Lu, Z.; Gentleman, S. Mutation of key residues of RPE65 abolishes its enzymatic role as isomerohydrolase in the visual cycle. *Proc. Natl. Acad. Sci. USA* 2005, 102, 13658-13663, doi:10.1073/pnas.0504167102.
36. Uppal, S.; Liu, T.; Poliakov, E.; Gentleman, S.; Redmond, T.M. The dual roles of RPE65 S-palmitoylation in membrane association and visual cycle function. *Sci. Rep.* 2019, 9, 5218, doi:10.1038/s41598-019-41501-w.
37. Waterhouse, A.; Bertoni, M.; Bienert, S.; Studer, G.; Tauriello, G.; Gumienny, R.; Heer, F.T.; de Beer, T.AP.; Rempfer, C.; Bordoli, L.; et al. SWISS-MODEL:

Homology modelling of protein structures and complexes. *Nucleic Acids Res.* 2018, 46, W296-W303, doi:10.1093/nar/gky427.
38. Roy, A.; Kucukural, A.; Zhang, Y. I-TASSER: A unified platform for automated protein structure and function prediction. *Nat. Protoc.* 2010, 5, 725-738, doi:10.1038/nprot.2010.5.
39. Roy, A.; Yang, J.; Zhang, Y. COFACTOR: An accurate comparative algorithm for structure-based protein function annotation. *Nucleic Acids Res.* 2012, 40, W471-W477, doi:10.1093/nar/gks372.
40. Zhang, Y. I-TASSER server for protein 3D structure prediction. *BMC Bioinform.* 2008, 9, 1-8, doi:10.1186/1471-2105-9-40.
41. Trott, O.; Olson, A.J. AutoDock Vina: Improving the speed and accuracy of docking with a new scoring function, efficient op-timization, and multithreading. *J. Comput. Chem.* 2010, 31, 455-461.
42. Lazrak, T.; Milon, A.; Wolff, G.; Albrecht, A.M.; Miehe, M.; Ourisson, G.; Nakatani, Y. Comparison of the effects of inserted C40- and C50-terminally dihydroxylated carotenoids on the mechanical properties of various phospholipid vesicles. *Biochim. Biophys. Acta (BBA) Biomembr.* 1987, 903, 132-141, doi:10.1016/0005-2736(87)90163-5.
43. Nacke, C.; Schrader, J. Liposome based solubilisation of carotenoid substrates for enzymatic conversion in aqueous media. *J. Mol. Catal. B: Enzym.* 2011, 71, 133-138, doi:10.1016/j.molcatb.2011.04.009.
44. Socaciu, C.; Jessel, R.; A Diehl, H. Carotenoid incorporation into microsomes: Yields, stability and membrane dynamics. *Spectrochim. Acta Part A: Mol. Biomol. Spectrosc.* 2000, 56, 2799-2809, doi:10.1016/s1386-1425(00)00375-9.
45. Strzalka K, Gruszecki WI: Effect of β-carotene on structural and dynamic properties of model phosphatidylcholine membranes. I. An EPR spin label study. Biochimica et Biophysica Acta (BBA) *Biomembranes* 1994, 1194, 138-142.
46. Chakraborty, S.; Doktorova, M.; Molugu, T.R.; Heberle, F.A.; Scott, H.L.; Dzikovski, B.; Nagao, M.; Stingaciu, L.-R.; Standaert, R.F.; Barrera, F.N.; et al. How cholesterol stiffens unsaturated lipid membranes. *Proc. Natl. Acad. Sci. USA* 2020, 117, 21896-21905, doi:10.1073/pnas.2004807117.
47. Milon, A.; Ourisson, G.; Nakatani, Y. Organization of Carotenoid-Phospholipid Bilayer Systems. Incorporation of Zeaxanthin, Astaxanthin, and their C50 Homologues into Dimyristoylphosphatidylcholine Vesicles. *Helv. Chim. Acta* 1986, 69, 12-24, doi:10.1002/hlca.19860690104.
48. Dela Sena, C.; Sun, J.; Narayanasamy, S.; Riedl, KM.; Yuan, Y.; Curley, R.W., Jr.; Schwartz, S.J.; Harrison, E.H. Substrate Specificity of Purified Recombinant Chicken beta-Carotene 9',10'-Oxygenase (BCO2). *J. Biol. Chem.* 2016, 291, 14609-14619.
49. Babino, D.; Golczak, M.; Kiser, P.D.; Wyss, A.; Palczewski, K.; von Lintig, J. The Biochemical Basis of Vitamin A3 Production in Ar-thropod Vision. *ACS Chem. Biol.* 2016, 11, 1049-1057.
50. Frede, K.; Ebert, F.; Kipp, A.P.; Schwerdtle, T.; Baldermann, S. Lutein Activates the Transcription FactorNrf2in Human Retinal Pigment Epithelial Cells. *J. Agric. Food Chem.* 2017, 65, 5944-5952, doi:10.1021/acs.jafc.7b01929.
51. Saadatmandi, B.C.; Rimbach, G.; Jungblut, A.; Frank, J. Comparison of tetrahydrofuran, fetal calf serum, and Tween 40 for the delivery of astaxanthin and canthaxanthin to HepG2 cells. *Cytotechnology* 2010, 63, 89-97, doi:10.1007/s10616-010-9324-7.
52. During, A.; Doraiswamy, S.; Harrison, E.H. Xanthophylls are preferentially taken up compared with beta-carotene by retinal cells via a SRBI-dependent mechanism. *J. Lipid Res.* 2008, 49, 1715-1724.
53. Semeniuk, C.E.; Wolczynski, S. Identification of carotenoids in ovarian tissue in women. *Oncol. Rep.* 2005, 14, 1385-1392, doi:10.3892/or.14.5.1385.
54. Perlman, M.J.A.; Millen, A.E.; Ficek, T.L.; Hankinson, S.E. The body of evidence to support a protective role for lutein and ze-axanthin in delaying chronic disease. Overview. *J. Nutr.* 2002, 132, 518S-524S.
55. Li, R.; Turner, S.D.; Brautigan, D.L. Xanthophylls lutein and zeaxanthin modify gene expression and induce synthesis of hyaluronan in keratinocyte model of human skin. *Biochem. Biophys. Rep.* 2015, 4, 52-58, doi:10.1016/j.bbrep.2015.08.012.
56. Eroglu, A.; Hruszkewycz, D.P.; Curley, R.W.; Harrison, E.H., Jr. The eccentric cleavage product of beta-carotene, be-ta-apo-13-carotenone, functions as an antagonist of RXRalpha. *Arch. Biochem. Biophys.* 2010, 504, 11-16.
57. Eroglu, A.; Hruszkewycz, D.P.; dela Sena, C.; Narayanasamy, S.; Riedl, K.M.; Kopec, R.E.; Schwartz, S.J.; Curley, R.W., Jr.; Harrison, E.H. Naturally occurring eccentric cleavage products of provitamin A beta-carotene function as antagonists of retinoic acid receptors. *J. Biol. Chem.* 2012, 287, 15886-15895.
58. Wang, C.X.; Jiang, H.; Yuen, J.J.; Lee, S.A.; Narayanasamy, S.; Curley, R.W., Jr.; Harrison, E.H.; Blaner, W.S.: Actions of beta-apo-carotenoids in differentiating cells: Differential effects in P19 cells and 3T3-L1 adipocytes. *Arch. Biochem. Biophys.* 2015, 572, 2-10.
59. Ziouzenkova, O.; Orasanu, G.; Sukhova, G.; Lau, E.; Berger, J.P.; Tang, G.; Krinsky, N.I.; Dolnikowski, G.G.; Plutzky, J. Asymmetric cleavage of beta-carotene yields a transcriptional repressor of retinoid X receptor and peroxisome proliferator-activated receptor responses. *Mol. Endocrinol.* 2007, 21, 77-88.
60. Shivarudrappa, A.H.; Ponesakki, G. Lutein reverses hyperglycemia-mediated blockage of Nrf2 translocation by modulating the activation of intracellular protein kinases in retinal pigment epithelial (ARPE-19) cells. *J. Cell Commun. Signal.* 2019, 14, 207-221, doi:10.1007/s12079-019-00539-1.

While the invention has been described with reference to preferred embodiments, it will be understood by those skilled in the art that various changes may be made and equivalents may be substituted for the elements thereof without departing from the scope of the invention. In addition, many modifications may be made to adapt the teaching of the invention to particular use, application, manufacturing conditions, use conditions, composition, medium, size, and/or materials without departing from the essential scope and spirit of the invention. Therefore, it is intended that the invention is not limited to the exemplary embodiments and best mode contemplated for carrying out this invention as described herein. Since many modifications, variations, and changes in detail can be made to the described examples, it is intended that all matters in the preceding description and shown in the accompanying figures be interpreted as illustrative and not in a limiting sense.

H. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Production of Large Unilamellar Vesicle-Based Nanocarriers and Demonstration of Successful Delivery of Xanthophylls Into Cells Most consideration of the antioxidant function of xanthophylls, polar hydroxy carotenoids, has focused on their chemical role in quenching excited triplet states of singlet oxygen by virtue of their extended conjugated bond systems. However, there is emerging evidence for a role of xanthophyll/xanthophyll cleavage products in modulating transcriptional regulation of antioxidant gene pathways.

In respect of their best-known role, high dietary intake of xanthophylls may offer protection against age-related macular degeneration (AMD), cancer and neurodegenerative diseases [1, 2]. While xanthophylls account for less than 20% of the total carotenoids in the human diet, in the blood plasma the amount of xanthophylls increases to about 40% and is increased even more in the brain and retina [3, 4]. Thus, xanthophylls account for about 70% of total carotenoids in all brain regions. Xanthophylls are selectively concentrated in the most vulnerable regions of polyunsaturated lipid-enriched membranes, such as in the retinal photoreceptor outer segments [5]. This localization is ideal for macular xanthophylls to act as lipid-soluble antioxidants, which is the most likely mechanism of protection against photooxidation [6]. Additionally, the high membrane solubility and preferential transmembrane orientation of macular xanthophylls [6,7] enhance their chemical and physical stability in retina and brain membranes [8] and maximize their protective action against oxidative stress in these organs [9]. Xanthophylls are capable of quenching excited triplet states of potent singlet oxygen photosensitizers. Free all-trans-retinal may absorb light and transfer energy from its excited triplet state to molecular oxygen, generating singlet oxygen [10]. It is postulated that the close proximity of xanthophylls allows effective energy transfer from excited all-trans-retinal to xanthophyll and prevents singlet oxygen generation by this photosensitizer [11]. By this mechanism, the largest part of excess energy can be transferred from potentially harmful triplets of photosensitizers to xanthophylls and dissipated as heat. The ratio of zeaxanthin (and meso-zeaxanthin) to lutein is higher in the macula where the strongest light is received compared to peripheral low-light-vision regions of the eye [3]. A portion of dietary lutein is converted to meso-zeaxanthin, a stereoisomer of zeaxanthin, presumably in retinal pigment epithelium (RPE) by RPE65 isomerase [12]. This preference for zeaxanthin has been suggested to be due to a greater antioxidant capacity, possibly due to the longer system of conjugated double bonds and membrane-stabilizing function of zeaxanthin (and meso-zeaxanthin) compared to lutein [12,13]. Xanthophylls are delivered to the retina with the help of high-density lipoprotein (HDL) [14] and xanthophyll-binding proteins [15]. Xanthophyll-binding proteins have been described for both zeaxanthin and lutein [16]. However, the role of β-carotene oxygenase 2 (BCO2), an enzyme that can cleave xanthophylls [17], is not thoroughly studied.

BCO2 is present in the brain, retina and RPE; everywhere xanthophylls accumulate. BCO2 is well characterized as a carotenoid metabolizing enzyme [18-21] that is widely distributed in tissues, including the retina, RPE, skeletal muscle, small intestine and liver [22]. A deficiency of BCO2 was found to be associated with accumulation of carotenoids in the adipose tissues [23], such as subcutaneous adipose tissue. This leads to the occurrence of yellow fat in sheep [24], cow [25], and yellow skin in chicken [26]. The abSNP rs2250417 in BCO2 has one of the strongest instances of statistical significance for association with AMD of carotenoid metabolism genes [27]. The two minor alleles for SNP rs2250417 in BCO2 account for an increase in risk for AMD by almost 50% [27]. Additionally, BCO2 deficiency in mice leads to stimulation of oxidative stress and inflammation in hypothalamic tissues on a low carotenoid diet [28].

To better study the role of BCO2 in metabolism of xanthophylls, xanthophyll-containing large unilamellar vesicles (LUVs) were developed to efficiently deliver xanthophylls to cells. mBCO2 in human cell culture was chosen to be expressed because it has only one major isoform while human and monkey BCO2 have several major isoforms. Only one of these has a N-terminal mitochondrial signal and it is still hotly debated if this isoform manifests as an active BCO2 enzyme [17, 29-31]. Here, using LUVs, lutein modulates the palmitoylation status of mouse BCO2 (mBCO2) and changes its cellular localization in HEK293F cells from mitochondria to nucleus upon binding. The same effect has been detected for zeaxanthin and violaxanthin but to a lesser degree, and the modeling analysis suggests a possible explanation of the difference. Accumulation in the nucleus of mBCO2 loaded with xanthophylls could directly affect gene expression and may provide a mechanism whereby xanthophylls/xanthophyll cleavage products could elicit a transcriptional response to oxidant stress.

a. Methods and Materials (a) Materials 1,2-dimyristoyl-sn-glycero-3-phosphocholine (DMPC), 1,2-dimyristoyl-sn-glycero-3-phospho-L-serine (sodium salt) (DMPS), 1,2-dipalmitoyl-sn-glycero-3-phosphocholine (DPPC), 1,2-dipalmitoyl-sn-glycero-3-phospho-L-serine (sodium salt) (DPPS) were purchased from Avanti Polar Lipids, Inc. (Alabaster, AL, USA). (R)-(+)-limonene and tricine were used as received (Sigma-Aldrich, St. Louis, MO, USA). Nitrogen-purged hexane, dichloromethane (DCM) and chloroform ($CHCl_3$) were passed through an activated alumina column, dried with $CaSO_4$, and stored over 4 Å molecular sieves. All kinetic experiments were performed with the same batch of samples. Lutein and violaxanthin were purchased from Cayman Chemicals (Ann Arbor, MI, USA), and zeaxanthin (65%) from Toronto Research Chemicals (Toronto, ON, Canada).

(b) Preparation of Large Unilamellar Vesicles (LUVS) With Xanthophylls

Aqueous lipid dispersions of LUVs were prepared by first mixing the required amounts of lipids, carotenoids, and limonene (used here for better solubilization of carotenoids in the lipid bilayer) in chloroform. All samples were prepared using similar protocol to the one described previously [32]. Amounts of lipids were the same, 10 mg/mL, limonene: lipid=1:1 (mol/mol), while amounts of carotenoids were different: 0.5 mg zeaxanthin in 1.5 mL of buffer (using DPPC/DPPS or DMPC/DMPS lipids); the lutein preparation contained 0.25 mg lutein in 1.5 mL of buffer (using DMPC/DMPS lipids); and the violaxanthin preparation contained 0.25 mg violaxanthin in 1.5 mL of buffer (using DMPC/DMPS lipids). All samples were prepared with a mole fraction of 7% PS (sn-glycero-3-phospho-L-serine) to avoid multilamellar stack formation [33]. The solvent was evaporated with an inert gas stream to constant weight. The lipid film was hydrated with 100 mM tricine-KOH pH 8.0 buffer (prepared with $H_2O$) at room temperature with intermittent gentle vortex mixing. The lipid suspension was passed through 0.4, 0.2, 0.1 μm Nucleopore polycarbonate membranes (21 times through each membrane) using a mini-extruder (Avanti Polar Lipids). The LUVs were mixed with hexane and shaken gently for 20 min to remove limonene as confirmed by GC-MS. The LUVs were then decanted from the organic layer and the aqueous solution was purged with nitrogen and degassed to remove traces of hexane.

(c) Generation of Expression Vectors

Mouse BCO2 cDNAs were prepared as described and used to generate vectors for the expression of BCO2 in mammalian cells. Briefly, BCO2 was subcloned into the bicistronic expression vector pVitro2 (InvivoGen, San Diego, CA, USA) and into the Gateway cloning vector pcDNA6.2c-Lumio-DEST vector (Thermo Fisher (Invitrogen), Carlsbad, CA, USA) to generate untagged or C-terminal V5/lumio tagged versions of mouse BCO2, respectively. All constructs and mutants were sequenced to verify the orientation and accuracy of the ORFs and/or the changes introduced.

(d) Cell Culture

Human 293F FreeStyle (Thermo Fisher, Invitrogen) suspension cells were grown in serum-free FreeStyle 293 expression medium (Invitrogen) and transfected according to the previously published protocol [35]. Briefly, a typical transfection experiment used $3\times10^7$ cells in 28 mL of FreeStyle medium mixed with 2 mL of OptiMem-I reduced serum medium containing 40 μL 293fectin transfection reagent (Invitrogen) and 20 μg of each expression plasmid under study. Cells were grown with shaking at 125 rpm on an orbital shaker platform in a 37° C. incubator with a humidified atmosphere of 8% $CO_2$ for 48 h total. In total, 200 μl of vesicles with xanthophylls were added, incubating for 5 hr under standard growth conditions.

(e) Antibodies

Rabbit polyclonal antibody 186 was custom made against the mouse BCO2 multiple antigenic peptides (MAP)-SKFLQSDTYKANSAG peptide and 7055 rabbit polyclonal antibody was produced by co-immunization of the two human BCO2 MAP-SHENLHQEDLEKEGGIE and MAP-QDNGRTLEVYQLQNLRKAG peptides.

(f) Characterization of Large Unilamellar Vesicles (LUVs) With Xanthophylls i. Dynamic Light Scattering The hydrodynamic diameter and polydispersity index (PDI) were measured at 30° C. on a Malvern Nano-ZS zetasizer (Malvern Instruments Ltd., Worcestershire, UK) equipped with a 4 mW helium-neon laser operated at 633 nm with a fixed scattering angle of 173°. An 80 μL sample was placed into disposable cuvettes without dilution (70 μL, center height 8.5 mm, BRAND° UV-Cuvette micro). Data were processed using non-negative least squares (NNLS) analysis.

ii. GC-MS Analysis

A Shimadzu GC-2010 Plus system with an AOC-20i Auto-Injector and a GCMS-QP2010 SE ion trap MS system (Shimadzu, Kyoto, Japan) was used for GC-MS analysis using the electron impact ionization mode. Chromatographic separations were performed on a Shimadzu SH-Rxi-5SiL MS capillary column (30 m×0.25 mm, 0.25 mm film thickness; non-polar phase: Crossbond™ 100% dimethyl polysiloxane as stationary phase). The temperatures of the injector and the GC-MS transfer line were 170 and 280° C., respectively. The carrier gas was ultrahigh purity helium (Airgas); the flow rate was 1.0 mL/min. The mass spectrometer was operated using the following parameters: the ratio of the split injection was 20:1, ionization voltage was 70 eV; ion source temperature was 200° C.; scan mode, 30.0-500.0 (mass range); scan rate, 5000 amu/s, and 3.68 scans/s; start time was 2 min. Electron multiplier (EM) voltage was obtained from autotune. The oven temperature was programmed to hold at 60° C. for 2 min, increase to 300° C. at 50° C./min, and hold at 300° C. for 3 min.

To measure the residual limonene in LUVs, a 100 μL aliquot is mixed with 1.9 mL of hexane and 50 mg of $CaSO_4$ (used here to disrupt the LUVs) and stirred for 30 min to extract limonene. The data were averaged from at least three independent measurements.

iii. Small-Angle X-Ray Scattering (SAXS)

The structural characteristics of LUVs were studied using small-angle X-ray scattering (SAXS). SAXS patterns were obtained using a Bruker NanoStar instrument equipped with a turbo rotating anode operated at 50 kV and 50 mA, evacuated beam path, two-pinhole collimators, Gobel mirrors selecting Cu—Kα radiation, and a large 2D Vantec-2000 detector. Samples were measured in 1.5 mm quartz capillaries; the measurement time was 3 h. Scattering patterns were collected in the range 0.006 Å−1<q<0.35 $Å^{-1}$. The sample to detector distance of 67.8 cm was verified using silver behenate as a calibration standard. The SAXS patterns were corrected for sample transmission and empty cell scattering. One-dimensional (1D) SAXS patterns were obtained by azimuthal integration of the resulting 2D images around the beam center, to obtain the intensity (ISAXS) vs. q profiles. The magnitude of the scattering vector was calculated as q=(4π/λ) sin(°/2), where θ is the scattering angle and λ is the X-ray wavelength for Cu—Kα (λ=1.5418 Å).

iv. Spectroscopic Determination of the Concentration of Xanthophylls

The concentrations of xanthophylls were measured using a 2 mm optical path quartz cell in an Agilent Cary 60 UV-Vis spectrophotometer. To measure the concentration of xanthophylls in LUVs, a 10 μL aliquot is mixed with 300 μL of DMF. Standards and samples were measured at least 3 times and the data were averaged. Final concentrations of xanthophylls in LUVs measured by UV/Vis: zeaxanthin 0.038 g/L (DPPC/DPPS, 0.45 μM final), zeaxanthin 0.14 g/L (DMPC/DMPS); lutein 0.0125 g/L (DMPC/DMPS, 0.15 μM and 0.06 μM final); violaxanthin 0.07 g/L (DMPC/DMPS, 0.6 μM final).

v. BCO2 Protein Palmitoylation was Analyzed by Acyl-Resin-Assisted Capture (ACYL-RAC)

For cell lysis and the Acyl-RAC assay, the same protocol as previously described in detail, with slight modifications [34,36], was used. BCO2-overexpressing HEK293F cells were washed with 1X-PBS and resuspended in lysis buffer (50 mM HEPES (pH 7.4) containing 150 mM NaCl, 5 mM EDTA, 1% glycerol, and 1× complete protease inhibitor cocktail (Roche Diagnostics)). Resuspended cells were lysed using $N_2$ cavitation followed by centrifugation at 900×g for 10 min at 4° C. to remove the cell debris and nuclei. The clarified supernatant was then subjected to centrifugation at 20,000×g for 30 min at 4° C. to obtain heavy membrane (mitochondrial) pellet and post-mitochondrial supernatant (light membrane and cytosol) fractions. Typically, a 1000 μg amount of resuspended heavy membrane pellet protein (resuspended in lysis buffer containing 0.1% Triton X-100) was used for palmitoylation detection assay. Briefly, free cysteine sulfhydryl (—SH) groups were blocked with 0.5% (v/v) S-methyl methanethiosulfonate (MMTS) containing blocking buffer for 15 min at 40° C. The blocked protein samples were then subjected to acetone protein precipitation. The protein pellet was then resuspended in 550 μl 100 mM HEPES containing 5 mM EDTA and 1% SDS (v/v). The samples were then divided into two 250 μl aliquots (containing 400 μg protein amount) and the remaining 50 μl was used as an input. The samples were treated with 250 mM hydroxylamine ($NH_2OH$, HAM) or control (250 mM NaCl). To capture proteins with free —SH groups, each sample was mixed with 10 mg activated thiol-sepharose 4B beads (Sigma) and incubated for 2 h at room temperature with continuous end-over-end rotation. After incubation, the beads were washed, and bound proteins were eluted by boiling the beads with an aliquot of 50 μL elution sample buffer. The input and eluted fractions from "HAM" and "control" samples were separated by SDS-PAGE and analyzed by Western blotting.

vi. Immunocolocalization Studies BCO2 Protein in Different Organelles Upon Substrate Treatment Using Confocal Microscopy BCO2-overexpressing COS7 cells ($1\times10^6$ cells/mL) seeded on poly L-lysine coated 18 mm coverslips were analyzed by immunofluorescence microscopy to determine the localization of BCO2 protein in different subcellular organelles as described previously [34]. Briefly, COS7 cells were transfected with 20 μg of BCO2-Lumio V5 tag plasmid using Fugene® 6 transfection reagent (1:6 DNA: Fugene 6 ratio). After 43 h, BCO2-transfected cells were treated with substrate-encapsulated LUVs for 5 h. Fixed cells were immunostained with V5 monoclonal and polyclonal antibodies alone and together with primary antibodies specific for different subcellular organelles (ER (PDIA3), Golgi (MAN2A1), mitochondria (COX IV and HSP60), and peroxisomes (PMP70)), followed by Alexa fluorophore-conjugated secondary antibodies (Invitrogen). Cell nuclei were stained with DAPI (1 μg/μL solution; Sigma). Slides were then visualized with a Zeiss LSM 700 confocal microscope using a 40× oil immersion lens/1.4-NA and Zeiss ZEN software. Pearson's correlation coefficient values were determined for analysis of the co-localization of BCO2 protein and different organelles and represented as mean±standard deviation. For nuclear co-localization of BCO2 protein, the Pearson's correlation coefficient of BCO2 with DAPI-stained nuclei was measured using the results from three independent experiments: single labeling of BCO2 "alone", double labeling of BCO2 with mitochondrial markers COX IV and HSP60. Results shown were typical of a minimum of three independent experiments with 5-10 fields of view containing on average 1-10 cells/field of view. For quantification and statistical analyses, at least 100 cells were observed for each organelle and nuclear co-localization.

vii. Construction of Models and Ligand Docking Simulations

A model of mBCO2 was constructed with the Swiss-Model program using the RPE65 4F30 crystal as a template [37]. The loop carrying the PDPCK motif is unresolved in this crystal and is given in this model as a random loop. To model the unresolved areas, the mBCO2 sequence with distances specified for the catalytic histidines was submitted to the I-Tasser server [38-40]. Five models were obtained; however, the side chains of the Fe-coordinating histidines and glutamates were displaced relative to both the Swiss-Model and RPE65 crystals. The sidechains of the histidines and glutamates of the top I-Tasser model were modified based on the Swiss-Model and the RPE65 crystal structures. Finally, to model an active state, the Fe center and the $O_2$ and OH of the VP14 crystal (PDB: NPE3) were aligned with both models and integrated into the models. Clashes resulting from the introduction of $O_2$ and OH on the Fe center were corrected by torsioning the relevant residues. Ligand dockings were carried out using Autodock Vina [41]. In general ligand restraints chosen allowed for all possible torsions.

b. Xanthophyll Delivery System

LUVs were prepared by hydration of lipid with carotenoids and assisting limonene, followed by extrusion and extraction of limonene to yield unilamellar vesicles with a narrow size distribution, as confirmed by SAXS and DLS, respectively (FIG. 7B-7D, FIG. 8). The amount of carotenoids associated with LUVs was determined by UV-vis spectroscopy following a previously published protocol [42]. Previously, it was shown that, depending on the structure of the substrate, as well as on the composition of lipids, hydrophobic carotenoids are oriented differently in the phospholipid bilayer of delivery vesicles [43]. Thus, symmetrically oxy-functionalized carotenoids intercalate into phospholipid membranes perpendicular to the membrane surface [44], while fully non-polar β-carotene is intercalated parallel to the surface within the hydrophobic core of phospholipid bilayers [44,45]. In addition, the molecular length of a carotenoid affects the degree of its intercalation into phospholipid bilayers, depending on the membrane thickness [42]. In fact, zeaxanthin ($C_{40}$) was better incorporated into unilamellar vesicles of dimyristoylphosphatidylcholine (n-$C_{14}$), whereas decaprenozeaxanthin ($C_{50}$) was better adopted in unilamellar vesicles of dipalmitoylphosphatidylcholine (n-$C_{16}$). On the other hand, the inclusion of large hydrophobic molecules into the phospholipid bilayer can change the structure as well as the thickness of vesicles [46]. To understand the membrane structure of vesicles as well as the organization of carotenoids within DMPC and DPPC LUVs with associated zeaxanthin, X-ray scattering measurements were performed. The phosphate-phosphate (p-p) thicknesses obtained from the SAXS data fit gave values of ~35.1 Å for DMPC-zeaxanthin membranes and ~41.2 Å for DPPC-zeaxanthin membranes, which is the typical thickness for DMPC and DPPC-carotenoid LUVs [42, 46]. The length values (FIG. 1A) of the carotenoid (lutein or zeaxanthin) correspond well to the length of the lipophilic segment of DMPC, but not DPPC. This is the reason for the much weaker incorporation of lutein (or zeaxanthin) into DPPC membranes compared to DMPC [42, 47].

c. Palmitoylation of Mouse BCO2 (MBCO2) in the Presence of Xanthophylls

Figure 9A:
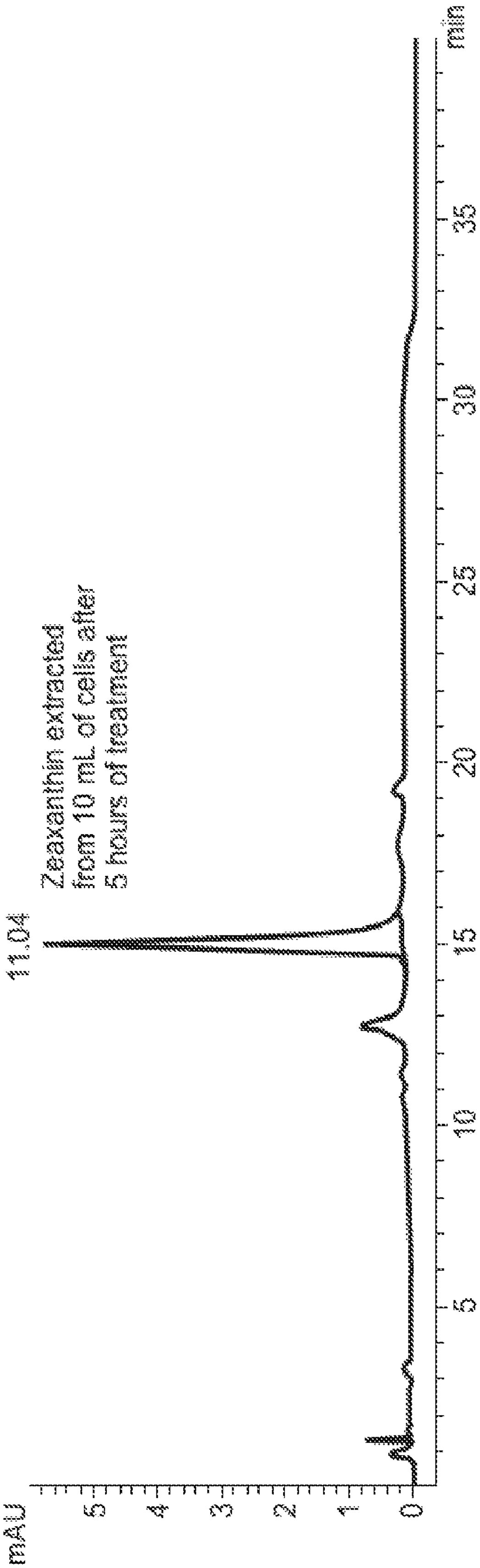
FIG. 9A-B are representative High Performance Liquid Chromatography (HPLC) plots of zeaxanthin extracted from HEK293F cells and media.
Figure 9B:
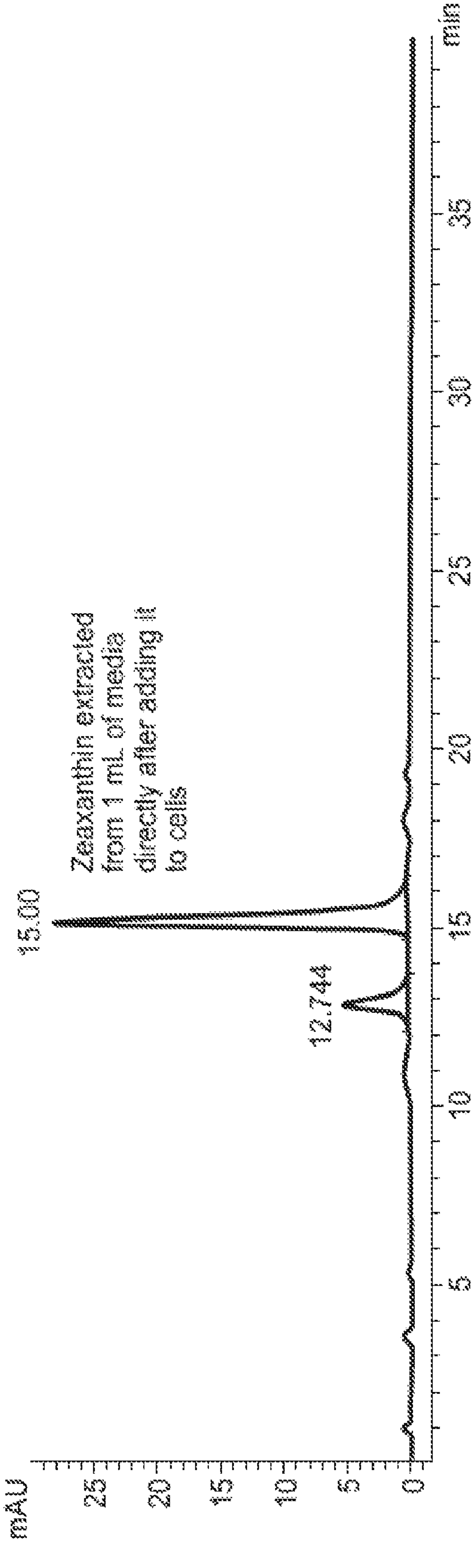
Figure 10A:
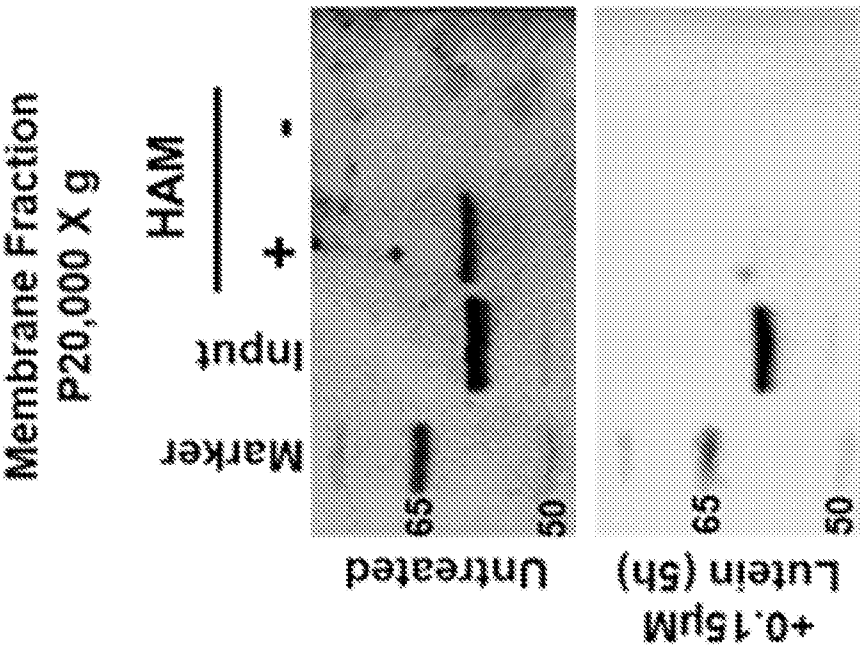
FIG. 10A-D are representative Western blot images depicting the monitoring of the palmitoylation status as analyzed by Acyl-RAC assay of mBCO2 upon treatment with different substrates.
Figure 10B:
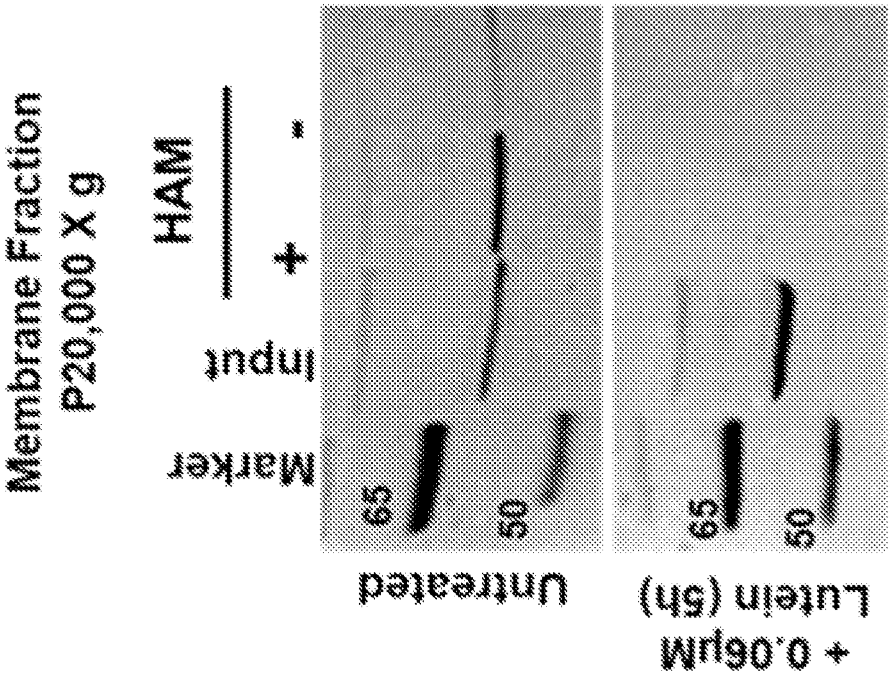
Figure 10C:
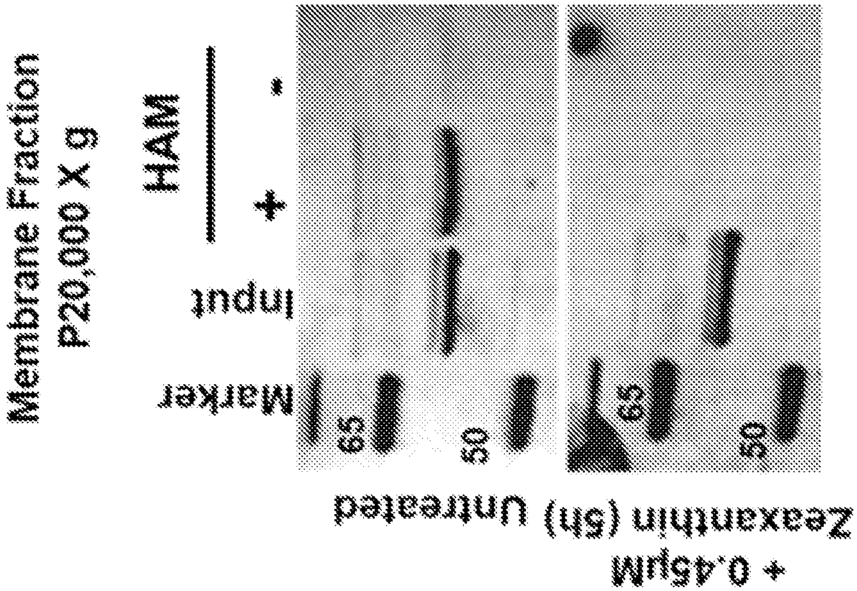
Figure 10D:
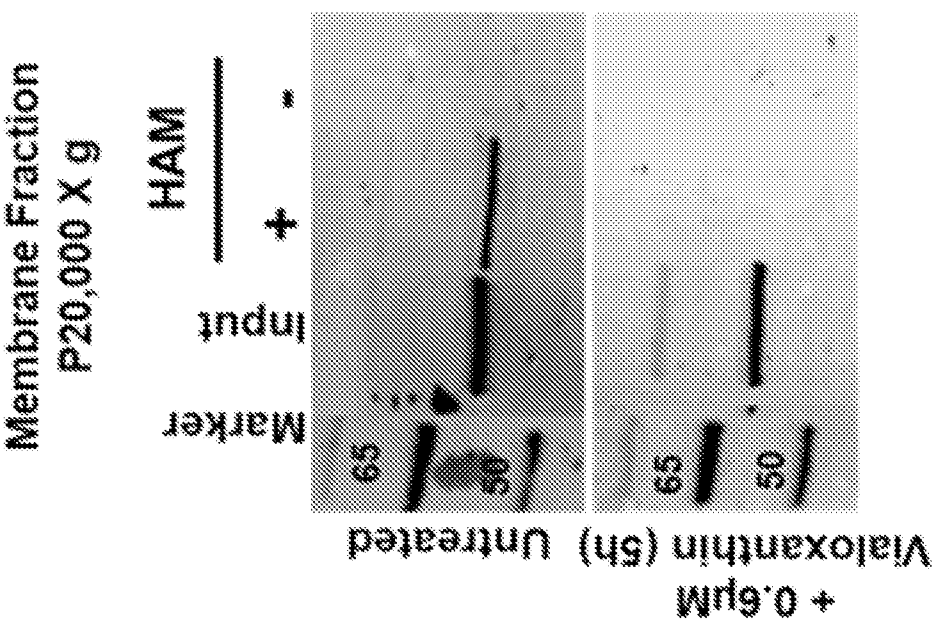
Figure 11A:
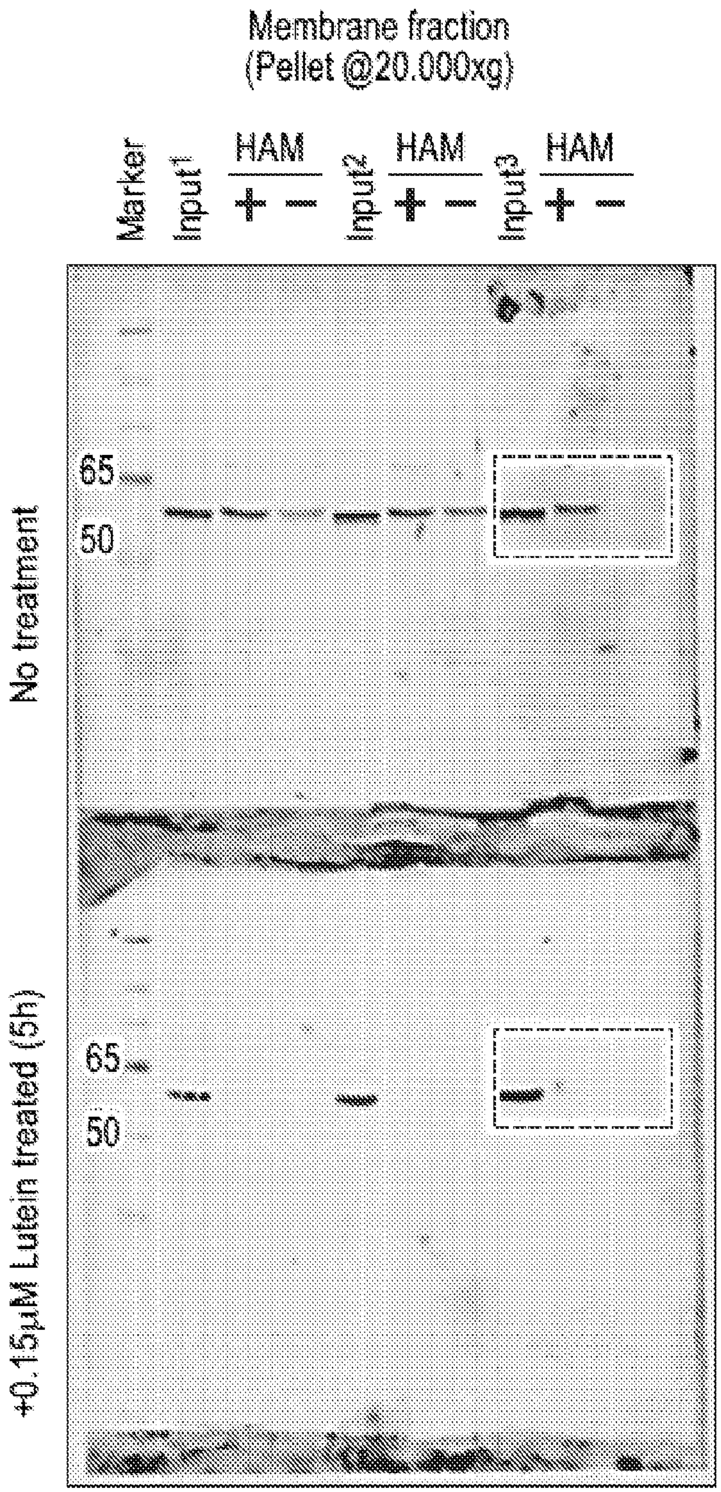
FIG. 11A-D are representative raw Western blots for the detection of mouse BCO2 palmitoylation by acyl-RAC assays.
Figure 11B:
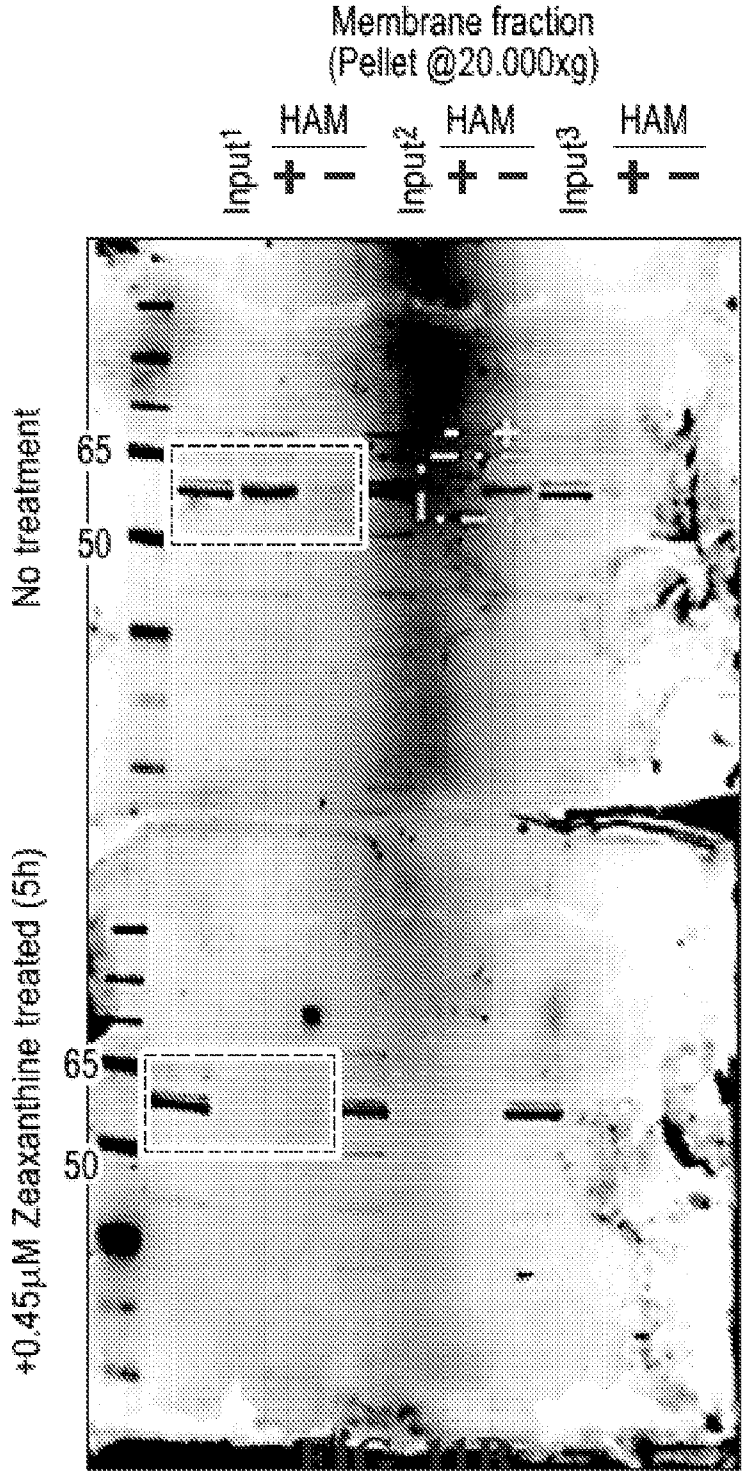
Figure 11C:
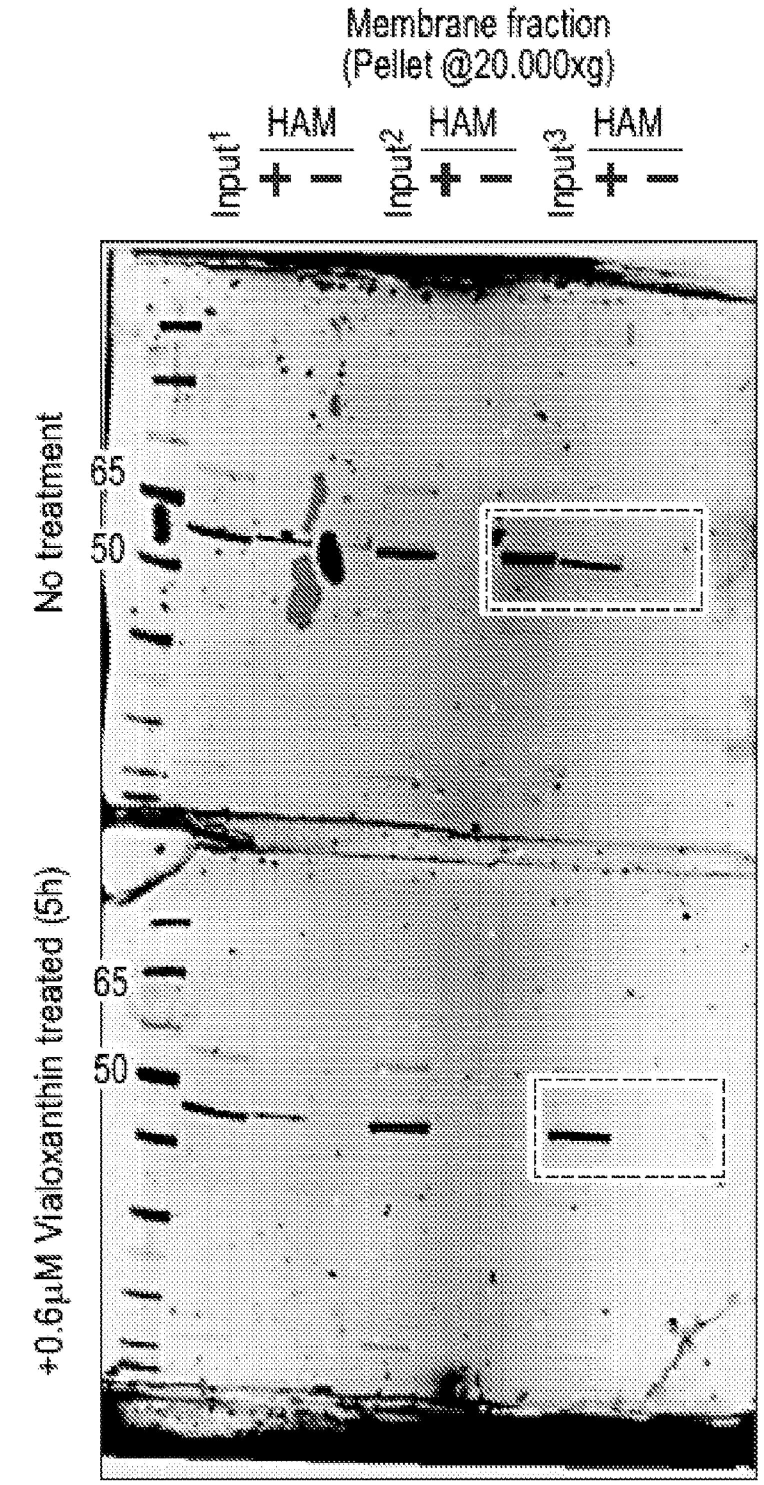
Figure 11D:
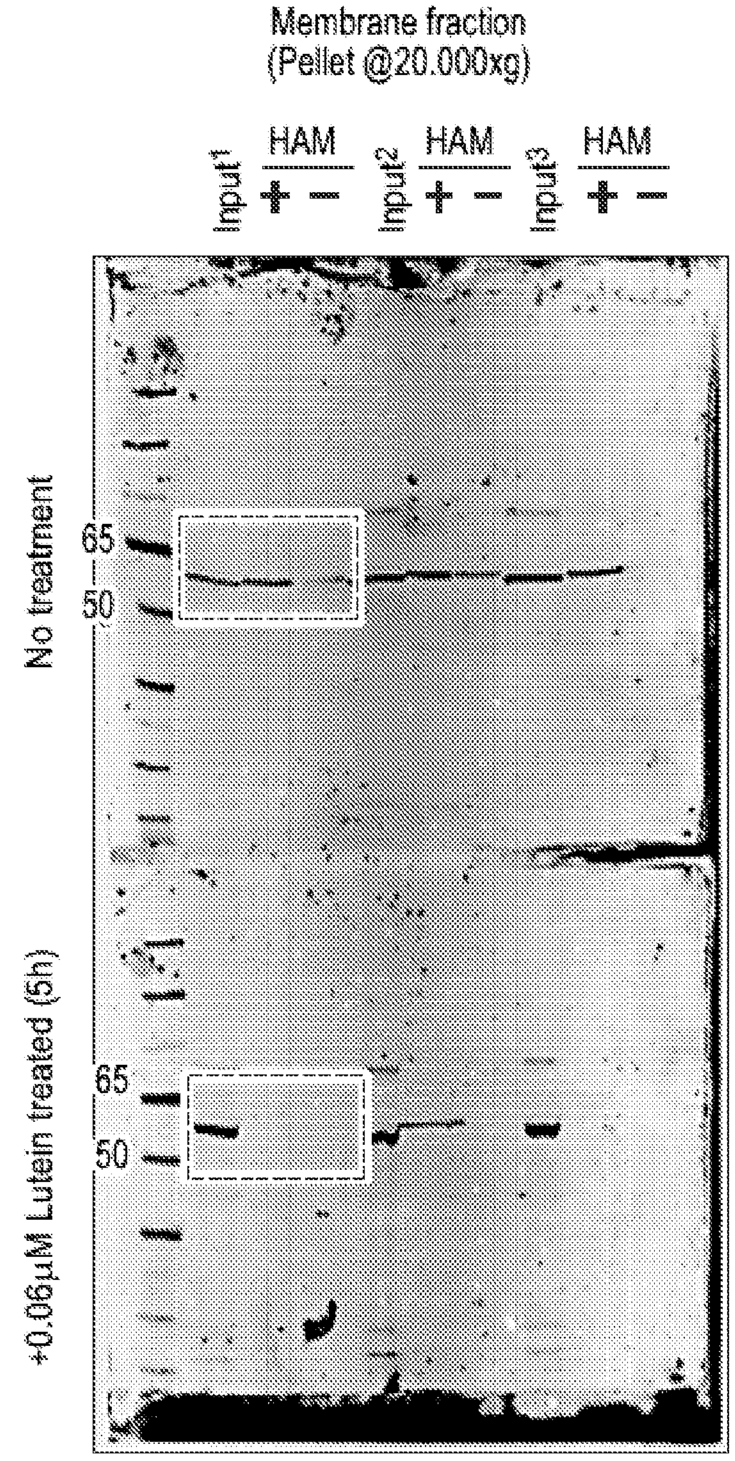
Figure 12A:
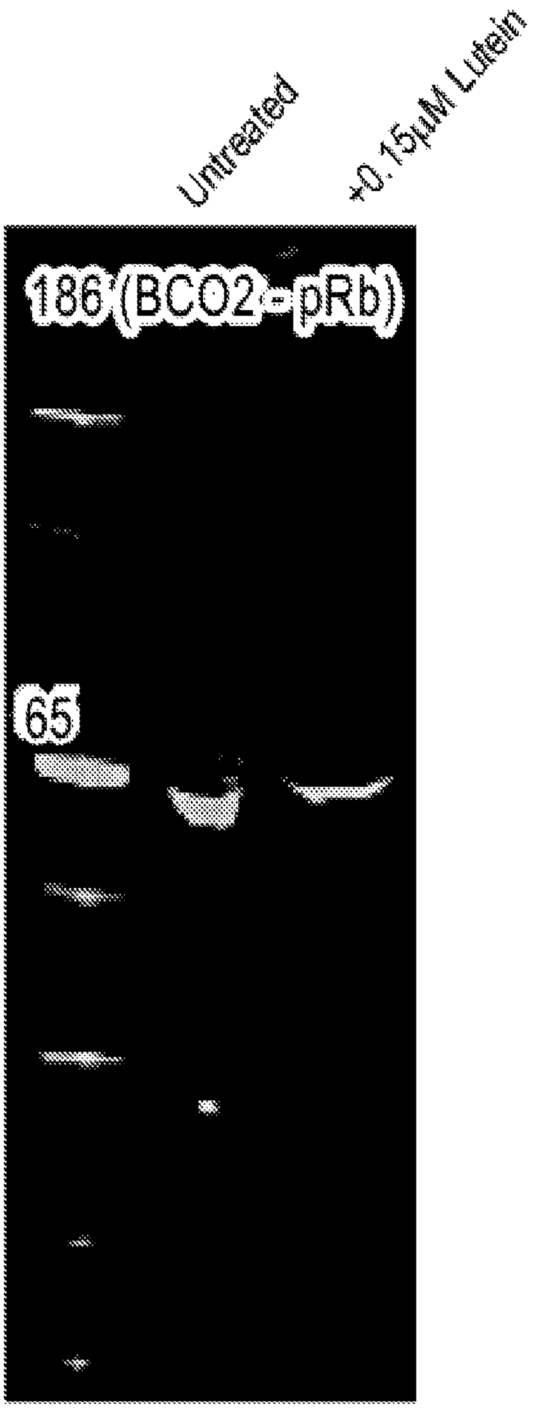
FIG. 12A-F are representative immunofluorescence microscopy images for mBCO2 protein expression in COS7 cells transfected with VS-tagged mBCO2. COS7 cells expressing mBCO2 protein treated with different substrates for 5 h were grown on poly-L-lysine coated coverslips and subjected to immunolocalization studies using confocal microscopy. For immunoblotting, post-nuclear supernatant was separated by SDS-PAGE. The presence of V5-tagged mBCO2 was probed by immunoblotting with rabbit polyclonal anti-mouse BCO2 and mouse monoclonal anti-V5 antibodies.
Figure 12B:
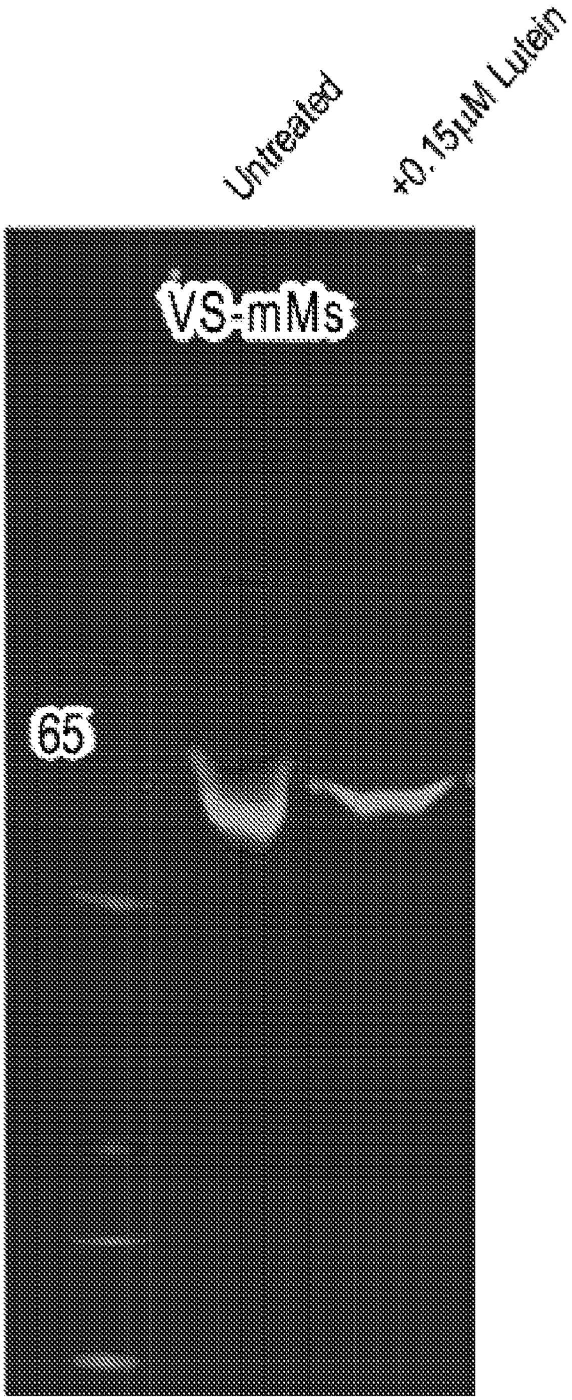
Figure 12C:
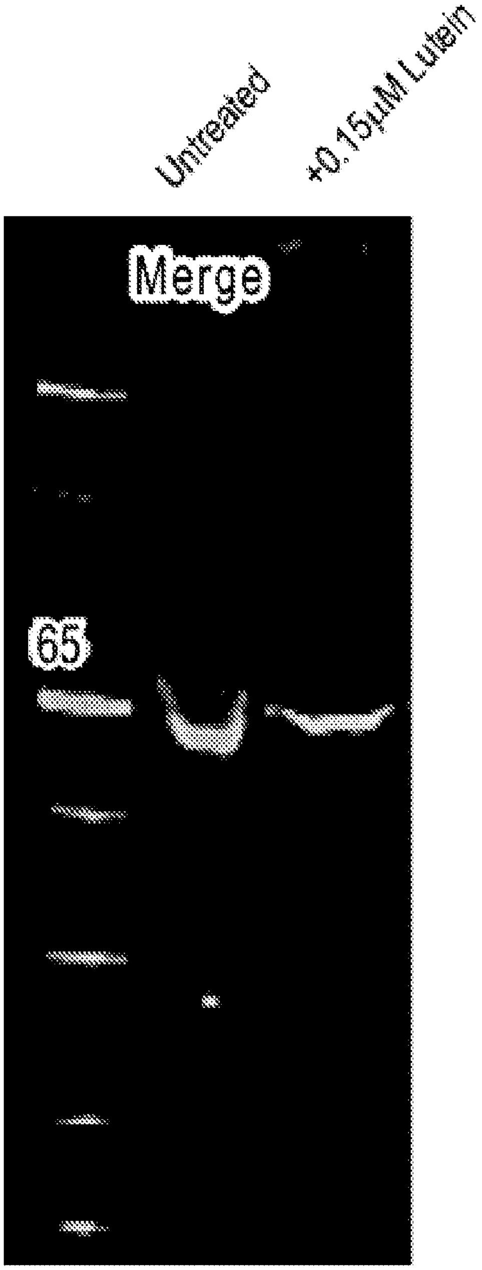
Figure 12D:
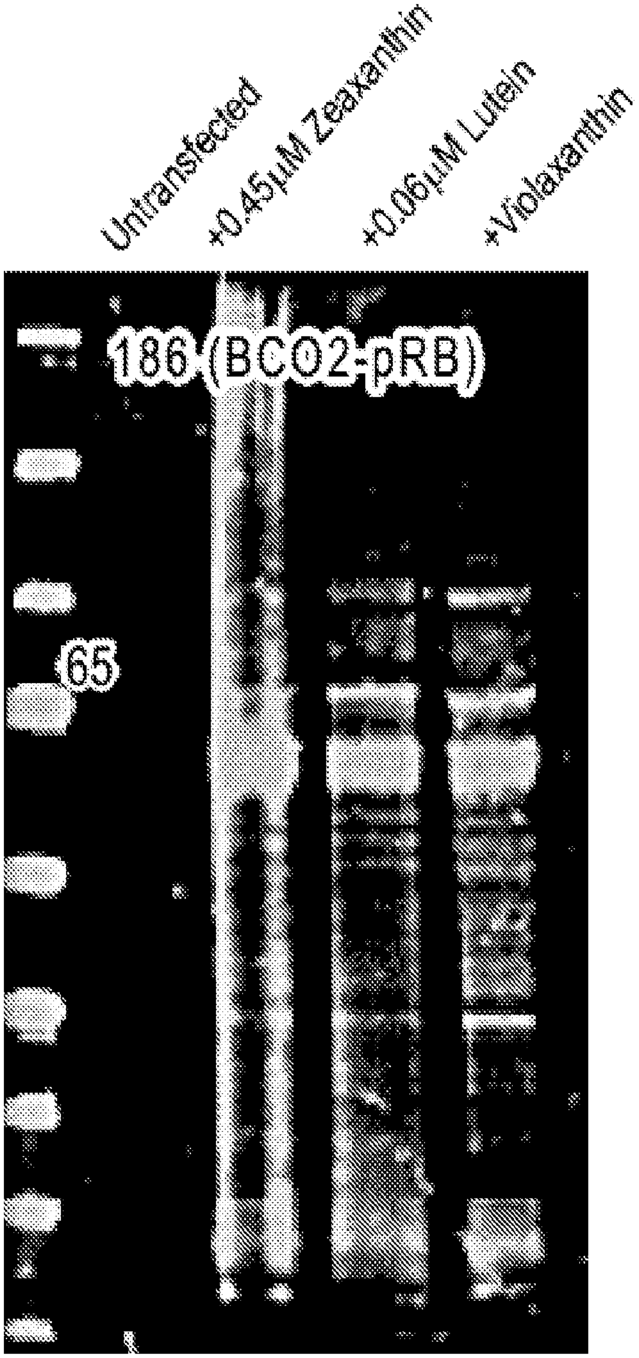
Figure 12E:
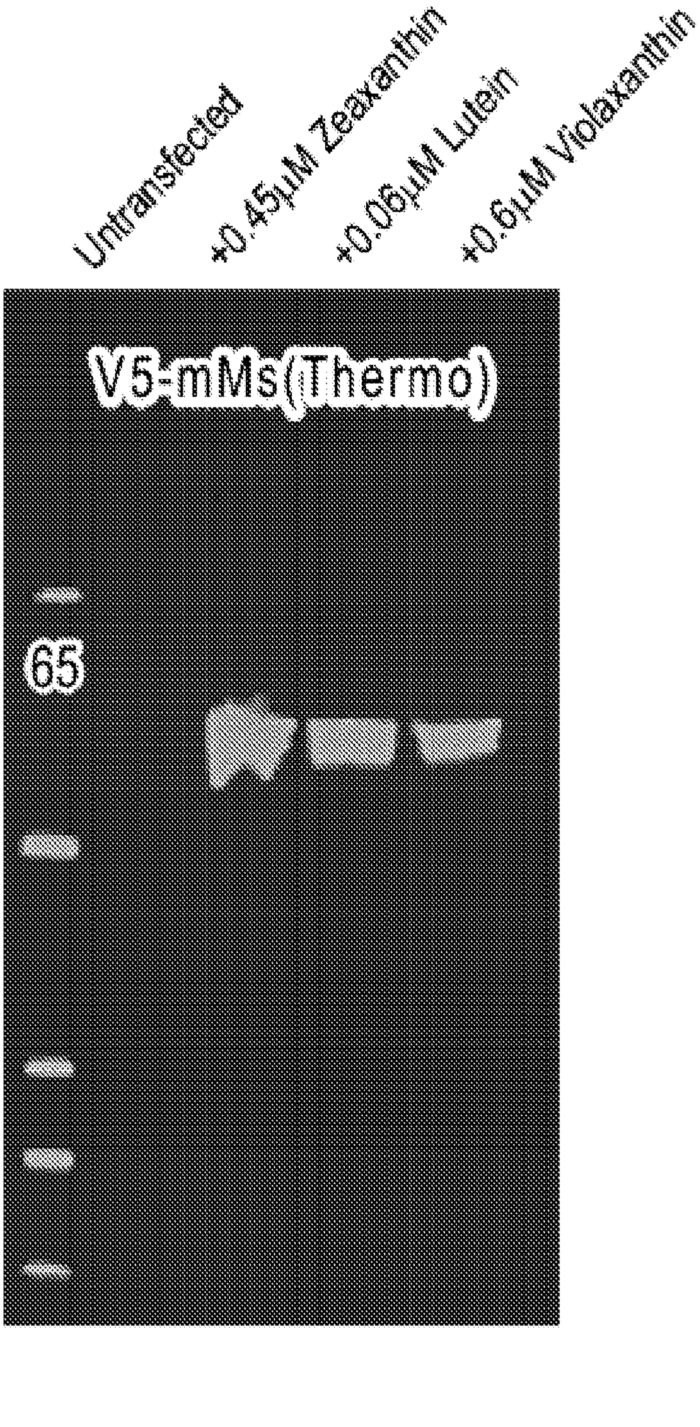
Figure 12F:
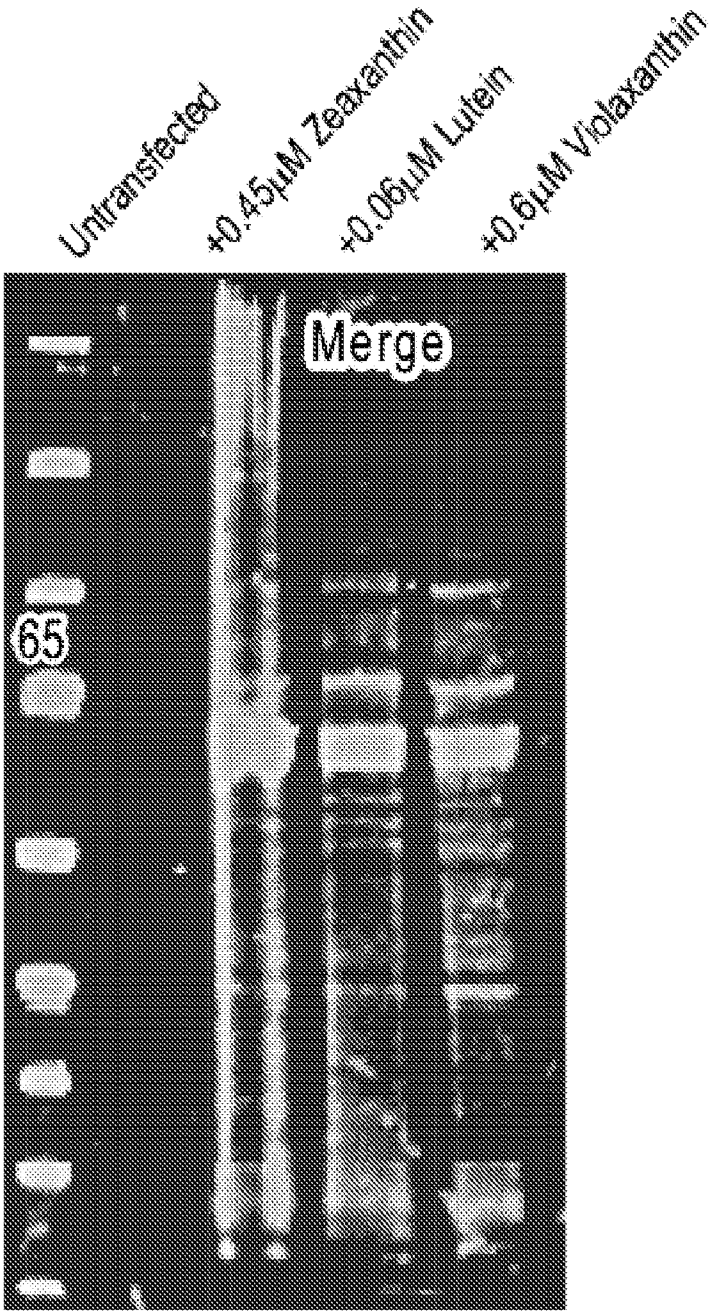
Figure 13A:
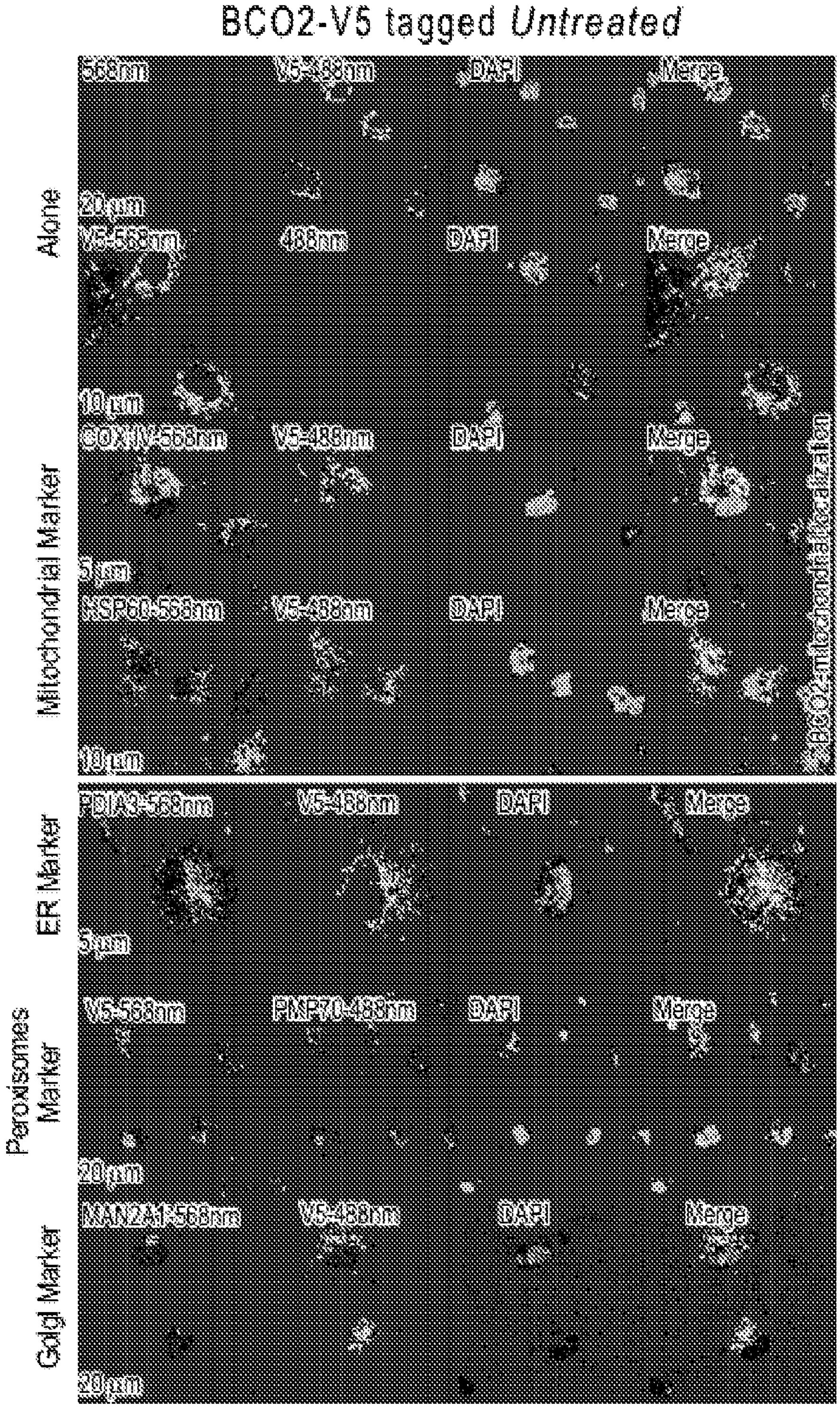
FIG. 13A-D show representative data for the characterization of subcellular localization of mBCO2 treated with lutein.
Figure 13B:
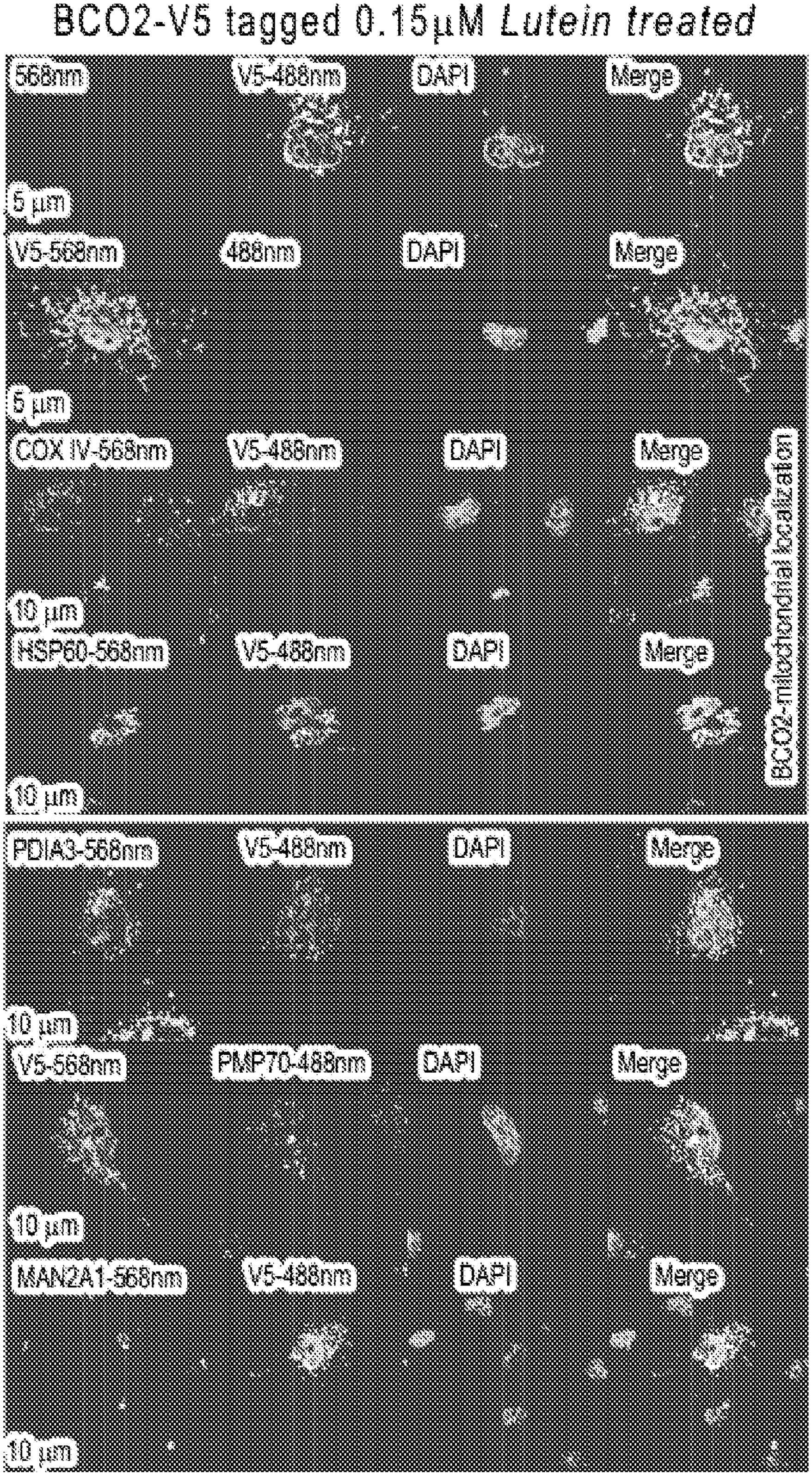
Figure 13C:
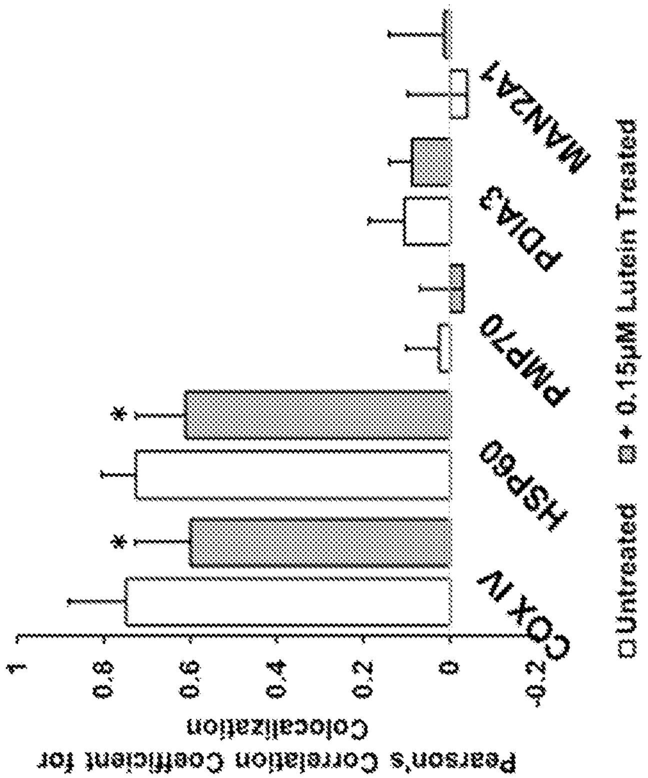
Figure 13D:
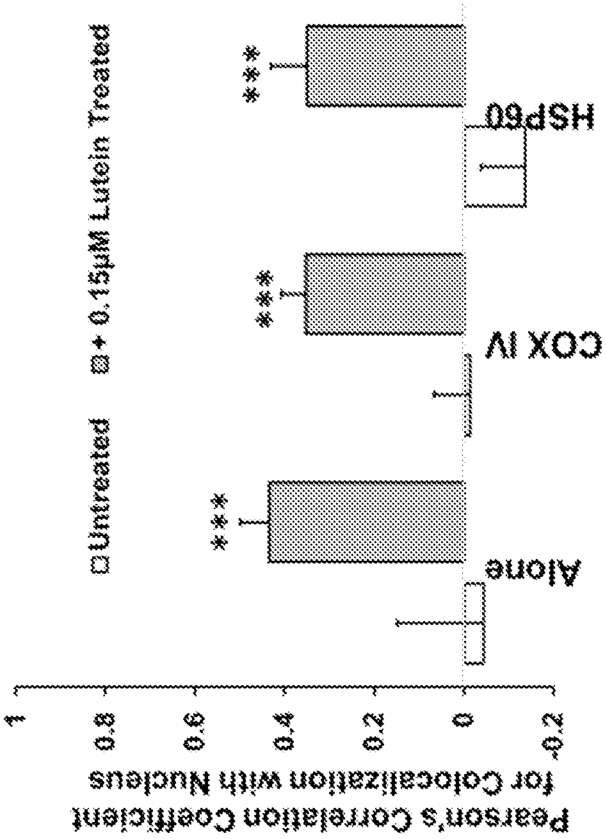
Figure 14A:
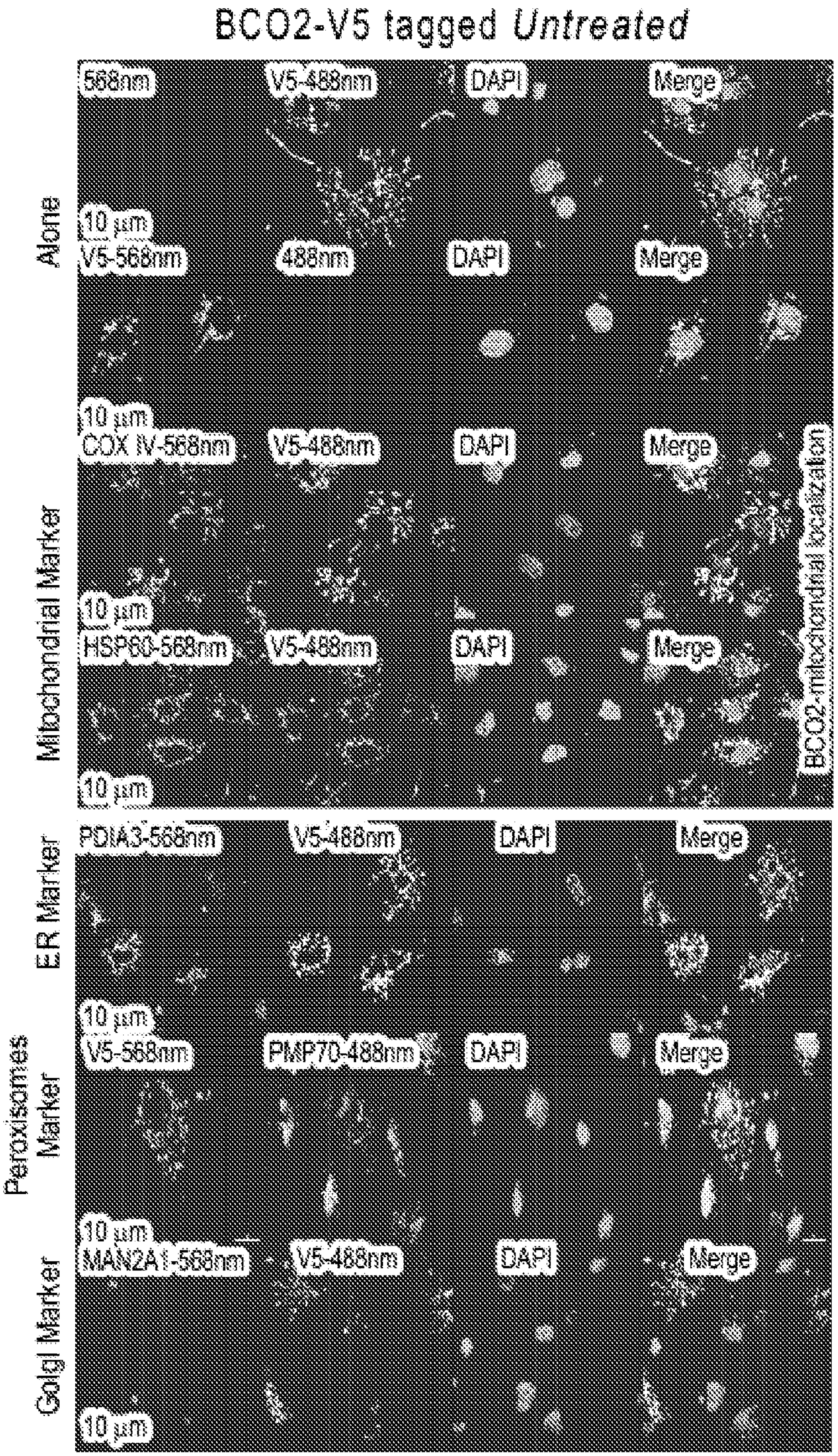
FIG. 14A-D show representative data for the characterization of subcellular localization of mBCO2 treated with zeaxanthin.
Figure 14B:
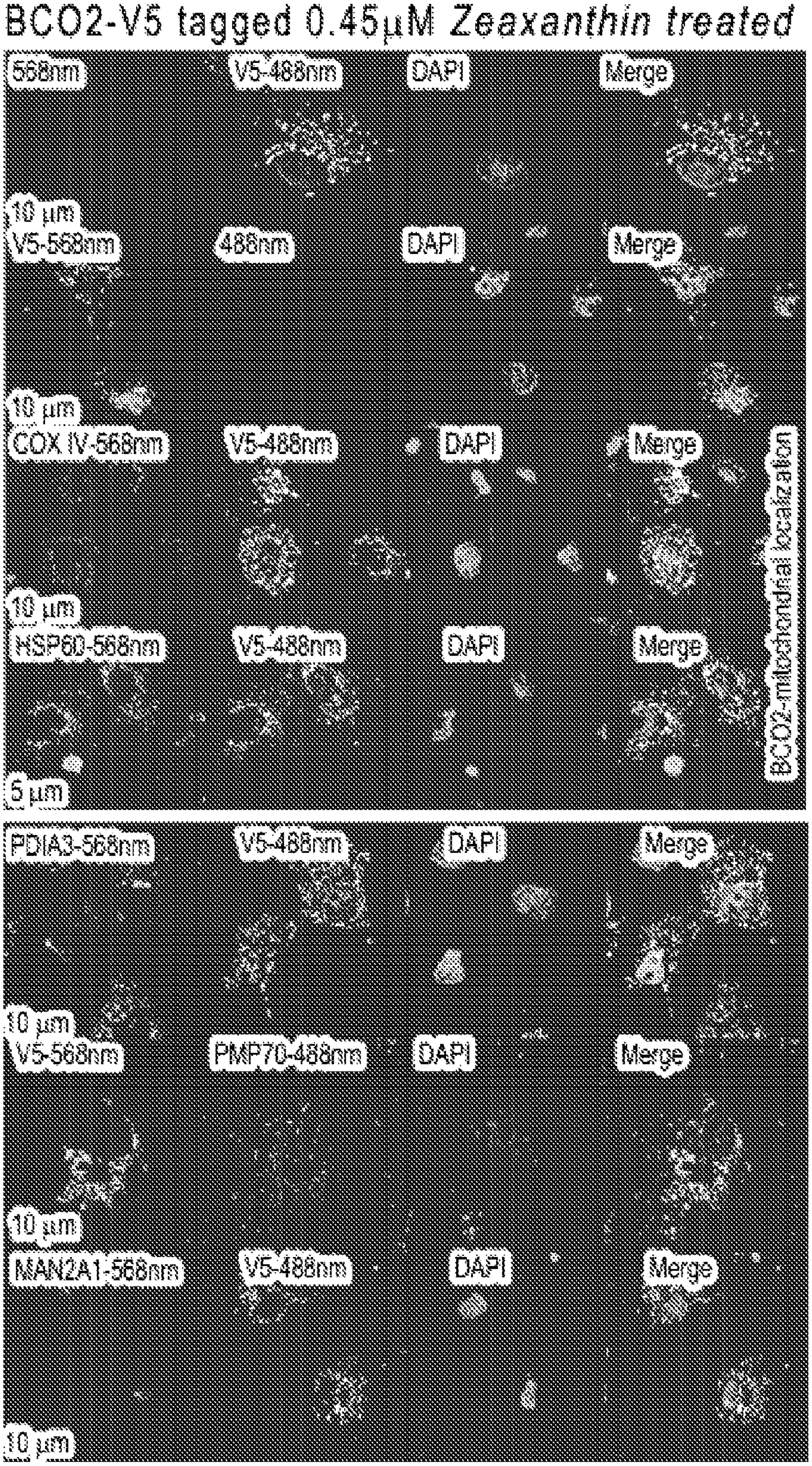
Figure 14C:
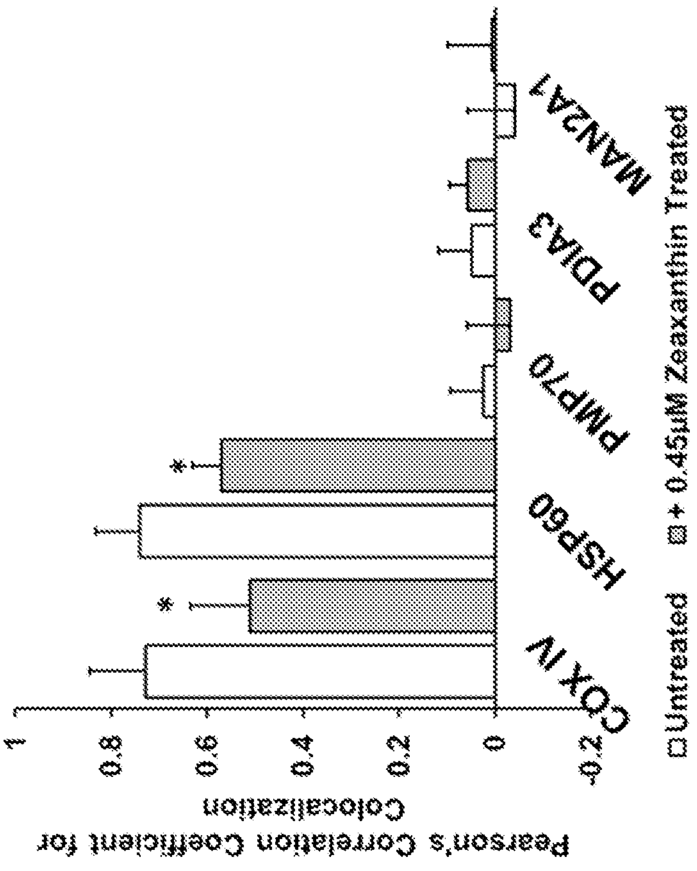
Figure 14D:
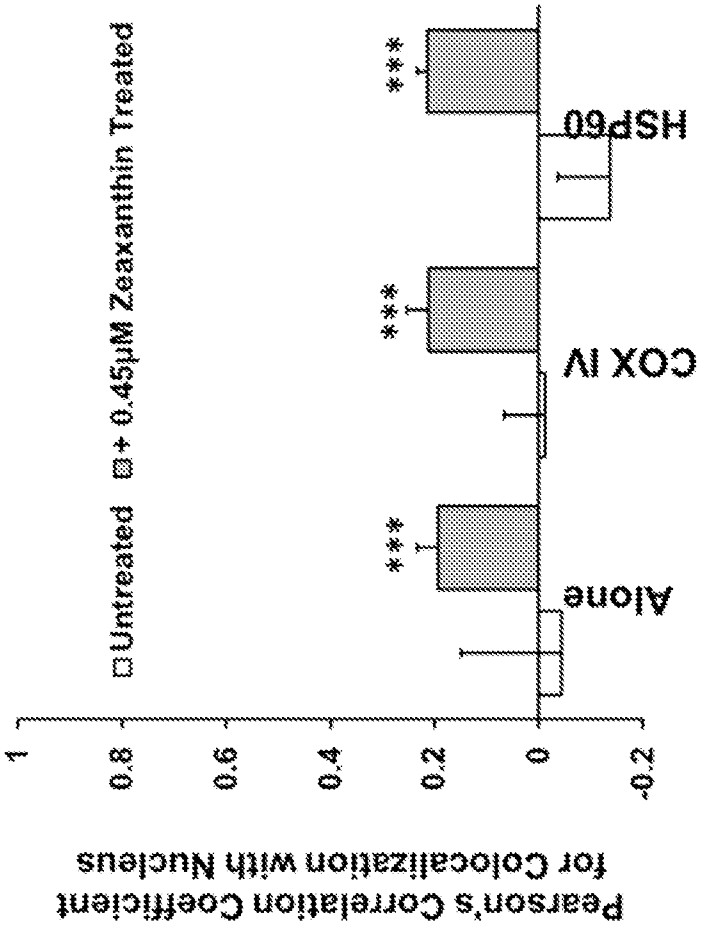
Figure 15A:
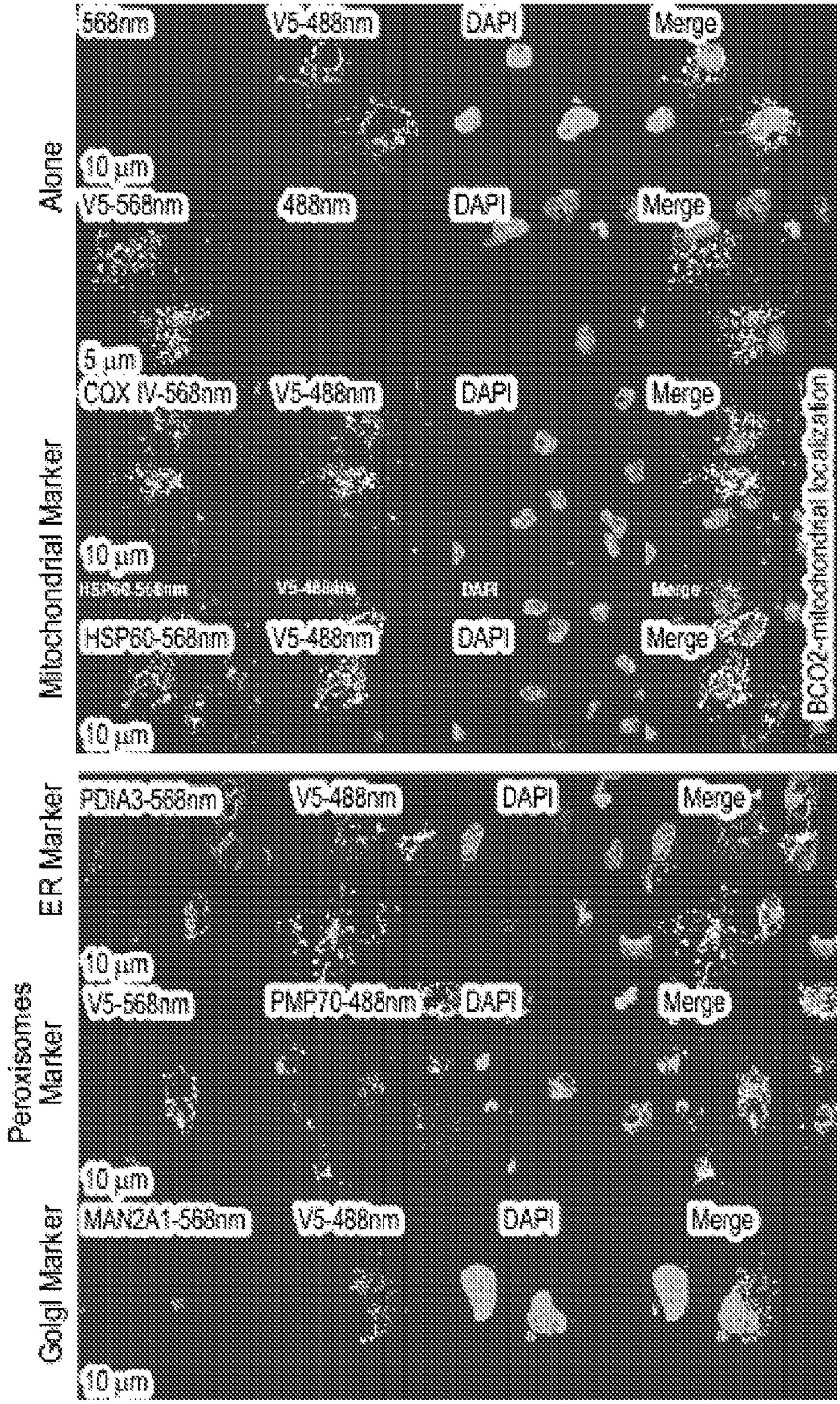
FIG. 15A-D show representative data for the characterization of subcellular localization of mBCO2 treated with violaxanthin.
Figure 15B:
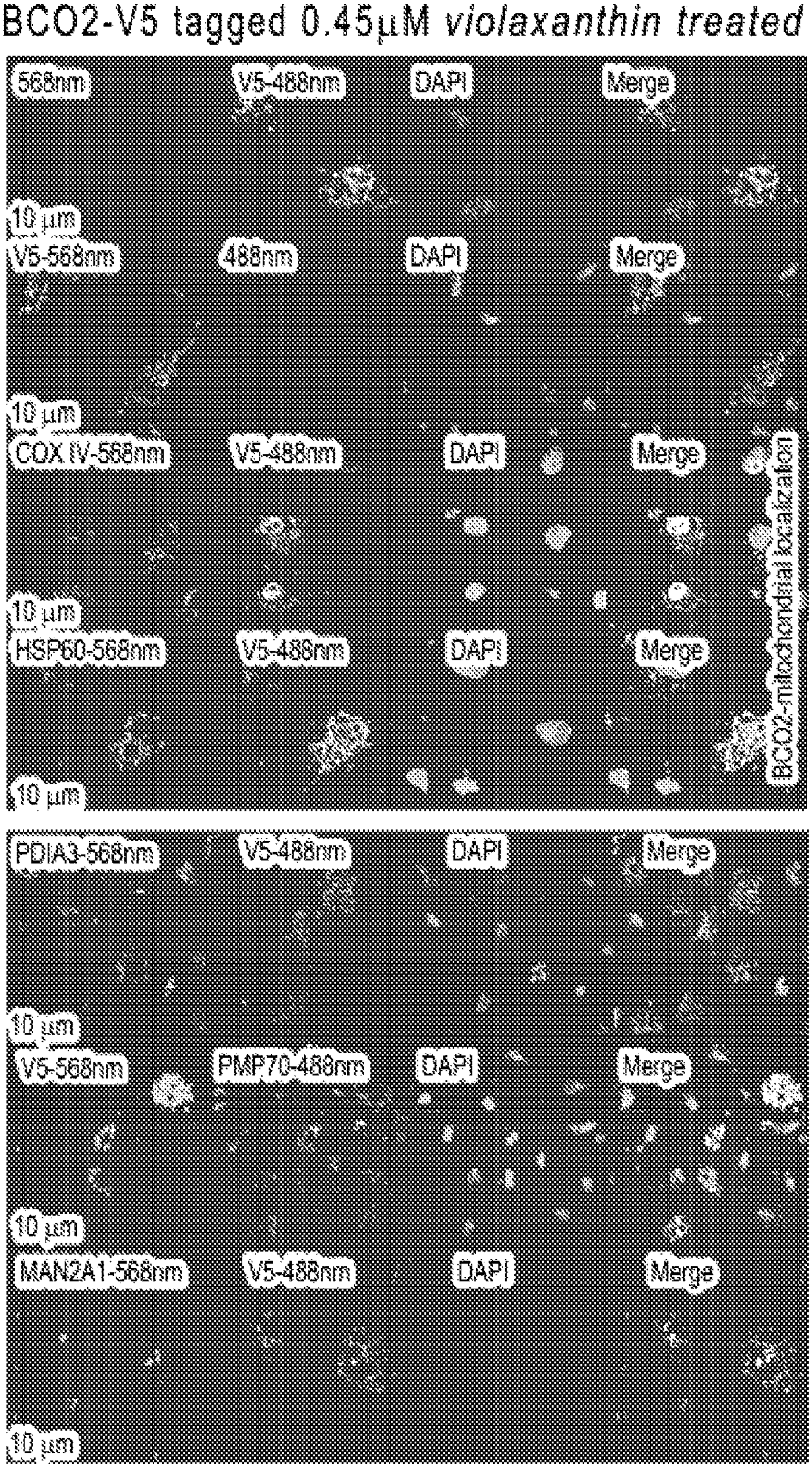
Figure 15C:
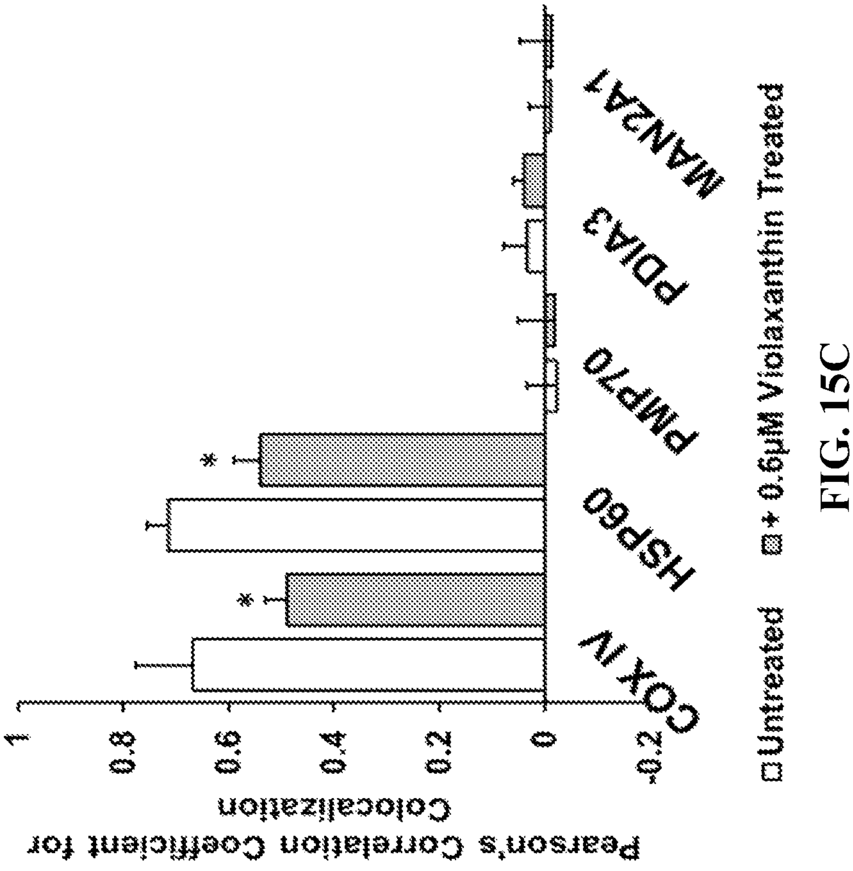
Figure 15D:
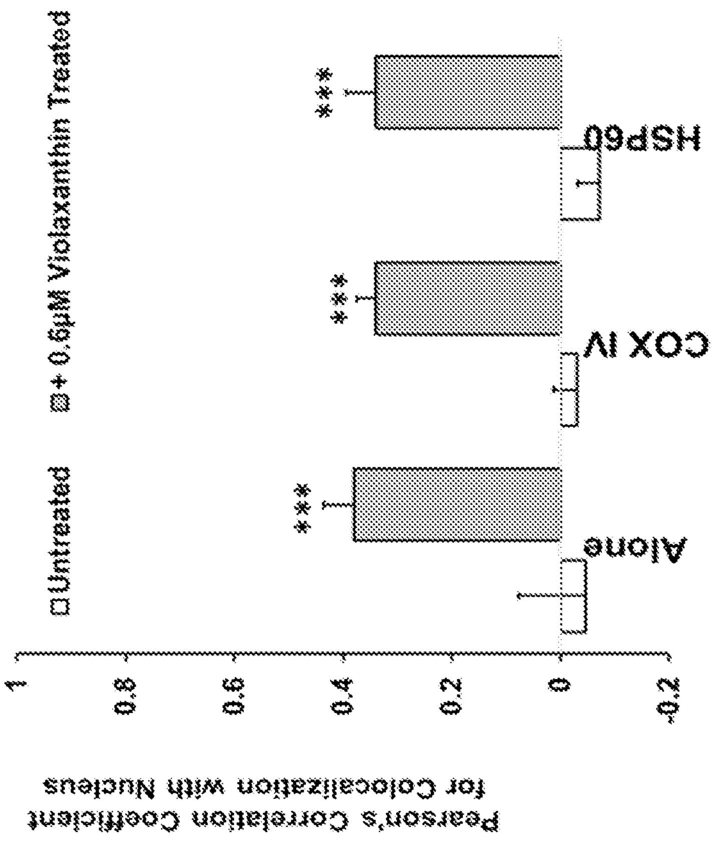

It was previously established that mBCO2 in eukaryotic HEK293F cells is palmitoylated. It was discovered that in the presence of the mBCO2 substrate β-carotene mBCO2 loses palmitoylation [34]. Knowing that BCO2 cleaves xanthophylls [17, 48, 49], palmitoylation assays were ran to study the palmitoylation status of mBCO2 in the presence of xanthophylls. First, xanthophylls were attempted to be delivered with the detergent Tween 40 [50]. It was found that a higher concentration of Tween 40 (0.1%) led to HEK293F cell apoptosis as was previously described for HepG2 cells [51], while a lower concentration (0.01%) eluted mBCO2 from membranes during the Acyl-RAC assay even without hydroxylamine treatment. Therefore, a new method to deliver xanthophylls without detergents using unilamellar LUVs as described above was established. The content of xanthophylls in the HEK293F cells after 5 h of treatment was similar to a Tween 40 delivery system in ARPE-19 cells (1-2%) (FIG. 9A-9B) [52]. Subsequently, the acyl-RAC method was used as described previously. The membrane fraction of HEK293F cells expressing mBCO2 was subjected to treatment with hydroxylamine (+HAM) and an equal portion of the fraction was treated with 250 mM NaCl (−HAM) which served as control. In the absence of substrates, mBCO2 protein showed an intense protein band in the HAM-treated sample (FIG. 10A-10D, full Western blots are presented in FIG. 11A-11D), while there was no protein band in the control NaCl-treated sample, indicating S-palmitoylation of BCO2 protein. In contrast, when cells were pre-treated with 0.15 μM lutein and 0.06 μM in DMPC/DMPS micelles, no protein band was detected in the HAM-treated sample (FIG. 10A-10B, FIG. 11A, and FIG. 11D, lutein panel). Similar results were obtained with DPPC/DPPS-encapsulated zeaxanthin (0.45 μM) (FIG. 10C and FIG. 11B) and DMPC/DMPS-encapsulated violaxanthin (0.6 μM) (FIG. 10D and FIG. 11C).

d. Sub-Cellular Localizaton of mBCO2 With and Without Xanthophylls: Shuttling the Enzyme to the Nucleus Next, BCO2 localization by immunofluorescence microscopy was examined using mBCO2 transfected COST cells with various organellar markers (for mitochondria, peroxisomes, endoplasmic reticulum (ER), and Golgi). It was confirmed that V5 tag antibodies recognize specifically mBCO2-V5 protein in transfected HEK293F cells (FIG. 12A-12F). For nuclear labeling, DAPI nuclear stain was used. Immunofluorescence results as shown in FIG. 13A (upper panel) revealed the extensive mitochondrial colocalization with both COXIV and heat-shock protein 60 (HSP60) (FIG. 13A, upper panel). No colocalization of mBCO2 with other organelles was observed (FIG. 13A, bottom panel, and FIG. 14C) as indicated by their low correlation coefficient score compared with mitochondrial localization. These data are in full agreement with previous results for human BCO2 [21,34]. However, upon addition of substrates to mBCO2, it was observed that a fraction of mBCO2 colocalizes with the nuclear DAPI stain and the colocalization with mitochondrial markers is significantly decreased (FIG. 13B, top panel, and FIG. 13D). The percent of colocalization with nuclear marker is higher when cells are treated with lutein and violaxanthin than with zeaxanthin. See FIG. 14A-D and FIG. 15A-D.

Figure 16A:
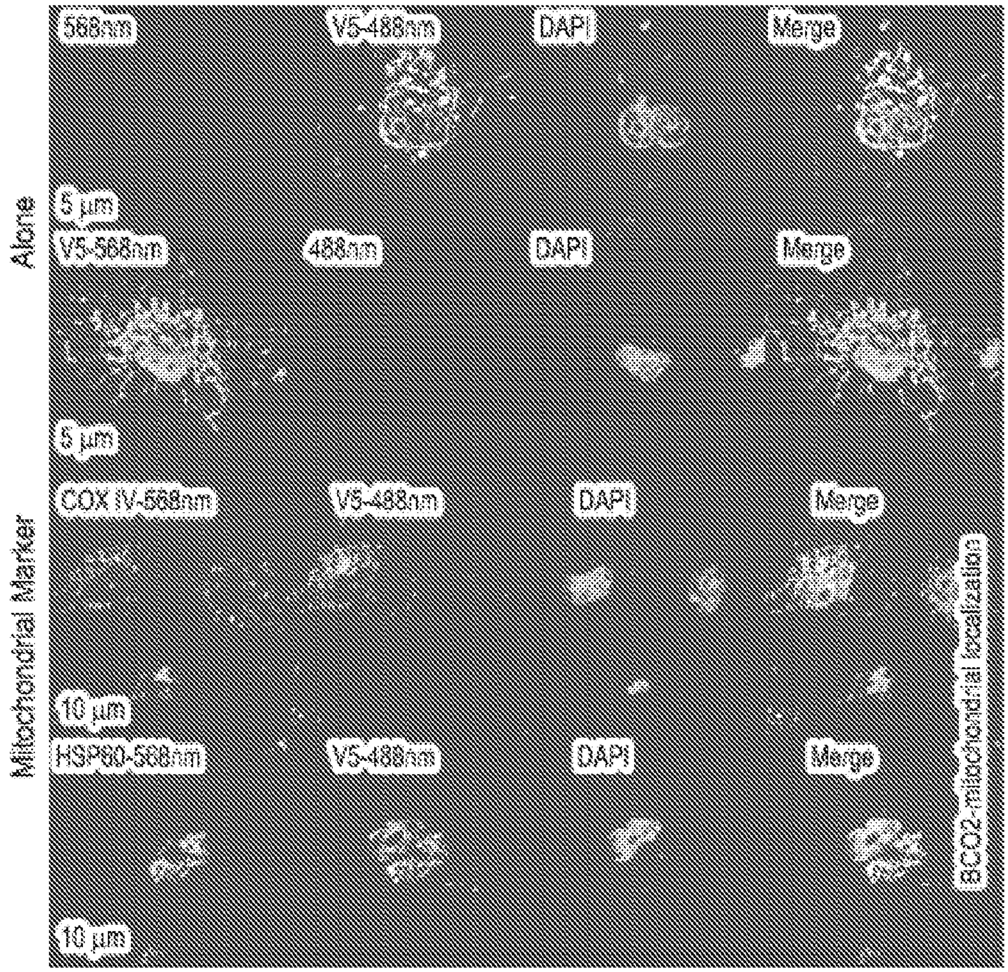
FIG. 16A-C show representative data for the cellular localization of VS-tagged mouse BCO2 with and without lutein.
Figure 16B:
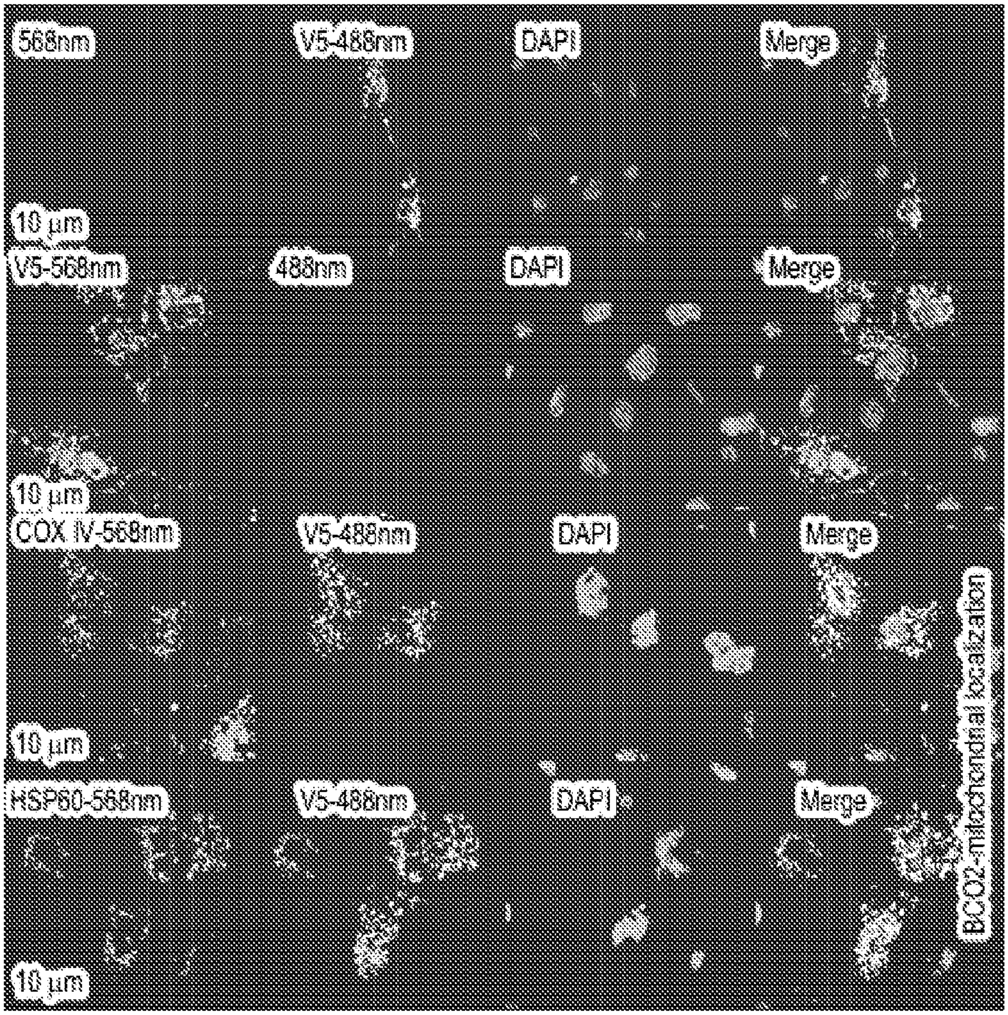
Figure 16C:
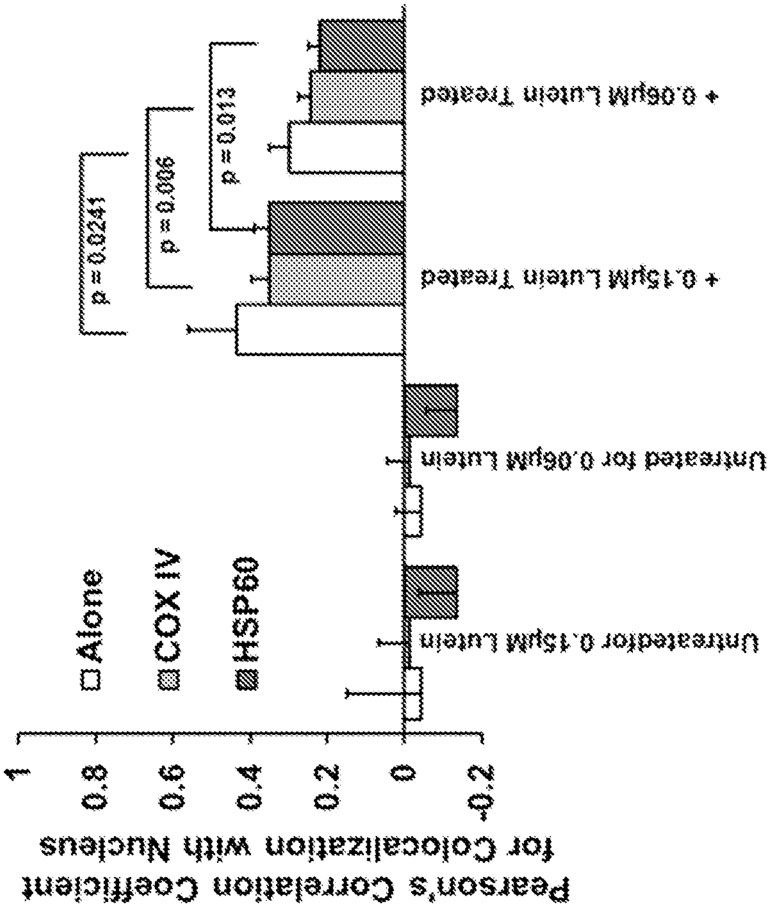

When the experiment was performed using a lower concentration of lutein (0.06 μM), it was observed that the percent colocalization of BCO2 in the nucleus decreased in a lutein concentration-dependent manner (FIG. 16A-16C). Previously, mBCO2 colocalization with the nuclear DAPI stain was observed when cells were treated with β-carotene [34]. It correlates with the observation from the acyl-RAC assay that residual mBCO2 palmitoylation is seen in some samples in the presence of zeaxanthin, violaxanthin and a low concentration of lutein (FIG. 11).

e. Modeling of Xanthophyll Docking in Mouse BCO2

To understand these findings, modeling of substrate (lutein, zeaxanthin and violaxanthin) docking in mBCO2 was performed. The Swiss-Model random coil model of the bovine RPE65 4F30 crystal with the helical -PDPCK-containing loop modeled in (using I-TAS SER as described in Methods) was used as a basis to model mBCO2. The highest binding energy to the Swiss-Model model of mBCO2 protein was observed with lutein and the lowest with zeaxanthin. However, zeaxanthin binding energy significantly increased in Modell (clash-free I-TASSER model which corrected the catalytic H and E residues orientation from the Swiss-Model model) docking simulation, while lutein and violaxanthin binding energy did not change, as shown in Table 1.

TABLE 1

| Carotenoid | SwissPro Model | I-TASSER Model1 |
|---|---|---|
| violaxanthin | −11.0 | −10.8 |
| zeaxanthin | −11.8 | −10.1 |
| lutein | −10.5 | −10.4 |
| β-carotene | −11.8 | −10.6 |

Figure 17A:
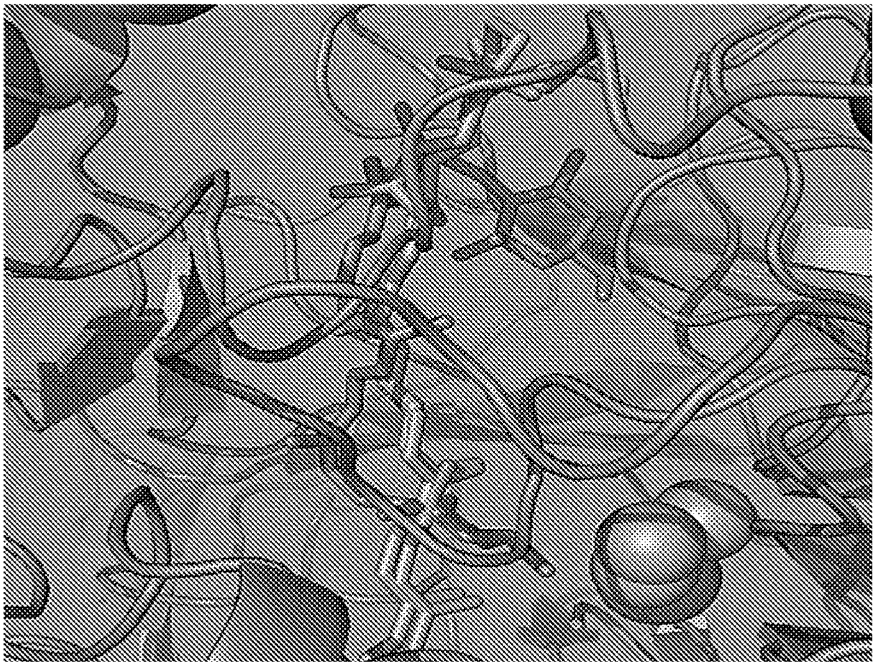
FIG. 17A and FIG. 17B are images showing visualizations of carotenoid docking.
Figure 17B:
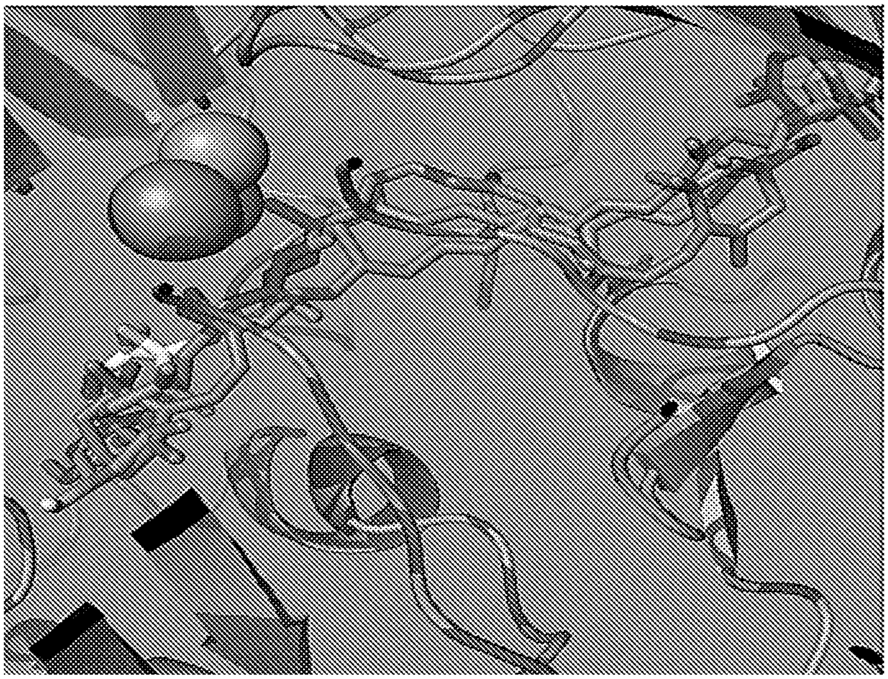

Additionally, zeaxanthin did not line up well in the mBCO2 active site and curled up in both of the models (FIG. 17A and FIG. 17B).

f. Discussion

As demonstrated, xanthophylls affect the palmitoylation status of mBCO2 and direct translocation of the enzyme to the nucleus where xanthophylls could modulate gene expression and exert antioxidant properties through activation of cellular oxidative stress response genes. To accomplish this, a new unique non-disruptive way for membranes to deliver xanthophylls to cells was developed. Thus, LUVs with xanthophylls were produced by using limonene to assist solubilization of the xanthophyll in bilayers made of phospholipids of the appropriate size. These findings expand on previous findings regarding substrate-induced depalmitoylation and organellar relocalization of mBCO2 and suggest a common effect of carotenoids on this enzyme.

The catalytic activity of mBCO2 towards certain oxidative metabolites of zeaxanthin was recently documented [17]. There are numerous other xanthophylls in the human diet. For example, violaxanthin is a diepoxy derivative of zeaxanthin and accumulates in a significant mount in human ovaries [53]. However, it was not known if it is a substrate and if mBCO2 could cleave it. The results suggest that it does. It will be useful to better understand substrate structural requirements for mBCO2 function in cells.

Xanthophylls are well known for their antioxidant protective properties which may play a role in delaying chronic diseases. Despite this, it is still far from clear how xanthophylls exert the full extent of their antioxidant properties [54]. A widely proposed pathway is that they dissipate excess energy from potentially harmful oxidants, such as excited triplet states of singlet oxygen, by virtue of their extended conjugated bond systems and thereby protect membranes from oxidant stress [11]. Recently, however, a body of literature has begun to accumulate, pointing to direct regulation of gene expression by xanthophylls [50,55]. This would be analogous to the role of β-carotene metabolites in transcriptional regulation: β-apocarotenoids have been recently found to function as transcriptional regulators, specifically as nuclear receptor antagonists, which inhibit retinoic acid activities [56-59]. In this regard, lutein has been shown to activate Nrf2, an emerging regulator of cellular resistance to oxidants, and to affect Nrf2 pathway genes in retinal cells [50, 60]. It has been demonstrated that lutein effectively protects ARPE-19 from damage generated by hyperglycemia by activating Nrf2 through its regulators, suggesting a preventive role of lutein against diabetic retinopathy [60]. How lutein (and other carotenoids/carotenoid metabolites) might enter the nucleus occurs is currently unknown.

In this respect, it was previously described that presence of β-carotene changes the palmitoylation status of mBCO2 and that we can see residual colocalization with the nucleus [34]. Thus, the results with lutein, zeaxanthin and violaxanthin extend these prior findings by demonstrating that, generally, mBCO2 is palmitoylated in the absence of substrates and that it loses palmitoylation when substrates are present in the cells. Therefore, it prompts the proposition that loss of palmitoylation upon substrate-treatment somehow influences the BCO2-mitochondrial localization and promotes the shuttling of BCO2 to the nucleus. The mechanism of substrate bound-BCO2 shuttling to the nucleus is still unclear and needs to be investigated in further detail to explore the unclear function of BCO2 in the nucleus. Differences in binding of substrates to mBCO2 as demonstrated in the molecular docking experiments could define differences in nucleus shuttling and antioxidant effect of the various xanthophylls. Additionally, it is important to further study if mBCO2 could work as a transporter of xanthophylls and their metabolites to the nucleus (in addition to β-carotene and its metabolites), and to elucidate the potential mode of action of xanthophylls and their enzymatic metabolites on gene expression in relation to an oxidative stress response, in addition to their quenching properties.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of making a unilamellar liposome, the method comprising mixing a lipid, a terpene, and a hydrophobic cargo molecule, thereby forming a mixture, and loading the mixture into a lipid bilayer, wherein the terpene facilitates incorporation of the hydrophobic cargo molecule into the lipid bilayer.

2. The method of claim 1, wherein the lipid is a phosphatidylcholine or a phosphatidylserine.

3. The method of claim 2, wherein the lipid is 1,2-dimyristoyl-sn-glycero-3-phosphocholine (DMPC), 1,2-dimyristoyl-sn-glycero-3-phospho-L-serine (DMPS), 1,2-dipalmitoyl-sn-glycero-3-phosphocholine (DPPC), 1,2-dipalmitoyl-sn-glycero-3-phospho-L-serine (DPPS), or a combination thereof.

4. The method of claim 1, wherein the terpene is a monoterpene selected from limonene, geraniol, α-terpineol, thymol, menthol, carvone, eucalyptol, perillaldehyde, myrcene, mentho, carvone, hinokitiol, linalool, careen, sabinene, camphor, menthol, camphene, thujene, camphor, borneol, eucalyptol, and ascaridole.

5. The method of claim 4, wherein the monoterpene is selected from limonene and geraniol.

6. The method of claim 1, wherein the method further comprises mixing an assisting molecule with the lipid, terpene, and hydrophobic cargo molecule to form the mixture, wherein the assisting molecule is selected from the group consisting of divinylbenzene, tert-butylstyrene, tert-butylmethacrylate, butylmethacrylate, 1,4-butanediol dimethacrylate, and a combination thereof.

7. The method of claim 1, wherein the molar ratio of the terpene to the lipid is of from about 0.25:1 to about 10:1.

8. The method of claim 1, wherein the molar ratio of the terpene to the lipid is of from about 0.25:1 to about 2:1.

9. The method of claim 1, wherein the hydrophobic cargo molecule is Lutein, Zeaxantin, Violaxantin, Astaxantin, Carotene, Cilostazol, Cilostamide, or a combination thereof.

10. The method of claim 1, wherein the hydrophobic cargo molecule further comprises is a nucleic acid.

11. The method of claim 10, wherein the nucleic acid is deoxyribonucleic acid (DNA).

12. The method of claim 10, wherein the nucleic acid is ribonucleic acid (RNA).

13. The method of claim 1, further comprising hydrating the mixture prior to the loading step.

14. The method of claim 1, further comprising removing the terpene.

15. The method of claim 14, wherein removing is via extraction with a solvent that is immiscible with water.

16. The method of claim 1, wherein the method does not comprise a post-processing step.

17. The method of claim 16, wherein the post-processing step is extrusion, sonication, or a combination thereof.

18. A method of making a unilamellar liposome, the method comprising:

(1) mixing a lipid, a terpene, and a hydrophobic cargo molecule in a solvent, wherein the terpene facilitates incorporation of the hydrophobic cargo molecule into the lipid bilayer;

(2) evaporating the solvent to form a lipid film;

(3) hydrating the lipid film to form a unilamellar liposome; and (4) extracting the terpene from the unilamellar liposome.

* * * * *